US012662672B2

(12) United States Patent
Ng et al.

(10) Patent No.: US 12,662,672 B2
(45) Date of Patent: Jun. 23, 2026

(54) METHOD OF PROMOTING SURVIVAL AND/OR FUNCTION OF A MOTOR NEURON AND RELATED AGENTS, USES AND METHODS

(71) Applicant: Agency for Science, Technology and Research, Singapore (SG)

(72) Inventors: Shi Yan Ng, Singapore (SG); Boon Seng Soh, Singapore (SG); Jin Hui Hor, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1167 days.

(21) Appl. No.: 17/635,190

(22) PCT Filed: Aug. 28, 2020

(86) PCT No.: PCT/SG2020/050504
§ 371 (c)(1),
(2) Date: Feb. 14, 2022

(87) PCT Pub. No.: WO2021/040627
PCT Pub. Date: Mar. 4, 2021

(65) Prior Publication Data
US 2022/0290155 A1 Sep. 15, 2022

(30) Foreign Application Priority Data
Aug. 30, 2019 (SG) ........................... 10201908013X

(51) Int. Cl.
*C12N 15/113* (2010.01)
*A61K 31/37* (2006.01)
*A61P 25/28* (2006.01)
*G01N 33/50* (2006.01)

(52) U.S. Cl.
CPC .......... *C12N 15/1137* (2013.01); *A61K 31/37* (2013.01); *A61P 25/28* (2018.01); *G01N 33/5058* (2013.01); *C12N 2310/14* (2013.01); *C12N 2320/30* (2013.01)

(58) Field of Classification Search
CPC ............ C12N 15/1137; C12N 2310/14; C12N 2320/30; A61K 31/37; A61K 31/455; A61P 25/28; G01N 33/5058
See application file for complete search history.

(56) References Cited

U.S. PATENT DOCUMENTS

| | | | | |
|---|---|---|---|---|
| 7,250,289 | B2 * | 7/2007 | Zhou .................... | C12Q 1/6837 536/23.1 |
| 11,655,510 | B2 * | 5/2023 | Chenchik ............. | C12Q 1/6886 435/6.1 |
| 2006/0003322 | A1 * | 1/2006 | Bentwich ............... | G16B 15/10 435/6.16 |

FOREIGN PATENT DOCUMENTS

| | | | |
|---|---|---|---|
| EP | 2213738 | A2 | 8/2010 |
| WO | WO 1991/019813 | | 12/1991 |
| WO | WO 2006/006948 | A2 | 1/2006 |
| WO | 2009120561 | A2 | 10/2009 |
| WO | 2018002783 | A1 | 1/2018 |
| WO | WO 2018/213420 | A1 | 11/2018 |

OTHER PUBLICATIONS

Hor, Jin-Hui, et al. ("ALS Motor Neurons Exhibit Hallmark Metabolic Defects That Are Rescued by Nicotinamide and SIRT3 Activation." bioRxiv (2019): 713651).*

Scott et al.( Biochem. J. (2012) 443, 655-661).*

Salvatori, Illari, et al. "SIRT3 and mitochondrial metabolism in neurodegenerative diseases." Neurochemistry International 109 (2017): 184-192.*

Scott et al.("GCN5L1/BLOS1 links acetylation, organelle remodeling, and metabolism." Trends in cell biology 28.5 (2018): 346-355).*

Watts et al. ("Silencing disease genes in the laboratory and the clinic." The Journal of pathology 226.2 (2012): 365-379).*

Bagul, P.K., et al., "SIRT-3 Modulation by Resveratrol Improves Mitochondrial Oxidative Phosphorylation in Diabetic Heart through Deacetylation of TFAM", Cells 2018, 7, 235, 13 pages.

Beaucage, S. L., et al., "Advances in the Synthesis of Oligonucleotides by the Phosphoramidite Approach", ; Lyer, R. P. (1992). Tetrahedron 48 (12): 2223-2311.

Boulting GL, et al., "A functionally characterized test set of human induced pluripotent stem cells", Nat Biotechnol. 2011;29(3):279-86.

Egawa, N. et al. , "Drug screening for ALS using patient-specific Induced Pluripotent Stem Cells", *Sci Transl Med*, Aug. 1, 2012, vol. 4, pp. 145ra104: 1-8.

Eid, A., et al., "Genome editing: the road of CRISPR/Cas9 from bench to clinic", Exp Mol Med. (2016) 48(10): e265.

(Continued)

*Primary Examiner* — Kimberly Chong

(74) *Attorney, Agent, or Firm* — Hamilton, Brook, Smith & Reynolds, P.C.

(57) ABSTRACT

There is provided a method of promoting survival and/or function of an amyotrophic lateral sclerosis (ALS) or ALS-like motor, the method comprising contacting the motor neuron with an agent capable of reducing mitochondrial protein acetylation, particularly an agent selected from a deacetylase activator, such as nicotinamide (NAM) and 7-hydroxy-3-(4'-methoxyphenyl) coumarin (C12), or an acetyltransferase inhibitor, such as GCN5L1 siRNA of SEQ ID NO: 1. Also provided are related agents, oligonucleotides, uses and methods of identifying agents.

8 Claims, 45 Drawing Sheets

Specification includes a Sequence Listing.

(56) References Cited

OTHER PUBLICATIONS

Gold, L., et al., "Aptamer-Based Multiplexed Proteomic Technology for Biomarker Discovery", (2010) PLoS ONE 5(12):e15004).
Han, S. et al., Resveratrol upregulated heat shock proteins and extended the survival of G93A-SOD1 mice. *Brain Res*, Sep. 19, 2012, vol. 1483, pp. 112-117.
Hor JH, et al. "Cell cycle inhibitors protect motor neurons in an organoid model of Spinal Muscular Atrophy", Cell Death Dis. 2018;9(11):1100.
Hor, J.-H. et al., "ALS motor neurons exhibit hallmark metabolic defects that are rescued by Nicotinamide and SIRT3 activation", *BioRxiv*, Aug. 2, 2019, 32 pages.
Jafari R, , et al. "The cellular thermal shift assay for evaluating drug target interactions in cells", Nat Protoc. 2014;9(9):2100-22.
John et al, "Human MicroRNA Targets", PLoS Biology, 11(2), 1862-1879, 2004.
Kiskinis E, et al. "Pathways disrupted in human ALS motor neurons identified through genetic correction of mutant SOD1", Cell Stem Cell. 2014;14(6):781-95.
Lee BJ, et al., "Edaravone, a free radical scavenger, protects components of the neurovascular unit against oxidative stress in vitro", Brain Res. 2010;1307:22-7.
Lian X, et al. "Directed cardiomyocyte differentiation from human pluripotent stem cells by modulating Wnt/beta-catenin signaling under fully defined conditions", Nat Protoc. 2013;8(1):162-75.
Mahfouz et al., "Genome engineering via TALENs and CRISPR/Cas9 systems: challenges and perspectives", Plant Biotechnol J. (2014) 12(8):1006-1014.
Mancuso, R., et al., "Resveratrol Improves Motoneuron Function and Extends Survival in SOD1$^{G93A}$", Neurotherapeutics (2014) 11: 419-532.
Mordenti and Chappell, "The use of interspecies scaling in toxicokinetics" in Toxicokinetics and New Drug Development, Yacobi et al. (eds) (Pergamon Press: NY, 1989), pp. 42-96. (Abstract).
Mordenti et al., "Interspecies Scaling of Clearance and Volume of Distribution Data for Five Therapeutic Proteins", (1991) Pharmaceutical Research. 8(11):1351-1359.
Mordenti, J., et al., "Estimation and Permanence Time, Exit Time, Dilution Factor, and Steady-State Volume Distribution", Pharmaceutical Research 9(1): 17-25 (1992).
Mortensen, R., "Overview of gene targeting by homologous recombination", Curr Protoc Neurosci. (2007) Chapter 4:Unit 4.29 (abstract).
Moscou, M.J., et al., "A Simple Cipher Governs DNA Recognition by TAL Effectors", Science (2009) 326(5959):1501.
Muratore CR, et al., "Comparison and optimization of hiPSC forebrain cortical differentiation protocols", PLoS One. 2014;9(8):e105807.
Nakade, S., et al., "Cas9, Cpf1 and C2c1/2/3—What's next?", Bioengineered (2017) 8(3):265-273.
Ng SY, et al. "Genome-wide RNA-Seq of Human Motor Neurons Implicates Selective ER Stress Activation in Spinal Muscular Atrophy", *Cell Stem Cell*. 2015;17(5):569-584. doi:10.1016/j.stem.2015.08.003.
Notification of Transmittal of the International Search Report and the Written Opinion of the International Searching Authority, or the Declaration for International Application No. PCT/SG2020/050504, "A Method of Promoting Survival of a Motor Neuron and Related Agents, Uses and Methods" date of mailing: Nov. 16, 2020.
O'Keefe, E.P., "siRNAs and shRNAs: Tools for Protein Knockdown by Gene Silencing", Mater Methods (2013) 3:197.
Reverdatto, S., et al., "Peptide Aptamers: Development and Applications" Curr Top Med Chem. (2015) 15(12):1082-101.
Rodriguez-Muela N, et al. "Single-Cell Analysis of SMN Reveals Its Broader Role in Neuromuscular Disease", *Cell Rep*. 2017;18(6):1484-1498. doi:10.1016/j.celrep.2017.01.035.
Schindelin J, et al. "Fiji: an open-source platform for biological-image analysis", Nat Methods. 2012;9(7):676-682. Published Jun. 28, 2012. doi:10.1038/nmeth.2019.
Schondorf DC, et al. "The NAD+ Precursor Nicotinamide Riboside Rescues Mitochondrial Defects and Neuronal Loss in iPSC and Fly Models of Parkinson's Disease", Cell Rep. 2018;23(10):2976-88.
Scott, L, et al., "Identification of a molecular component of the mitochondrial acetyl transferase program; a novel role of GCN5L-1", Biochem J., May 1, 2012; 443(3): 655-661.
Sinha, N. D., et al., "Polymer support oligonucleotide synthesis SVIII[1,2]: use of β-cyanoethyl-N,N-dialkylamino-/N-morpholino phosphoramidite of deoxynucleosides for the synthesis of of DNA fragments simplifying deprotection and isolation of the final product", Nucleic Acids Res. 1984, 12(11): , 4539-4557.
Sperling S, et al., "Riluzole: a potential therapeutic intervention in human brain tumor stem-like cells", Oncotarget. 2017;8(57):96697-709.
Tuerk, C., et al., "Systematic Evolution of Ligands by Exponential Enrichment: RNA Ligands to Bacteriophage T4 DNA Polymerase", Science (1990) 249(4968):505-10.
Urnov, F.D., et al., "Genome editing with engineered zinc finger nucleases", mov et al., Nat Rev Genet. (2010) 11(9):636-46.
Vasquez et al., "Manipulating the mammalian genome by homologous recombination", PNAS (2001) 98(15): 8403-8410.
Zhou, J., et al., "Aptamers as targeted therapeutics: current potential and challenges", Nat Rev Drug Discov. 2017 16(3):181-202.
Harlan, B. A. et al: "Enhancing NAD+ Salvage Pathway Reverts the Toxicity of Primary Astrocytes Expressing Amyotrophic Lateral Sclerosis-linked Mutant Superoxide Dismutase 1 (SOD1 )", Journal of Biological Chemistry, vol. 291, No. 20, May 1, 2016 (May 1, 2016), pp. 10836-10846.
Choudhury, M. et al: "Knock down of GCN5 histone acetyltransferase by siRNA decreases ethanol-induced histone acetylation and affects differential expression of genes in human hepatoma cells", Alcohol, vol. 45, No. 4, Jun. 1, 2011 (Jun. 1, 2011), pp. 311-324.
Hor, Jin-Hui et al: "ALS motor neurons exhibit hallmark metabolic defects that are rescued by SIRT3 activation", Cell Death & Differentiation, vol. 28, No. 4, Nov. 12, 2020 (Nov. 12, 2020), pp. 1379-1397.
Supplementary Partial European Search Report for EP Application No. EP 20 85 7965, "A Method of Promoting Survival and/or Function of a Motor Neuron and Related Agents, Uses and Methods", dated Jul. 4, 2023.
Song, W., et al., Mutant SOD1G93A triggers mitochondrial fragmentation in spinal cord motor neurons: neuroprotection by SIRT3 and PGC-1α, Neurobiology of Disease, 2013年 , No. 51, p. 72-81, doi:10.1016/j.nbd.2012.07.004.
Lu, J. et al., A small molecule activator of SIRT3 promotes deacetylation and activation of manganese superoxide dismutase, Free Radical Biology & Medicine, 2017年 , vol. 112, p. 287-297, doi:10.1016/j.freeradbiomed.2017.07.012.
Webster, B. et al: "Restricted mitochondrial protein acetylation initiates mitochondrial autophagy", Journal of Cell Science, Jan. 1, 2013 (Jan. 1, 2013), 126, 4843-4849.
Supplementary European Search Report for EP Application No. EP 20 85 7965, "A Method of Promoting Survival and/or Function of a Motor Neuron and Related Agents, Uses and Methods", dated Nov. 21, 2023.
Salvatori, I., et al: "SIRT3 and mitochondrial metabolism in neurodegenerative diseases", Neurochemistry International, vol. 109, Apr. 25, 2017 (Apr. 25, 2017), pp. 184-192, XP085239577.
Choi Y-S., et al: "Shot-gun proteomic analysis of mitochondrial D-loop DNA binding proteins: identification of mitochondrial histones", Molecular Biosystems, vol. 7, No. 5, Jan. 1, 2011 (Jan. 1, 2011), p. 1523-1536, XP093100287.
Sharma, N., et al: "Mitochondrial DNA: Epigenetics and environment", Environmental and Molecular Mutagenesis, Wiley-Liss, Inc. Chichester, GB, vol. 60, No. 8, Aug. 6, 2019 (Aug. 6, 2019), pp. 668-682, XP071737071.
Scott Iain et al: "Identification of a molecular component of the mitochondrial acetyltransferase programme: a novel role for GCN5L1", Biochemical Journal, vol. 443, No. 3, Apr. 16, 2012 (Apr. 16, 2012), pp. 655-661, XP055796386.

* cited by examiner

METHOD OF PROMOTING SURVIVAL AND/OR FUNCTION OF A MOTOR NEURON AND RELATED AGENTS, USES AND METHODS

RELATED APPLICATIONS

This application is the U.S. National Stage of International Application No. PCT/SG2020/050504, filed Aug. 28, 2020, which designates the U.S., published in English, and claims priority under 35 U.S.C. § 119 or 365(c) to Singapore Application No. 10201908013X, filed Aug. 30, 2019. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:

a) File name: 5975.1008-001_Corrected_Sequence_Listing.txt; created Sep. 30, 2025, 14,469 Bytes in size.

TECHNICAL FIELD

The present disclosure relates broadly to a method of promoting survival and/or function of a motor neuron, such as an amyotrophic lateral sclerosis (ALS) or ALS-like motor neuron, and related agents, uses and methods.

BACKGROUND

Motor neuron diseases are a group of neurodegenerative diseases that affect the motor neurons. Among them, amyotrophic lateral sclerosis (ALS) is an age-onset, progressive neurodegenerative disorder affecting both upper and lower motor neurons (MNs).

In ALS, the loss of MNs leads to denervation of skeletal muscles resulting in stiff muscles and muscular atrophy and affects speech, swallowing, walking and breathing in patients. The disease progression is rapid and persistent, eventually leading to death. Riluzole and Edaravone, the only two FDA-approved therapeutics for ALS, are mildly efficacious. Riluzole was found to be efficacious amongst bulbar-onset ALS patients and not in subjects with limb-onset ALS, which constitutes most of the ALS patients. On average, Riluzole extends lifespan by 3 months while Edaravone showed efficacy only in a small subset of ALS patients. In spite of extensive research, an effective treatment has not yet been found, at least in part because of the poor understanding of the pathogenesis of ALS.

Majority of ALS cases (up to 90%) are sporadic, where the cause of disease is largely unknown. The rest of ALS patients have a familial form of the disease where mutations in genes such as SOD1, C9ORF72 and TDP43 are most common. Despite the genetic differences, the clinical manifestations of sporadic and familial ALS patients are indiscernible, suggesting a possible converging pathogenic mechanism. However, a common pathogenic node in both sporadic and familial ALS, which can potentially lay the path to novel ALS treatments for both ALS types, remains unidentified.

Thus, there is a need to provide an alternative method of promoting survival and/or function of a motor neuron in a motor neuron disease such as an amyotrophic lateral sclerosis (ALS) and the like, and related agents, uses and methods.

SUMMARY

In one aspect, there is provided a method of promoting survival and/or function of an amyotrophic lateral sclerosis (ALS) or ALS-like motor neuron, the method comprising contacting the motor neuron with an agent capable of reducing mitochondrial protein acetylation.

In one embodiment, the agent is selected from the group consisting of: a deacetylase activator, an acetyltransferase inhibitor and combinations thereof.

In one embodiment, the deacetylase activator comprises a SIRT3 (Sirtuin 3) activator.

In one embodiment, the SIRT3 activator is selected from the group consisting of: a small molecule, a NAD (nicotinamide adenine dinucleotide) or a precursor thereof, and combinations thereof.

In one embodiment, the small molecule is selected from the group consisting of: 7-hydroxy-3-(4'-methoxyphenyl) coumarin (C12), honokiol, dihydromyricetin (DHM) and derivatives, analogues and combinations thereof.

In one embodiment, the NAD precursor is selected from the group consisting of tryptophan, quinolinic acid, nicotinic acid (NA), nicotinamide (Nam), nicotinamide mononucleotide (NMN) nicotinamide riboside (NR), nicotinic acid and derivatives, analogues and combinations thereof.

In one embodiment, the acetyltransferase inhibitor comprises a GCN5L1 (GCN5 (general control of amino acid synthesis 5)-like 1) inhibitor.

In one embodiment, the GCN5L1 inhibitor comprises an oligonucleotide.

In one embodiment, the oligonucleotide is selected from the group consisting of: antisense oligonucleotide (ASO), gapmer, short interfering RNA (siRNA), short hairpin RNA (shRNA), microRNA (miRNA), guide RNA (gRNA), single guide RNA (sgRNA) and combinations thereof.

In one embodiment, the oligonucleotide comprises: a) a sequence that is complementary to a coding sequence (CDS) of BLOC1S1 gene or part thereof, or SEQ ID NO: 3 or part thereof, or SEQ ID NO: 4 or part thereof; or b) a sequence sharing at least about 75% sequence identity with the sequence in a).

In one embodiment, the oligonucleotide comprises a sequence sharing at least about 75% sequence identity with SEQ ID NO: 1, or a sequence differing from SEQ ID NO: 1 by about one nucleotide, about two nucleotides, about three nucleotides, about four nucleotides or about five nucleotides.

In one aspect, there is provided an agent capable of reducing mitochondrial protein acetylation for use in treating ALS or an ALS-like disease.

In one embodiment, the agent is selected from the group consisting of: a deacetylase activator, an acetyltransferase inhibitor and combinations thereof.

In one embodiment, the deacetylase activator comprises a SIRT3 activator, optionally wherein the SIRT3 activator is selected from the group consisting of: a small molecule, a NAD or a precursor thereof, and combinations thereof, optionally wherein the small molecule is selected from the group consisting of: C12, honokiol, dihydromyricetin (DHM) and derivatives, analogues and combinations thereof, optionally wherein the NAD precursor is selected from the group consisting of tryptophan, quinolinic acid, nicotinic acid (NA), nicotinamide (Nam), nicotinamide mononucleotide (NMN) nicotinamide riboside (NR), nicotinic acid and derivatives, analogues and combinations thereof.

In one embodiment, the acetyltransferase inhibitor comprises GCN5L1 inhibitor, optionally wherein the GCN5L1 inhibitor comprises an oligonucleotide, optionally wherein the oligonucleotide is selected from the group consisting of: antisense oligonucleotide (ASO), gapmer, short interfering RNA (siRNA), short hairpin RNA (shRNA), microRNA (miRNA), guide RNA (gRNA), single guide RNA (sgRNA) and combinations thereof, optionally wherein the oligonucleotide comprises: a) a sequence that is complementary to a CDS of BLOC1 S1 gene or part thereof, or SEQ ID NO: 3 or part thereof, or SEQ ID NO: 4 or part thereof; or a sequence sharing at least about 75% sequence identity with the sequence in a), optionally wherein the oligonucleotide comprises a sequence sharing at least about 75% sequence identity with SEQ ID NO: 1, or a sequence differing from SEQ ID NO: 1 by about one nucleotide, about two nucleotides, about three nucleotides, about four nucleotides or about five nucleotides.

In one aspect, there is provided use of the agent in the manufacture of a medicament for treating ALS or an ALS-like disease.

In one aspect, there is provided a method of treating ALS or an ALS-like disease in a subject, the method comprising administering to the subject the agent.

In one aspect, there is provided an oligonucleotide sharing at least about 75% sequence identity with SEQ ID NO: 1, or a sequence differing from SEQ ID NO: 1 by about one nucleotide, about two nucleotides, about three nucleotides, about four nucleotides or about five nucleotides.

In one aspect, there is provided the oligonucleotide for use in therapy.

In one aspect, there is a method of identifying an agent for treating ALS or an ALS-like disease, the method comprising: contacting an ALS or ALS-like motor neuron with a candidate agent; and determining whether mitochondrial protein acetylation in the motor neuron is reduced after the contact; and wherein where mitochondrial protein acetylation in the motor neuron is reduced after the contact, concluding that the candidate agent is an agent for treating ALS or an ALS-like disease, wherein where mitochondrial protein acetylation in the motor neuron is not reduced after the contact, concluding that the candidate agent is not an agent for treating ALS or an ALS-like disease, optionally wherein the agent for treating ALS or an ALS-like disease so identified comprises an agent or an oligonucleotide as described herein.

Definitions

The term "treatment", "treat" and "therapy", and synonyms thereof as used herein refer to both therapeutic treatment and prophylactic or preventative measures, wherein the object is to prevent, slow down (lessen) or reverse a medical condition, which includes but is not limited to diseases (such as degenerative diseases and/or motor neuron diseases), symptoms and disorders. A medical condition also includes a body's response to a disease or disorder, e.g. inflammation. Those in need of such treatment include those already with a medical condition as well as those prone to getting the medical condition or those in whom a medical condition is to be prevented.

As used herein, the term "therapeutically effective amount" will be an amount of an active agent that is capable of preventing, reversing or at least slowing down (lessening) a medical condition, such as motor neuron diseases, autoimmune diseases, inflammation and cancer. Dosages and administration of agents, compounds, compositions and formulations of the present disclosure may be determined by one of ordinary skill in the art of clinical pharmacology or pharmacokinetics. See, for example, Mordenti and Rescigno, (1992) Pharmaceutical Research. 9:17-25; Morenti et al., (1991) Pharmaceutical Research. 8:1351-1359; and Mordenti and Chappell, "The use of interspecies scaling in toxicokinetics" in Toxicokinetics and New Drug Development, Yacobi et al. (eds) (Pergamon Press: NY, 1989), pp. 42-96. An effective amount of the active agent of the present disclosure to be employed therapeutically will depend, for example, upon the therapeutic objectives, the route of administration, and the condition of the subject. Accordingly, it may be necessary for the therapist to titer the dosage and modify the route of administration as required to obtain the optimal therapeutic effect.

The term "subject" as used herein includes patients and non-patients. The term "patient" refers to individuals suffering or are likely to suffer from a medical condition such as a motor neuron disease, while "non-patients" refer to individuals not suffering and are likely to not suffer from the medical condition. "Non-patients" include healthy individuals, non-diseased individuals and/or an individual free from the medical condition. The term "subject" includes humans and animals. Animals include murine and the like. "Murine" refers to any mammal from the family Muridae, such as mouse, rat, and the like.

The term "micro" as used herein is to be interpreted broadly to include dimensions from about 1 micron to about 1000 microns.

The term "nano" as used herein is to be interpreted broadly to include dimensions less than about 1000 nm.

The term "particle" as used herein broadly refers to a discrete entity or a discrete body. The particle described herein can include an organic, an inorganic or a biological particle. The particle used described herein may also be a macro-particle that is formed by an aggregate of a plurality of sub-particles or a fragment of a small object. The particle of the present disclosure may be spherical, substantially spherical, or non-spherical, such as irregularly shaped particles or ellipsoidally shaped particles. The term "size" when used to refer to the particle broadly refers to the largest dimension of the particle. For example, when the particle is substantially spherical, the term "size" can refer to the diameter of the particle; or when the particle is substantially non-spherical, the term "size" can refer to the largest length of the particle.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. It is to be appreciated that the individual numerical values within the range also include integers, fractions and decimals. Furthermore, whenever a range has been described, it is also intended that the range covers and teaches values of up to 2 additional decimal places or significant figures (where appropriate) from the shown numerical end points. For example, a description of a range of 1% to 5% is intended to have specifically disclosed the ranges 1.00% to 5.00% and also 1.0% to 5.0% and all their intermediate values (such as 1.01%, 1.02% . . . 4.98%, 4.99%, 5.00% and 1.1%, 1.2% . . . 4.8%, 4.9%, 5.0% etc.,) spanning the ranges. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a method of promoting survival and/or function of motor neurons, and related methods, uses, agents and compositions are disclosed hereinafter.

In various embodiments, there is provided a method of promoting survival and/or function of motor neurons, the method comprising modulating/regulating acetylation of a mitochondrial product in the motor neurons. In some embodiments, the method is a method of promoting survival of motor neurons. Embodiments of the method may increase viability of cells/motor neurons and/or reduce cell loss/motor neuron loss. In some embodiments, the method is a method of promoting/improving function, optionally a metabolic function, of motor neurons. Embodiments of the method may restore, at least to a certain extent, a proper function, optionally a metabolic function and/or mitochondrial function, in motor neurons. For example, embodiments of the method may restore a proper function, optionally a metabolic and/or mitochondrial function, in motor neurons such that the function resembles or more closely resembles that in a healthy/normal motor neuron. In some embodiments, modulating/regulating acetylation of a mitochondrial product comprises reducing/inhibiting acetylation of a mitochondrial product. In some embodiments, the mitochondrial product comprises a mitochondrial protein. Without being bound by theory, it is believed that increased acetylation or hyper-acetylation of mitochondrial product e.g. mitochondrial protein in motor neurons lead to defective metabolism or defective mitochondrial respiration in the motor neurons, resulting in their deaths. Hyper-acetylation of mitochondrial product e.g. mitochondrial protein may be observed in certain motor neuron diseases, such as amyotrophic lateral sclerosis.

In various embodiments therefore, there is provided a method of promoting survival and/or function of motor neurons in a motor neuron disease, the method comprising reducing/inhibiting mitochondrial protein acetylation in the motor neurons. Examples of a motor neuron disease include amyotrophic lateral sclerosis, primary lateral sclerosis, progressive bulbar palsy, pseudobulbar palsy, progressive muscular atrophy, spinal muscular atrophy, Kennedy's disease, and post-polio syndrome. In one embodiment, the motor neuron disease comprises amyotrophic lateral sclerosis (ALS) or an ALS-like disease. An ALS-like disease may be a disease that has or that is characterised by increased/excessive acetylation or hyper-acetylation of mitochondrial protein in motor neurons resulting in defective metabolism and motor neuron deaths. An ALS-like disease may be identified, for example, by measuring a level/relative level of mitochondrial protein acetylation in a diseased motor neuron and comparing the level of acetylation with that of a control motor neuron e.g. a non-diseased motor neuron or a healthy motor neuron, wherein where the diseased motor neuron shows an increased/elevated level/relative level of acetylation as compared to that of the control motor neuron, the disease may be classified as or taken to be an ALS-like disease. Thus, in some embodiments, the method may further comprise a step of measuring/determining mitochondrial protein acetylation in the motor neuron. Where the motor neuron is measured/determined to have an increased/elevated level/relative level of acetylation compared to that of the control motor neuron, mitochondrial protein acetylation in the motor neuron may then be reduced or inhibited to promote survival and/or function of the motor neuron.

In various embodiments, reducing mitochondrial protein acetylation in a motor neuron comprises reducing an amount/fraction/percentage of acetylated mitochondrial proteins in the motor neuron and/or reducing a degree of acetylation (e.g. a number of acetylated sites) within a mitochondrial protein in the motor neuron. In some embodiments, the acetylation comprises a lysine acetylation. In various embodiments, the reduction may be at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100%. In some embodiments, the reduction is at least about 25%. In various examples, the degree of reduction in mitochondrial protein acetylation achieved by agents such as nicotinamide (Nam), 7-hydroxy-3-(4'-methoxyphenyl) coumarin (C12) and GCN5L1 siRNA is at least about 25%.

In various embodiments, mitochondrial protein acetylation in a motor neuron may be reduced by contacting the motor neuron with an agent. The agent may reduce an amount/fraction/percentage of acetylated mitochondrial proteins in a motor neuron and/or it may reduce a degree of acetylation within a mitochondrial protein in a motor neuron. An "agent" may be anything (physical, chemical, biological etc.) that a motor neuron may be exposed to e.g. in order to reduce mitochondrial protein acetylation in the motor neuron. Non-limiting examples of an "agent" include chemicals, compounds, compositions molecules, small molecules, nucleic acid sequences, nucleic acid analogues, proteins, peptides, aptamers, antibodies, or fragments thereof. The term "agent" in no way excludes the use of two or more such agents. Accordingly, the term "agent" also contemplates mixtures, fusions, combinations, compositions and conjugates, for example, mixtures, fusions, combinations, compositions and conjugates of any chemicals, compounds, compositions, molecules, small molecules, nucleic acid sequences, nucleic acid analogues, proteins, peptides, aptamers, antibodies, or fragments thereof etc.

A nucleic acid sequence can be RNA and/or DNA, and can be single or double stranded. In one example, a nucleic acid sequence comprises an oligonucleotide. A nucleic acid sequence may be composed of natural bases, chemically modified bases, artificial bases, nucleotide analogues and combinations thereof. A nucleic acid sequence may also comprise modification(s) to its ribose or sugar moiety, and/or modification(s) to its phosphate linkage part or phosphodiester linkage. An example of ribose or sugar modification comprises modification to the 2' position of the ribose ring such as 2'-amino, 2'-fluoro, 2'-O-methyl and 2'-O-methoxy-ethyl. Non-limiting examples of a modified phosphate linkage part or phosphodiester linkage include a phosphorothioate linkage, a boranophosphate linkage, a methylphophonate, a phosphorthioate analogue, replacement to triazole linkage and the like. In one example, the nucleic acid sequence comprises phosphoramidite nucleotide.

Non-limiting examples of nucleic acid analogues include peptide nucleic acid (PNA), pseudo-complementary PNA (pc-PNA), locked nucleic acid (LNA), morpholino nucleotide, threose nucleic acid (TNA), glycol nucleic acid (GNA), arabinose nucleic acid (ANA), 2'-deoxy-2'-fluoro-β-D-arabinonucleic acid (2' F-ANA), 2'-fluoroarabinose nucleic acid (FANA), 2'-deoxy-2'-fluororibonucleic acid (2'-F RNA or FRNA) cyclohexene nucleic acid (CeNA), anhydrohexitol nucleic acid (HNA), unlocked nucleic acid (UNA), ethylene-bridged nucleic acids (ENA), (4'-6') linked oligo 2',3'-dideoxy-β-D-glucopyranose nucleic acid (homo-DNA or hDNA), xylonucleic acid (XyNA), deoxy-xylonucleic acids (dXyNA), aminoallyl uridine (aa-UTP), N3'→P5'-phosphoramidate (NP), tricyclo-DNA (tcDNA), phosphorodiamidate morpholino (PMO), derivatives thereof and the like.

Non-limiting examples of proteins include mutated proteins, genetically engineered proteins, peptides, synthetic peptides, recombinant proteins, chimeric proteins, antibodies, humanized proteins, modified proteins and fragments thereof (e.g. an antigen-binding fragment). As used herein, the term "antibody" refers to an immunoglobulin or fragment thereof, and encompasses any polypeptide comprising an antigen-binding fragment or an antigen-binding domain. The term includes but is not limited to polyclonal, monoclonal, monospecific, polyspecific (such as bi-specific), humanized, human, single-chain, chimeric, synthetic, recombinant, hybrid, mutated, grafted, and in vitro generated antibodies. The term "antibody" may include antibody fragments such as Fab, F(ab')2, Fv, scFv, Fd, dAb, and other antibody fragments that retain antigen-binding function. An antibody is not necessarily from any particular source, nor is it produced by any particular method.

In various embodiments, the motor neuron may be naturally occurring or non-naturally occurring/engineered (e.g. an iPSC-derived motor neuron). Typically, motor neurons include upper motor neurons and lower motor neurons.

In various embodiments therefore, there is provided a method of promoting survival and/or function of an ALS or ALS-like motor neuron, the method comprising contacting the motor neuron with an agent capable of reducing mitochondrial protein acetylation.

In various embodiments, an ALS or ALS-like motor neuron has or is characterised by increased/excessive acetylation or hyper-acetylation of mitochondrial protein. In various examples, the acetylation level of mitochondrial proteins or the expression/signal of acetylated mitochondrial proteins (e.g. acetyl-lysine proteins or acetyl-lysine 68 on manganese superoxide dismutase (MnSOD K68ac)) in an ALS or ALS-like motor neuron is more than about 1 times e.g. at least about 1.05 times, at least about 1.1 times, at least about 1.15 times, at least about 1.2 times, at least about 1.25 times, at least about 1.3 times, at least about 1.35 times, at least about 1.4 times, at least about 1.45 times, at least about 1.5 times, at least about 1.55 times, at least about 1.6 times, at least about 1.65 times, at least about 1.7 times, at least about 1.75 times, at least about 1.8 times, at least about 1.85 times, at least about 1.9 times, at least about 2 times, at least about 2.5 times, at least about 3 times, at least about 3.5 times, at least about 4 times, at least about 4.5 times, at least about 5 times, at least about 5.5 times, at least about 6 times, at least about 6.5 times, at least about 7 times, at least about 7.5 times, at least about 8 times, at least about 8.5 times, at least about 9 times at least about 9.5 times or at least about 10 times that in a control/healthy motor neuron (e.g. a non-ALS motor neuron or a non-ALS-like motor neuron). In various embodiments, an ALS or ALS-like motor neuron comprises one or more of the following properties: mutation in one or more genes selected from SOD1 (e.g. G93A, A4V, L144F etc.), TDP43 (e.g. G298S), C9ORF72 (e.g. expanded GGGGCC repeats) and others such as FUS, HNRNPA1, VAPB etc, mitochondrial dysfunction, metabolic respiration defect, altered morphology as compared to a control/healthy motor neuron, an abnormal mitochondria morphology as compared to the mitochondria of a control/healthy motor neuron, accelerated death phenotype relative to a control/healthy motor neuron, reduced basal survival relative to a control/healthy motor neuron, elevated endoplasmic reticulum (ER) stress relative to a control/healthy motor neuron, upregulation/increased expression of CHOP gene relative to a control/healthy motor neuron, upregulation/increased expression of spliced XBP1 (sXBP1) relative to a control/healthy motor neuron, reduced basal respiration relative to a control/healthy motor neuron, decreased ATP-linked oxygen consumption rate (OCR) relative to a control/healthy motor neuron, reduced ATP production relative to a control/healthy motor neuron, decreased spare respiratory capacity relative to a control/healthy motor neuron, increased extracellular acidification rate (ECAR) relative to a control/healthy motor neuron, increased glycolysis relative to a control/healthy motor neuron, increased glycolytic capacity relative to a control/healthy motor neuron, reduced/impaired oxidative phosphorylation relative to a control/healthy motor neuron, reduced deacetylase expression and/or activity (e.g. sirtuin such as SIRT3) relative to a control/healthy motor neuron, reduced Complex I activity relative to a control/healthy motor neuron, reduced mitochondrial $NAD^+$ levels (e.g. at least about 30%, at least about 40%, at least about 50%, at least about 60%, at least about 70% or at least about 80% reduction) relative to a control/healthy motor neuron, elevated/increased mitophagy relative to a control/healthy motor neuron, reduced soma size relative to a control/healthy motor neuron, reduced primary neurites relative to a control/healthy motor neuron and hyperexcitability relative to a control/healthy motor neuron. In some embodiments, the change (e.g. increase or decrease) in the one or more of the above properties (e.g. expression of a gene, basal survival, ATP production, spare respiratory capacity etc.) in an ALS or ALS-like motor neuron relative to that in a control/healthy motor neuron is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100%. In some embodiments, the change is at least about 0.1 times, at least about 0.2 times, at least about 0.3 times, at least about 0.4 times, at least about 0.5 times, at least about 0.6 times, at least about 0.7 times, at least about 0.8 times or at least about 0.9 times. In some embodiments, the change is more than about 1 times e.g. at least about 1.05 times, at least about 1.1 times, at least about 1.15 times, at least about 1.2 times, at least about 1.25 times, at least about 1.3 times, at least about 1.35 times, at least about 1.4 times, at least about 1.45 times, at least about 1.5 times, at least about 1.55 times, at least about 1.6 times, at least about 1.65 times, at least about 1.7 times, at least about 1.75 times, at least about 1.8 times, at least about 1.85 times, at least about 1.9 times, at least about 2 times, at least about 2.5 times, at least about 3 times, at least about 3.5 times, at least about 4 times, at least about 4.5 times, at least about 5 times, at least about 5.5 times, at least about 6 times, at least about 6.5 times, at least about 7 times, at least about 7.5 times, at least about 8 times, at least about 8.5 times, at least about 9 times at least about 9.5 times or at least about 10 times. In one embodiment, an ALS or ALS-like motor neuron does not show a differential expression, a substantially elevated expression or a substantially reduced expression of SIRT3 as compared to a control/healthy motor neuron. In one embodiment, SIRT3 expression in an ALS or ALS-like motor neuron is substantially similar or comparable to the SIRT3 expression in a control/healthy motor neuron.

In various embodiments, the ALS may be sporadic ALS and/or familial ALS.

In various embodiments, the mitochondrial protein comprises a protein, or a subunit thereof, that is capable of localizing to the mitochondria of a motor neuron. In some embodiments, the mitochondrial protein comprises a protein, or a subunit thereof, that is synthesized in the mitochondria from mitochondrial DNA (or mitochondria-encoded). In some embodiments, the mitochondrial protein comprises a protein, or a subunit thereof, synthesized outside of the mitochondria which is imported into the mitochondria. The term “protein” includes any chain of amino acids such as protein, peptide, polypeptide and conjugated proteins such as glycoproteins, lipoproteins, phosphoproteins, metalloproteins, cytochromes and the like. In some embodiments, the mitochondrial protein comprises an enzyme. In some embodiments, the mitochondrial protein comprises a metabolic enzyme. In some embodiments, the mitochondrial protein comprises an antioxidant enzyme. In some embodiments, the mitochondrial protein is involved in one or more of the following pathways: cell death, oxidative phosphorylation, generation of energy, fatty acid metabolism, sugar metabolism and amino acid metabolism. In some embodiments, the mitochondrial protein interacts with or is a target (e.g. direct or indirect downstream target) of a deacetylase, optionally a sirtuin, optionally SIRT3. In some embodiments, the mitochondrial protein interacts with or is a target (e.g. direct or indirect downstream target) of an acetyltransferase, optionally GCN5L1 (GCN5 (general control of amino acid synthesis 5)-like 1). In some embodiments, the mitochondrial protein comprises manganese superoxide dismutase (MnSOD). In some embodiments, the mitochondrial protein acetylation comprises lysine acetylation. In some embodiments, the mitochondrial protein acetylation comprises acetylation of lysine 68 on manganese superoxide dismutase (MnSOD K68ac). In various examples, microarray/gene expression analysis performed on healthy and sporadic ALS iPSC-derived motor neurons revealed an overrepresentation of one or more of the above pathways. The in silico associative predictions may indicate that defective mitochondria contribute to sporadic ALS pathogenesis.

In various embodiments, reducing/inhibiting mitochondrial protein acetylation comprises increasing an expression and/or an activity of a deacetylase. In some embodiments, reducing/inhibiting mitochondrial protein acetylation does not comprise increasing an expression of a deacetylase or solely increasing an expression of a deacetylase e.g. without an increase or a concomitant increase in an activity of the deacetylase. In various embodiments, reducing/inhibiting mitochondrial product acetylation comprises reducing/inhibiting an expression and/or an activity of an acetyltransferase. In various embodiments therefore, the agent is selected from the group consisting of: a deacetylase activator or agonist, an acetyltransferase inhibitor or antagonist and combinations thereof.

In some embodiments, the deacetylase comprises a mitochondria-enriched deacetylase. In some embodiments, the deacetylase comprises a major mitochondria deacetylase. In some embodiments, inducing or increasing an activity of the deacetylase in an ALS or ALS-like motor neuron rescues disease phenotype and/or metabolic defects. In some embodiments, the deacetylase comprises a $NAD^+$-dependent deacetylase. In some embodiments, the deacetylase comprises a protein from the sirtuin family. The sirtuin family may comprise SIRT1, SIRT2, SIRT3, SIRT4, SIRT5, SIRT6 and SIRT7, which may be assigned to five subclasses (I, II, III, IV and U). In some embodiments, the deacetylase comprises a mitochondrial sirtuin. In some embodiments, the mitochondrial sirtuin is selected from the group consisting of: SIRT3, SIRT4, SIRT5 and combinations thereof. In one embodiment, the deacetylase comprises SIRT3. In various examples, SIRT3 levels in ALS mice were compared against SIRT3 levels in healthy mice, and SIRT3 levels in human healthy spinal cords were compared against SIRT3 levels in ALS post-mortem spinal cords. In the examples, in humans, increased SIRT3 mRNA and proteins were found in ALS spinal cords. Since SIRT3 is an enzyme, its activity may be more informative than just its expression levels alone. In various examples, similar SIRT3 protein levels were found in ALS iPSC-derived motor neurons, even though SIRT3 activity was very much reduced. In various examples, loss of SIRT3 function results in ALS phenotypes.

In various embodiments therefore, the deacetylase activator comprises a SIRT3 activator. The SIRT3 activator may promote deacetylation of targets downstream of SIRT3. In some embodiments, the SIRT3 activator may promote deacetylation of mitochondrial proteins. In some embodiments, the SIRT3 activator may promote deacetylation of manganese superoxide dismutase (MnSOD). In some embodiments, SIRT3 activator may promote deacetylation of lysine 68 on manganese superoxide dismutase (MnSOD K68ac). In various embodiments, the SIRT3 activator may reduce the level of acetylation of mitochondrial proteins, MnSOD and/or MnSOD K68ac. In various embodiments, the reduction is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100%.

In some embodiments, the SIRT3 activator comprises a cofactor and/or cosubstrate of SIRT3. In some embodiments, the SIRT3 activator comprises $NAD^+$ and/or a $NAD^+$ precursor, or analogues, derivatives and combinations thereof. In various embodiments, the $NAD^+$ precursor is selected from the group consisting of tryptophan, quinolinic acid, nicotinic acid (NA), nicotinamide (Nam), nicotinamide mononucleotide (NMN) nicotinamide riboside (NR), nicotinic acid and derivatives, analogues and combinations thereof. In some embodiments, the $NAD^+$ precursor comprises vitamin B3 or niacin, or analogues, derivatives and combinations thereof. In some embodiments, the vitamin B3 or niacin is selected from the group consisting of NA, Nam, NR and combinations thereof. In some embodiments, the method comprises contacting the motor neuron with food, e.g. food for medical purposes, capable of reducing mitochondrial protein acetylation. Examples of food include health food, food additives, food supplements, dietary supplements, nutritional supplements, nutrients, vitamins, and/or nutraceuticals. In various examples, increasing NAD+ levels in ALS astrocytes reduces astrocyte-mediated toxicity in a co-culture model of astrocytes and motor neurons.

In various embodiments, the SIRT3 activator, $NAD^+$ or $NAD^+$ precursor is capable of increasing the $NAD^+$ level in a mitochondrion of a motor neuron by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100%. In various embodiments, the SIRT3 activator, $NAD^+$ or $NAD^+$ precursor is capable of increasing the $NAD^+$ level in a mitochondrion of a motor neuron to more than about 1 times e.g. at least about 1.05 times, at least about 1.1 times, at least about 1.15 times, at least about 1.2 times, at least about 1.25 times, at least about 1.3 times, at least about 1.35 times, at least about 1.4 times, at least about 1.45 times, at least about 1.5 times, at least about 1.55 times, at least about 1.6 times, at least about 1.65 times, at least about 1.7 times, at least about 1.75 times, at least about 1.8 times, at least about 1.85 times, at least about 1.9 times, at least about 2 times, at least about 2.5 times, at least about 3 times, at least about 3.5 times, at least about 4 times, at least about 4.5 times, at least about 5 times, at least about 5.5 times, at least about 6 times, at least about 6.5 times, at least about 7 times, at least about 7.5 times, at least about 8 times, at least about 8.5 times, at least about 9 times at least about 9.5 times or at least about 10 times.

In various embodiments, the concentration of the SIRT3 activator, $NAD^+$ or $NAD^+$ precursor is from about 0.01 mM to about 10 mM, from about 0.05 mM to about 5 mM, from about 0.07 mM to about 3 mM, from about 0.08 mM to about 2 mM, from about 0.1 mM to about 1 mM, from about 0.2 mM to about 0.8 mM, from about 0.3 mM to about 0.7 mM or from about 0.4 mM to about 0.6 mM. In various embodiments, the concentration of the SIRT3 activator, $NAD^+$ or $NAD^+$ precursor is no more than about 10 mM, no more than about 9 mM, no more than about 8 mM, no more than about 7 mM, no more than about 6 mM, no more than about 5 mM, no more than about 4 mM, no more than about 3 mM, no more than about 2 mM, no more than about 1 mM, no more than about 0.9 mM, no more than about 0.8 mM, no more than about 0.7 mM, no more than about 0.6 mM or no more than about 0.5 mM. In various embodiments, the concentration the concentration of the SIRT3 activator, $NAD^+$ or $NAD^+$ precursor is at least about 0.01 mM, at least about 0.05 mM, at least about 0.1 mM, at least about 0.15 mM, at least about 0.2 mM, at least about 0.25 mM, at least about 0.3 mM, at least about 0.35 mM, at least about 0.4 mM, at least about 0.45 mM or at least about 0.5 mM. In one embodiment, the concentration of the SIRT3 activator or $NAD^+$ precursor is about 0.5 mM. The concentration/dose/amount of the concentration of the SIRT3 activator, $NAD^+$ or $NAD^+$ precursor may be further varied so as to achieve the desired response for a particular motor neuron, patient, composition, and mode of administration, with no or minimal toxicity to the cell or patient. In various embodiments, the concentration of the SIRT3 activator, $NAD^+$ or $NAD^+$ precursor is less than the concentration that causes toxicity e.g. cell or liver toxicity. In various embodiments, the concentration of the concentration of the SIRT3 activator, $NAD^+$ or $NAD^+$ precursor causes substantially no toxicity or minimal toxicity e.g. cell or liver toxicity. In various embodiments, where the concentration/dose/amount of the SIRT3 activator, $NAD^+$ or $NAD^+$ precursor required to reduce the level of acetylation of mitochondrial protein by a desired amount may result in toxicity e.g. cell or liver toxicity, the SIRT3 activator or $NAD^+$ precursor may be used at a lower concentration/dose/amount in combination with a second/further agent e.g. a different SIRT3 activator and/or GCN5L1 inhibitor to achieve the desired amount of reduction in the level of acetylation. In various embodiments, the second/further agent does not substantially affect the $NAD^+$ level in a mitochondrion of a motor neuron. In various embodiments, the second/further agent does not comprise tryptophan, quinolinic acid, nicotinic acid (NA), nicotinamide (Nam), nicotinamide mononucleotide (NMN) nicotinamide riboside (NR), nicotinic acid, or derivatives or analogues thereof. In some embodiments, the second/further agent comprises a GCN5L1 inhibitor. In some embodiments, the agent or SIRT3 activator does not comprise/consist of vitamin B3 or niacin or food e.g. as the sole/only agent for activating SIRT3 or reducing mitochondrial protein acetylation.

In various embodiments, the SIRT3 activator is capable of binding to SIRT3 e.g. an active site of SIRT3. In various embodiments, the SIRT3 activator has binding affinity e.g. a high binding affinity for SIRT3. In various embodiments, the SIRT3 activator is capable of changing the conformation of an active site on SIRT3. In various embodiments, the SIRT3 activator is specific to SIRT3. For example, embodiments of the SIRT3 activator are incapable of activating and/or binding to another sirtuin e.g. SIRT1, SIRT2, SIRT4, SIRT5, SIRT6 and/or SIRT7. In some embodiments, the SIRT3 activator has a low molecular weight. In some embodiments, the SIRT3 activator is no more than about 1500 Daltons (Da), no more than about 1400 Da, no more than about 1300 Da, no more than about 1200 Da, no more than about 1100 Da, no more than about 1000 Da, no more than about 900 Da, no more than about 800 Da, no more than about 700 Da, no more than about 600 Da, no more than about 500 Da, no more than about 400 Da, no more than about 300 Da, no more than about 200 Da, no more than about 100 Da or no more than about 50 Da. In some embodiments, the SIRT3 activator comprises a small molecule. The small molecule may comprise an organic compound. The small molecule may be a natural compound (e.g. a plant-based compound) and/or a chemically synthesised/artificial compound. The small molecule may be a flavonoid, optionally a flavanonol. In some embodiments, the small molecule comprises a small-molecule polyphenol. In some embodiments, the small molecule is selected from the group consisting of: 7-hydroxy-3-(4'-methoxyphenyl) coumarin (C12), honokiol, dihydromyricetin (DHM) and derivatives, analogues and combinations thereof. In some embodiments, the small molecule comprises the chemical structure:

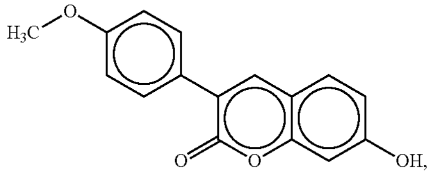

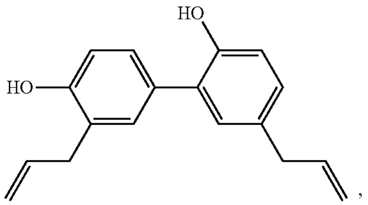

-continued

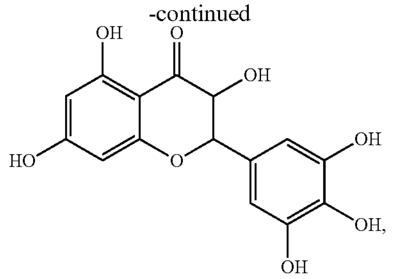

or derivatives, analogues or combinations thereof

As used herein, the term "derivative", "analogue" or "functional analogue" of a parent molecule refers to a molecule that is structurally related to the parent molecule. For example, a derivative, analogue or functional analogue of a parent molecule may share a common structural feature, fundamental structure and/or underlying chemical basis with the parent molecule. A derivative is not limited to one produced or obtained from the parent molecule although it may be one produced or obtained from the parent molecule. In some embodiments, a derivative is derivable, at least theoretically, from the parent molecule through modification of the parent molecule. The term "derivative" also includes conjugates, salts, metabolites, and prodrugs (e.g. modified derivatives which can be converted into the original compound under physiological conditions) of a parent molecule. On the other hand, in some embodiments, an analogue or functional analogue may not necessarily be produced or obtained using the parent molecule as a starting material. In various embodiments, a derivative, analogue or functional analogue of a parent molecule shares or at least retains to a certain extent a function, chemical property, biological property, chemical activity and/or biological activity associated with the parent molecule. A skilled person will be able to identify, on a case by case basis and upon reading of the disclosure, the common structural feature, fundamental structure and/or underlying chemical basis of the molecule that have to be maintained in the derivative, analogue or functional analogue to retain the function, chemical property, biological property, chemical activity, and/or biological activity. A skilled person will also be able to identify assays that can prove the retention of the function, chemical property, biological property, chemical activity and/or biological activity. For example, assays such as cellular thermal shift assay (CETSA), sodium dodecyl sulphate-polyacrylamide gel electrophoresis (SDS-PAGE) analysis, western blot analysis, metabolic flux analysis MitoStress Assay, motor neuron survival assay, enzyme-linked immunosorbent assay (ELISA), electrophoretic mobility shift assay (EMSA), surface plasmon resonance (SPR), bio-layer interferometry (BLI) and the like may be carried out to determine a function, chemical property, biological property, chemical activity and/or biological activity of a molecule.

In various embodiments, the concentration of the SIRT3 activator or small molecule or derivative or analogue is from about 0.1 μM to about 100 μM, from about 0.5 μM to about 50 μM, from about 1 μM to about 30 μM, from about 5 μM to about 15 μM, from about 1 μM to about 10 μM, from about 2 μM to about 8 μM or from about 3 μM to about 7 μM. In various embodiments, the concentration of the SIRT3 activator or small molecule or derivative or analogue is no more than about 100 μM, no more than about 50 μM, no more than about 30 μM, no more than about 15 μM, no more than about 10 μM, no more than about 9 μM, no more than about 8 μM, no more than about 7 μM, no more than about 6 μM or no more than about 5 μM. In various embodiments, the concentration of the SIRT3 activator or small molecule or derivative or analogue is at least about 0.1 μM, at least about 0.5 μM, at least about 1 μM, at least about 1.5 μM, at least about 2 μM, at least about 2.5 μM, at least about 3 μM, at least about 3.5 μM, at least about 4 μM, at least about 4.5 μM, at least about 5 μM, at least about 5.5 μM, at least about 6 μM, at least about 6.5 μM, at least about 7 μM, at least about 7.5 μM, at least about 8 μM, at least about 8.5 μM, at least about 9 μM, at least about 9.5 μM or at least about 10 μM. In one embodiment, the concentration of the SIRT3 activator or small molecule or derivative or analogue is about 5 μM. In one embodiment, the concentration of the SIRT3 activator or small molecule or derivative or analogue less than about 10 μM. The concentration/dose/amount of the SIRT3 activator or small molecule or derivative or analogue may be further varied so as to achieve the desired response for a particular motor neuron, patient, composition, SIRT3 activator, small molecule and mode of administration, with no or minimal toxicity to the cell or patient. In various embodiments, the concentration of the SIRT3 activator or small molecule or derivative or analogue is less than the concentration that causes toxicity to the cell or patient.

In some embodiments, the deacetylase activator increases/is capable of increasing an activity of a deacetylase. In some embodiments, the deacetylase activator does not increase/is incapable of increasing an expression or an expression level of the deacetylase.

In some embodiments, the acetyltransferase comprises a mitochondria-enriched acetyltransferase. In some embodiments, the acetyltransferase counters the acetylation and/or respiratory effects of a deacetylase e.g. SIRT3. In some embodiments, knockdown or depletion of the acetyltransferase in an ALS or ALS-like motor neuron rescues disease phenotype and/or metabolic defects. In some embodiments, the acetyltransferase comprises a protein having sequence homology to and/or loose sequence alignment with the nuclear acetyl transferase general control of amino acid synthesis 5 (GCN5). In some embodiments, the acetyltransferase comprises general control of amino acid synthesis 5-like 1 (GCN5L1), also known as biogenesis of lysosome-related organelles complex 1 subunit 1 (BLOC1S1).

In various embodiments therefore, the acetyltransferase inhibitor comprises a GCN5L1 inhibitor. In some embodiments, the GCN5L1 inhibitor may reduce/inhibit acetylation of mitochondrial proteins. In some embodiments, the GCN5L1 inhibitor may reduce/inhibit acetylation of manganese superoxide dismutase (MnSOD). In some embodiments, the GCN5L1 inhibitor may reduce/inhibit acetylation of lysine 68 on manganese superoxide dismutase (MnSOD K68ac). In various embodiments, the GCN5L1 inhibitor may reduce the level of acetylation of mitochondrial proteins, MnSOD and/or MnSOD K68ac. In various embodiments, the reduction is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100%.

In some embodiments, the acetyltransferase inhibitor comprises a chemical i.e. a chemical inhibitor. The chemical compound may comprise an organic or inorganic compound. In some embodiments, the chemical inhibitor comprises a small molecule. In some embodiments, the acetyltransferase inhibitor comprises a nucleic acid sequence. In some embodiments, the acetyltransferase inhibitor comprises no more than about 200 nucleotides/bases, no more than about 190 nucleotides/bases, no more than about 180 nucleotides/bases, no more than about 170 nucleotides/bases, no more than about 160 nucleotides/bases, no more than about 150 nucleotides/bases, no more than about 140 nucleotides/bases, no more than about 130 nucleotides/bases, no more than about 120 nucleotides/bases, no more than about 110 nucleotides/bases, no more than about 100 nucleotides/bases, no more than about 90 nucleotides/bases, no more than about 80 nucleotides/bases, no more than about 70 nucleotides/bases, no more than about 60 nucleotides/bases, no more than about 50 nucleotides/bases, no more than about 40 nucleotides/bases, no more than about 30 nucleotides/bases, no more than about 20 nucleotides/bases or no more than about 10 nucleotides/bases. In some embodiments, the acetyltransferase comprises from about 10 to about 200 nucleotides/bases, from about 10 to about 150 nucleotides/bases, from about 10 to about 100 nucleotides/bases, from about 10 to about 50 nucleotides/bases, from about 10 to about 40 nucleotides/bases, from about 10 to about 30 nucleotides/bases, from about 10 to about 20 nucleotides/bases, from about 15 to about 40 nucleotides/bases, from about 15 to about 30 nucleotides/bases or from about 15 to about 20 nucleotides/bases. In various embodiments, the acetyltransferase inhibitor comprises an oligonucleotide. In various embodiments, the acetyltransferase inhibitor comprises RNA. In various embodiments, the acetyltransferase inhibitor comprises inhibitory RNA. In various embodiments, the acetyltransferase inhibitor is selected from the group consisting of: antisense oligonucleotide (ASO), gapmer, short interfering RNA (siRNA), short hairpin RNA (shRNA), microRNA (miRNA), guide RNA (gRNA), single guide RNA (sgRNA) and combinations thereof. In some embodiments, the acetyltransferase inhibitor comprises a CRISPR (clustered regularly interspaced short palindromic repeats) -Cas (CRISPR associated protein) complex, e.g. a CRISPR-Cas9 complex, or parts thereof. An antisense oligonucleotide (ASO) may knockdown a gene, e.g. GCN5L1 or BLOC1S1, through exon skipping and subsequently mRNA decay or translational inhibition. A SiRNA may induce gene knockdown, e.g. GCN5L1 or BLOC1S1 knockdown, via the endoribonuclease DICER.

In various embodiments, the oligonucleotide comprises: a) a sequence, optionally a linear sequence, that is complementary to BLOC1S1 gene or SEQ ID NO: 2, optionally a coding sequence (CDS) of BLOC1S1 gene or SEQ ID NO: 3 and/or SEQ ID NO: 4, or part thereof; or b) a sequence sharing at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity with the sequence in a) or a sequence differing from the sequence in a) by about one nucleotide/base, about two nucleotides/bases, about three nucleotides/bases, about four nucleotides/bases, about five nucleotides/bases, by about six nucleotide/base, about seven nucleotides/bases, about eight nucleotides/bases, about nine nucleotides/bases or about ten nucleotides/bases. In various embodiments, the oligonucleotide comprises: a) a sequence that is complementary to a coding sequence (CDS) of BLOC1S1 gene, SEQ ID NO:3 and/or SEQ ID NO:4 or part thereof; or b) a sequence sharing at least about 75% sequence identity with the sequence in a). In various embodiments, the oligonucleotide comprises SEQ ID NO: 1 (or AGAGGAGGCGAGAGGCUAU) or b) a sequence sharing at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity with the sequence in a) or a sequence differing from the sequence in a) by about one nucleotide/base, about two nucleotides/bases, about three nucleotides/bases, about four nucleotides/bases, about five nucleotides/bases, by about six nucleotide/base, about seven nucleotides/bases, about eight nucleotides/bases, about nine nucleotides/bases or about ten nucleotides/bases. In various embodiments, the oligonucleotide comprises a sequence sharing at least about 75% sequence identity with SEQ ID NO: 1, or a sequence differing from SEQ ID NO: 1 by about one nucleotide, about two nucleotides, about three nucleotides, about four nucleotides or about five nucleotides. In various embodiments, the acetyltransferase inhibitor reduces/inhibits an expression of GCN5L1.

In various embodiments, the oligonucleotide comprising a sequence that is complementary to a part of BLOC1S1 gene, a part of the coding sequence (CDS) of BLOC1S1 gene, or a part of any of SEQ ID Nos. 2 to 4 comprises a sequence that is complementary to a stretch of sequences/nucleic acid residues in the BLOC1S1 gene, coding sequence (CDS) of BLOC1S1 gene, or SEQ ID Nos. 2 to 4 such that hybridization of the oligonucleotide to at least a part of the gene or sequence is achievable. In various embodiments, the stretch of sequences/nucleic acid residues comprises at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29 or at least about 30 successive nucleic acid residues in the BLOC1S1 gene, coding sequence (CDS) of BLOC1S1 gene, or any of SEQ ID Nos. 2 to 4. In some embodiments, the oligonucleotide may comprise a sequence that is complementary to more than one stretch, e.g. about two, about three stretches etc, of sequences/nucleic acid residues in the BLOC1S1 gene, coding sequence (CDS) of BLOC1S1 gene, or SEQ ID Nos. 2 to 4.

In various embodiments, the acetyltransferase inhibitor is capable of decreasing/reducing the expression (e.g. gene or protein expression) of the acetyltransferase by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100%. In one embodiment, the acetyltransferase inhibitor is capable of decreasing/reducing the expression of the acetyltransferase by about 50% to 70%.

In various embodiments, the agent is capable of improving one or more of the following properties in an ALS or ALS-like motor neuron: mitochondrial dysfunction, metabolic respiration defect, altered morphology, abnormal mitochondria morphology, survival/basal survival, soma size, amount of primary neurites, endoplasmic reticulum (ER) stress, basal respiration, ATP-linked oxygen consumption rate (OCR), ATP production, spare respiratory capacity, oxidative phosphorylation, deacetylase expression and/or activity (e.g. sirtuin such as SIRT3), Complex I activity, mitochondrial $NAD^+$ levels, CHOP gene expression, spliced XBP1 (sXBP1) amounts/levels, extracellular acidification rate (ECAR) and mitophagy e.g. to be similar or more similar to that in a healthy/normal motor neuron. In some embodiments, the agent is capable of changing/modulating (e.g. increasing/promoting or decreasing/reducing) one or more of the above properties by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100% such that the one or more properties resembles or more closely resembles that in a healthy/normal motor neuron. In some embodiments, the change is at least about 0.1 times, at least about 0.2 times, at least about 0.3 times, at least about 0.4 times, at least about 0.5 times, at least about 0.6 times, at least about 0.7 times, at least about 0.8 times or at least about 0.9 times. In some embodiments, the change is more than about 1 times e.g. at least about 1.05 times, at least about 1.1 times, at least about 1.15 times, at least about 1.2 times, at least about 1.25 times, at least about 1.3 times, at least about 1.35 times, at least about 1.4 times, at least about 1.45 times, at least about 1.5 times, at least about 1.55 times, at least about 1.6 times, at least about 1.65 times, at least about 1.7 times, at least about 1.75 times, at least about 1.8 times, at least about 1.85 times, at least about 1.9 times, at least about 2 times, at least about 2.5 times, at least about 3 times, at least about 3.5 times, at least about 4 times, at least about 4.5 times, at least about 5 times, at least about 5.5 times, at least about 6 times, at least about 6.5 times, at least about 7 times, at least about 7.5 times, at least about 8 times, at least about 8.5 times, at least about 9 times at least about 9.5 times or at least about 10 times.

In various embodiments, the method comprises an in vitro or ex vivo method.

In various embodiments, there is provided an agent or a composition capable of modulating/regulating acetylation of a mitochondrial product in motor neurons. In various embodiments, the agent or the composition is capable of reducing/inhibiting acetylation of a mitochondrial product such as a mitochondrial protein in motor neurons. The agent or the composition may be used in therapy. The agent or the composition may be a pharmaceutical composition. The agent or the composition may comprise one or more of a suitable carrier, additive, adjuvant, diluent and excipient. In various embodiments, there is provided the agent or the composition for use in therapy. In various embodiments, there is provided the agent or the composition for use in treating a motor neuron disease. In various embodiments, there is provided the agent or the composition for use in treating an ALS or ALS-like disease. In some embodiments, there is provided a therapeutically effective amount of the agent or the composition for use in treating an ALS or ALS-like disease e.g. an amount of the agent or the composition that is capable of reducing mitochondrial protein acetylation in a motor neuron by a desired amount. In various embodiments therefore, there is provided an agent or a composition capable of reducing mitochondrial protein acetylation for use in treating ALS or an ALS-like disease.

In various embodiments, the agent or the composition is selected from the group consisting of: a deacetylase activator or agonist, an acetyltransferase inhibitor or antagonist and combinations thereof. In various embodiments, the deacetylase activator comprises a SIRT3 activator. In various embodiments, the SIRT3 activator is selected from the group consisting of: a small molecule, a NAD or a precursor thereof, and combinations thereof. In various embodiments, the small molecule is selected from the group consisting of: 7-hydroxy-3-(4'-methoxyphenyl) coumarin (C12), honokiol, dihydromyricetin (DHM) and derivatives, analogues and combinations thereof. In various embodiments, the NAD precursor is selected from the group consisting of tryptophan, quinolinic acid, nicotinic acid (NA), nicotinamide (Nam), nicotinamide mononucleotide (NMN) nicotinamide riboside (NR), nicotinic acid and derivatives, analogues and combinations thereof. In various embodiments, the acetyltransferase inhibitor comprises GCN5L1 inhibitor. In various embodiments, the GCN5L1 inhibitor comprises an oligonucleotide and/or a chemical. In various embodiments, the oligonucleotide is selected from the group consisting of: antisense oligonucleotide (ASO), gapmer, short interfering RNA (siRNA), short hairpin RNA (shRNA), microRNA (miRNA), guide RNA (gRNA), single guide RNA (sgRNA) and combinations thereof. In various embodiments, the oligonucleotide comprises: a) a sequence that is complementary to a CDS of BLOC1S1 gene or part thereof, or SEQ ID NO: 3 or part thereof, or SEQ ID NO: 4 or part thereof; or a sequence sharing at least about 75% sequence identity with the sequence in a). In various embodiments, the oligonucleotide comprises a sequence sharing at least about 75% sequence identity with SEQ ID NO: 1, or a sequence differing from SEQ ID NO: 1 by about one nucleotide, about two nucleotides, about three nucleotides, about four nucleotides or about five nucleotides.

In some embodiments, the agent or the composition may increase the level of expression (e.g. gene and/or protein expression) of SIRT3 (or any complex comprising SIRT3). In some embodiments, the agent or the composition may increase the level of RNA encoding SIRT3. In some embodiments, the agent or the composition may increase the transcription of nucleic acid encoding SIRT3. In some embodiments, the agent or the composition may promote proper post-transcriptional processing (e.g. splicing, translation, post-translational processing) of RNA encoding SIRT3. In some embodiments, the agent or the composition may increase a level of SIRT3 protein (or any protein complex comprising SIRT3). In some embodiments, the agent or the composition may reduce degradation of SIRT3 (or any protein complex comprising SIRT3). In some embodiments, the agent or the composition may promote interaction between SIRT3 (or any protein complex comprising SIRT3) and an interaction partner for SIRT3 (or an interaction partner for any protein complex comprising SIRT3). In some embodiments, the agent or the composition may increase/enhance the level of a function of SIRT3 (or any complex comprising SIRT3). In some embodiments, the agent or the composition may activate SIRT3 (or any complex comprising SIRT3). In some embodiments, the agent or the composition may increase the level of deacetylase activity by SIRT3 (and/or any complex comprising SIRT3). In some embodiments, the agent or the composition may reduce/inhibit hyper-acetylation of mitochondrial proteins resulting from reduced SIRT3 activity. In some embodiments, the agent or the composition may promote deacetylation of targets downstream of SIRT3.

In some embodiments, the agent or the composition may reduce the level of expression (e.g. gene and/or protein expression) of GCN5L1 (or any complex comprising GCN5L1). In some embodiments, the agent or the composition may reduce the level of RNA encoding GCN5L1. In some embodiments, the agent or the composition may reduce/inhibit the transcription of nucleic acid encoding GCN5L1. In some embodiments, the agent or the composition may reduce/inhibit post-transcriptional processing (e.g. splicing, translation, post-translational processing) of RNA encoding GCN5L1. In some embodiments, the agent or the composition may reduce/inhibit a level of GCN5L1 protein (or any protein complex comprising GCN5L1). In some embodiments, the agent or the composition may increase/promote degradation of GCN5L1 (or any protein complex comprising GCN5L1). In some embodiments, the agent or the composition may reduce/inhibit/disrupt interaction between GCN5L1 (or any protein complex comprising GCN5L1) and an interaction partner for GCN5L1 (or an interaction partner for any protein complex comprising GCN5L1). In some embodiments, the agent or the composition may reduce the level of a function of GCN5L1 (or any complex comprising GCN5L1). In some embodiments, the agent or the composition may inhibit the acetyltransferase activity of GCN5L1 (or any complex comprising GCN5L1). In some embodiments, the agent or the composition may reduce the level of acetyltransferase activity by GCN5L1 (or any complex comprising GCN5L1). In some embodiments, the agent or the composition may reduce/inhibit hyper-acetylation of mitochondrial proteins resulting from increased GCN5L1 activity. In some embodiments, the agent or the composition may reduce/inhibit acetylation of targets downstream of GCN5L1.

In some embodiments, the agent or the composition may reduce acetylation of mitochondrial proteins in motor neurons. In some embodiments, the agent or the composition may reduce acetylation of manganese superoxide dismutase (MnSOD) in motor neurons such as acetylation of lysine 68 on manganese superoxide dismutase (MnSOD K68ac).

An agent or a composition may be evaluated for the properties recited in the preceding paragraphs using suitable assays. The assays may be e.g. in vitro assays, optionally cell-based assays or cell-free assays.

Gene expression can be analysed by means well known to the skilled person. The level of RNA encoding a given gene can be determined e.g. by techniques such as RT-qPCR. Protein expression can also be determined by means well known to the skilled person. The level of a given protein/isoform thereof can be determined e.g. by antibody-based methods including western blot, immunohistochemistry/immunohisto(cyto)chemistry/cytochemistry, flow cytometry, ELISA, etc.

The increase of gene or protein expression level of a given gene may be to more than 1 times, e.g. one of ≥1.01 times, ≥1.05 times, ≥1.1 times, ≥1.15 times, ≥1.2 times, ≥1.25 times, ≥1.3 times, ≥1.35 times, ≥1.4 times, ≥1.45 times, ≥1.5 times, ≥1.55 times, ≥1.6 times, ≥1.65 times, ≥1.7 times, ≥1.75 times, ≥1.8 times, ≥1.85 times, ≥1.9 times, ≥2 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, ≥70 times, ≥80 times, ≥90 times or ≥100 times the level of expression observed in the uninduced state (i.e. in the absence of an inducer of SIRT3 expression/activity). In some embodiments, an agent or a composition capable of increasing gene or protein expression increases gene expression by greater than 5%, e.g. one of ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90%, ≥91%, ≥92%, ≥93%, ≥94%, ≥95%, ≥96%, ≥97%, ≥98%, ≥99%, ≥100%, ≥200%, ≥300%, ≥400%, ≥500%, ≥600%, ≥700%, ≥800%, ≥900% or ≥1000% of the expression observed in the uninduced state.

The reduction of gene or protein expression of a given gene may be to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of expression observed in the uninhibited state (i.e. in the absence of a GCN5L1 inhibitor). In some embodiments, an agent capable of reducing/inhibiting gene or protein expression inhibits greater than 5%, e.g. one of ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90%, ≥91%, ≥92%, ≥93%, ≥94%, ≥95%, ≥96%, ≥97%, ≥98%, ≥99% or 100% of the expression observed in the uninhibited state.

Agents or compositions capable of increasing gene expression of SIRT3 (e.g. increasing the level of RNA encoding SIRT3, increasing transcription of nucleic acid encoding SIRT3, and/or reducing degradation of RNA encoding SIRT3) or capable of reducing/inhibiting gene expression of GCN5L1 (e.g. reducing the level of RNA encoding GCN5L1, reducing/inhibiting transcription of nucleic acid encoding GCN5L1 and/or increasing/promoting degradation of RNA encoding GCN5L1) may be identified using assays comprising detecting the level of RNA encoding SIRT3 or GCN5L1, e.g. by RT-qPCR. Such assays may comprise treating cells/tissue e.g. motor neuron with the agent or the composition, and subsequently comparing the level of RNA encoding SIRT3 or GCN5L1 in such cells/tissue to the level of RNA encoding SIRT3 or GCN5L1 in cells/tissue of an appropriate control condition (e.g. untreated/vehicle-treated cells/tissue).

Agents or compositions capable of increasing protein expression of SIRT3 (e.g. increasing the level of SIRT3 protein or any protein complex comprising SIRT3, or reducing degradation of SIRT3 protein or any protein complex comprising SIRT3) or reducing/inhibiting protein expression of GCN5L1 (e.g. reducing the level of GCN5L1 protein or any protein complex comprising GCN5L1, or increasing/promoting degradation of GCN5L1 protein or any protein complex comprising GCN5L1) may be identified using assays comprising detecting the level of SIRT3 protein, GCN5L1 protein, or any complex thereof e.g. using antibody/reporter-based methods (western blot, ELISA, immunohisto/cytochemistry, etc.). Such assays may comprise treating cells/tissue e.g. motor neuron with the agent or the composition, and subsequently comparing the level of the protein/protein complex in such cells/tissue to the level in cells/tissue of an appropriate control condition (e.g. untreated/vehicle-treated cells/tissue).

Agents or compositions capable of promoting interaction between SIRT3 (or any complex comprising SIRT3) and an interaction partner for SIRT3 (or an interaction partner for any complex comprising SIRT3) or reducing/inhibiting/disrupting interaction between GCN5L1 (or any complex comprising GCN5L1) and an interaction partner for GCN5L1 (or an interaction partner for a complex comprising GCN5L1) may be identified using assays comprising detecting the level of interaction, e.g. using antibody/reporter-based methods. The level of interaction between SIRT3 (or any complex comprising SIRT3) and an interaction partner for SIRT3 (or an interaction partner for any complex comprising SIRT3) or the level of interaction between GCN5L1 (or any complex comprising GCN5L1) and an interaction partner for GCN5L1 (or an interaction partner for any complex comprising GCN5L1) can be analysed e.g. using resonance energy transfer techniques (e.g. FRET, BRET), or methods analysing a correlate of the interaction. Assays may comprise treating cells/tissue e.g. motor neuron with the agent or the composition, and subsequently comparing the level of interaction between SIRT3 (or any complex comprising SIRT3) and an interaction partner for SIRT3 (or an interaction partner for any complex comprising SIRT3) or the level of interaction between GCN5L1 (or any complex comprising GCN5L1) and an interaction partner for GCN5L1 (or an interaction partner for a complex comprising GCN5L1) in such cells/tissue to the level of interaction observed in cells/tissue of an appropriate control condition (e.g. untreated/vehicle-treated cells/tissue). The level of interaction can be analysed e.g. using techniques such as ELISA, surface plasmon resonance or biolayer interferometry analysis. Assays may comprise comparing the level of interaction in the presence of the agent or the composition to the level of interaction in an appropriate control condition (e.g. the absence of the agent or the composition).

The promotion/increase of interaction between SIRT3 (or any complex comprising SIRT3) and an interaction partner for SIRT3 (or an interaction partner for any complex comprising SIRT3) may be to more than 1 times, e.g. one of ≥1.01 times, ≥1.05 times, ≥1.1 times, ≥1.15 times, ≥1.2 times, ≥1.25 times, ≥1.3 times, ≥1.35 times, ≥1.4 times, ≥1.45 times, ≥1.5 times, ≥1.55 times, ≥1.6 times, ≥1.65 times, ≥1.7 times, ≥1.75 times, ≥1.8 times, ≥1.85 times, ≥1.9 times, ≥2 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, ≥70 times, ≥80 times, ≥90 times or ≥100 times the level of interaction observed in the uninduced state (i.e., in the absence of an agent or a composition that promotes/increases interaction between SIRT3 (or any complex comprising SIRT3) and an interaction partner for SIRT3 (or an interaction partner for a complex comprising SIRT3)). In some embodiments, an agent capable of promoting/increasing interaction between (SIRT3 or any complex comprising SIRT3) and an interaction partner for SIRT3 (or an interaction partner for a complex comprising SIRT3) increases interaction greater than 5%, e.g. one of ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90%, ≥91%, ≥92%, ≥93%, ≥94%, ≥95%, ≥96%, ≥97%, ≥98%, ≥99%, ≥100%, ≥200%, ≥300%, ≥400%, ≥500%, ≥600%, ≥700%, ≥800%, ≥900% or ≥1000% of the interaction observed in the uninduced state.

The reduction/decrease/disruption of interaction GCN5L1 (or any complex comprising GCN5L1) and an interaction partner for GCN5L1 (or an interaction partner for any complex comprising GCN5L1) may be to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of interaction observed in the uninhibited state (i.e., in the absence of an agent or a composition that reduces/decreases/disrupts interaction between GCN5L1 (or any complex comprising GCN5L1) and an interaction partner for GCN5L1 (or an interaction partner for any complex comprising GCN51L1)). In some embodiments, an agent or a composition capable of reducing/inhibiting/disrupting interaction between GCN5L1 (or any complex comprising GCN5L1) and an interaction partner for GCN5L1 (or an interaction partner for a complex comprising GCN5L1) inhibits greater than 5%, e.g. one of ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90%, ≥91%, ≥92%, ≥93%, ≥94%, ≥95%, ≥96%, ≥97%, ≥98%, ≥99% or 100% of the interaction observed in the uninhibited state.

Agents or compositions capable of modulating a function of SIRT3 or GCN5L1 (or any complexes thereof) may be identified using assays for the relevant function. Such assays may comprise treating cells/tissue e.g. motor neuron expressing SIRT3 or GCN5L1 (or any complexes thereof) with the agent or the composition, and subsequently comparing the level of the relevant function to the level observed in an appropriate control condition (e.g. untreated/vehicle-treated cells/tissue). The agents or compositions may also be identified using assays comprising detecting the level of a correlate of a function of SIRT3 or GCN5L1 (or any complexes thereof) (e.g. the gene and/or protein expression, and/or activity, of one or more proteins whose expression is directly/indirectly upregulated or downregulated as a consequence of a function of or SIRT3/GCN5L1 (or any complexes thereof)). Such assays may comprise treating cells/tissue e.g. motor neuron expressing a function of SIRT3 or GCN5L1 (or any complexes thereof) with the agent, and subsequently comparing the level of the correlate of a function of SIRT3 or GCN5L1 (or any complexes thereof) in such cells/tissue to the level of the correlate of the relevant function in an appropriate control condition (e.g. untreated/vehicle-treated cells/tissue). A function of SIRT3 (and/or any complex comprising SIRT3) may e.g. be deacetylase activity. A correlate of a function of SIRT3 (and/or any complex comprising SIRT3) may e.g. be a product of deacetylase activity. A function of GCN5L1 (and/or any complex comprising GCN5L1) may e.g. be acetyltransferase activity. A correlate of a function of GCN5L1 (and/or any complex comprising GCN5L1) may e.g. be a product of acetyltransferase activity.

Agents or compositions capable of increasing deacetylase activity by SIRT3 (or any complex comprising SIRT3) or reducing/inhibiting acetyltransferase activity by GCN5L1 (or any complex comprising GCN5L1) may be identified using assays comprising detecting the level of deacetylase or acetyltransferase activity, e.g. using antibody/reporter-based methods. Assays may comprise treating cells/tissue e.g. motor neuron expressing SIRT3, GCN5L1 (or any complexes thereof) with the agent or the composition, and subsequently comparing the level of acetylation (e.g. in mitochondrial proteins or in a representative mitochondrial protein) to the level of acetylation observed in an appropriate control condition (e.g. untreated/vehicle-treated cells/tissue). Assays may also comprise comparing the level of the relevant activity displayed by SIRT3, GCN5L1 (or any complex thereof) in the presence of the agent or the composition to the level observed in the absence of the agent or the composition. An example of an assay that may be performed is described in the Examples.

The enhancement/increase of a function of SIRT3 (or any complex comprising SIRT3) (e.g. deacetylase activity) may be to more than 1 times, e.g. one of ≥1.01 times, ≥1.05 times, ≥1.1 times, ≥1.15 times, ≥1.2 times, ≥1.25 times, ≥1.3 times, ≥1.35 times, ≥1.4 times, ≥1.45 times, ≥1.5 times, ≥1.55 times, ≥1.6 times, ≥1.65 times, ≥1.7 times, ≥1.75 times, ≥1.8 times, ≥1.85 times, ≥1.9 times, ≥2 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, ≥70 times, ≥80 times, ≥90 times or ≥100 times the level of activity observed in the uninduced state. In some embodiments, an agent or a composition capable of enhancing/increasing a function of SIRT3 (or any complex comprising SIRT3) (e.g. deacetylase activity) enhances/increases the activity greater than 5%, e.g. one of ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90%, ≥91%, ≥92%, ≥93%, ≥94%, ≥95%, ≥96%, ≥97%, ≥98%, ≥99%, ≥100%, ≥200%, ≥300%, ≥400%, ≥500%, ≥600%, ≥700%, ≥800%, ≥900% or ≥1000% of the relevant activity observed in the uninduced state.

The reduction/inhibition of a function of GCN5L1 (or any complex comprising GCN5L1) (e.g. acetyltransferase activity) may be to less than 1 times, e.g. one of ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of activity observed in the uninhibited state. In some embodiments, an agent or a composition capable of reducing/inhibiting a function of GCN5L1 (and/or any complex comprising GCN5L1) (e.g. acetyltransferase activity) inhibits greater than 5%, e.g. one of ≥10%, ≥15%, ≥20%, ≥25%, ≥30%, ≥35%, ≥40%, ≥45%, ≥50%, ≥55%, ≥60%, ≥65%, ≥70%, ≥75%, ≥80%, ≥85%, ≥90%, ≥91%, ≥92%, ≥93%, ≥94%, ≥95%, ≥96%, ≥97%, ≥98%, ≥99% or 100% of the relevant activity observed in the uninhibited state.

In some embodiments, the agent is comprises a SIRT3-binding molecule, a SIRT3 complex-binding molecule, a molecule capable of increasing the level of SIRT3, a molecule capable of increasing the level of SIRT3 complex, a GCN5L1-binding molecule, a GCN5L1 complex-binding molecule, a molecule capable of reducing the level of GCN5L1 or a molecule capable of reducing the level of GCN5L1 complex. As used herein, a "SIRT3-binding molecule" refers to a molecule which is capable of binding to SIRT3. A "SIRT3 complex-binding molecule" refers to a molecule which is capable of binding to a complex comprising SIRT3. A "GCN5L1-binding molecule" refers to a molecule which is capable of binding to GCN5L1. A "GCN5L1 complex-binding molecule" refers to a molecule which is capable of binding to a complex comprising GCN5L1.A SIRT3-binding molecule or a GCN5L1-binding molecule can be identified using any suitable assay for detecting binding of a molecule to the relevant factor (i.e. SIRT3, GCN5L1 or any complex comprising SIRT3 and/or GCN5L1). Such assays may comprise detecting the formation of a complex between the relevant factor and the molecule.

SIRT3-binding molecules, GCN5L1-binding molecules (or binding molecules of any complex comprising SIRT3 or GCN5L1) can be analysed in appropriate assays in order to identify agonists of SIRT3 or antagonists of GCN5L1. For example, molecules which bind specifically to SIRT3 (and/or any complex comprising SIRT3) can be evaluated for their ability to activate deacetylase or for their ability to activate deacetylase activity. For example, molecules which bind specifically to GCN5L1 (and/or any complex comprising GCN5L1) can be evaluated for their ability to inhibit acetyltransferase, or for their ability to inhibit acetyltransferase activity.

In some embodiments, a SIRT3-binding molecule (or a binding molecule of any complex comprising SIRT3) may promote the ability of its target (i.e., SIRT3 or any complex comprising SIRT3) to interact with an interaction partner. In some embodiments, the SIRT3-binding molecule (or a binding molecule of any complex comprising SIRT3) may change the conformation of an active site on SIRT3. In some embodiments, a GCN5L1-binding molecule (or a binding molecule of any complex comprising GCN5L1) may inhibit the ability of its target (i.e., GCN5L1 or any complex comprising GCN5L1) to interact with an interaction partner. In some embodiments, a GCN5L1-binding molecule (or a binding molecule of any complex comprising GCN5L1) behaves as a competitive inhibitor of interaction between its target and an interaction partner for its target. The binding molecule may occupy, or otherwise reduce access to, a region of its target required for binding to an interaction partner for its target. The ability of a SIRT3-binding molecule or a GCN5L1-binding molecule (or a binding molecule of any complex comprising SIRT3 or GCN5L1) to promote or inhibit interaction between its target and an interaction partner for its target can be evaluated e.g. by analysis of interaction in the presence of, or following incubation of one or both of the interaction partners with the relevant binding molecule. Examples of suitable assays to determine whether a given binding agent is capable of promoting or inhibiting interaction between its target and an interaction partner for its target includes ELISA and competitive ELISA.

In various embodiments, the SIRT3-binding molecules, GCN5L1-binding molecules (or binding molecules of any complex comprising SIRT3 or GCN5L1) comprises a chemical i.e. a chemical inhibitor. In some embodiments, the chemical comprises a small molecule. The chemical compound or small molecule may be an organic or inorganic compound. In some embodiments, the chemical or small molecule comprises an organic compound. The chemical compound or small molecules may be identified by screening of chemical compound libraries or small molecules libraries. A chemical compound library or a small molecule library may be a plurality of chemical compounds or small molecules that have been assembled from any of multiple sources, including chemically synthesized compounds or molecules and natural products, or that have been generated by combinatorial chemistry techniques.

The small molecule may have a low molecular weight of no more than about 1500 Da, no more than about 1400 Da, no more than about 1300 Da, no more than about 1200 Da, no more than about 1100 Da, no more than about 1000 Da, no more than about 900 Da, no more than about 800 Da, no more than about 700 Da, no more than about 600 Da, no more than about 500 Da, no more than about 400 Da, no more than about 300 Da, no more than about 200 Da, no more than about 100 Da or no more than about 50 Da. In some embodiments, the small molecule has a molecular weight of about 50 Da to about 1500 Da, about 100 Da to about 1000 Da or from about 300 Da to about 700 Da.

In various embodiments, the SIRT3-binding molecules, GCN5L1-binding molecules (or binding molecules of any complex comprising SIRT3 or GCN5L1) comprises aptamers. Nucleic acid aptamers are reviewed e.g. in Zhou and Rossi Nat Rev Drug Discov. 2017 16(3):181-202, and may be identified and/or produced by the method of Systematic Evolution of Ligands by EXponential enrichment (SELEX), or by developing SOMAmers (slow off-rate modified aptamers) (Gold L et al. (2010) PLoS ONE 5(12):e15004). Aptamers and SELEX are described in Tuerk and Gold, Science (1990) 249(4968):505-10, and in WO 91/19813. Nucleic acid aptamers may comprise DNA and/or RNA, and may be single stranded or double stranded. They may comprise chemically modified nucleic acids, for example in which the sugar and/or phosphate and/or base is chemically modified. Such modifications may improve the stability of the aptamer or make the aptamer more resistant to degradation and may include modification at the 2' position of ribose. Nucleic acid aptamers may be chemically synthesised, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer (e.g., see Sinha, N. D.; Biernat, J.; McManus, J.; Köster, H. Nucleic Acids Res. 1984, 12, 4539; and Beaucage, S. L.; Lyer, R. P. (1992). Tetrahedron 48 (12): 2223). Peptide aptamers and methods for their generation and identification are reviewed in Reverdatto et al., Curr Top Med Chem. (2015) 15(12):1082-101, which is hereby incorporated by reference in its entirety.

Molecules which are capable of increasing the level of SIRT3 (or a complex comprising SIRT3) include molecules capable of increasing gene and/or protein expression of SIRT3 (or a complex comprising SIRT3). In some embodiments, a molecule capable of increasing the level of SIRT3 (or a complex comprising SIRT3) induces or increases the expression of a polypeptide encoded by the SIRT3 gene. Increase of gene or protein expression of a given target gene (e.g. SIRT3 gene) may comprise e.g. increasing/promoting transcription of the gene, promoting proper post-transcriptional processing (e.g. splicing) of RNA transcribed from the gene, increasing the stability of RNA transcribed from the gene, reducing/preventing degradation of RNA transcribed from the gene, increasing/promoting translation of RNA transcribed from the gene into protein, promoting proper post-translational processing of a polypeptide encoded by the gene, increasing the stability of a polypeptide encoded by the gene, or reducing/preventing degradation of a polypeptide encoded by the gene.

Molecules which are capable of reducing the level of GCN5L1 (or a complex comprising GCN5L1) include molecules capable of reducing gene and/or protein expression of GCN5L1 (or a complex comprising GCN5L1). In some embodiments, a molecule capable of reducing the level of GCN5L1 (or a complex comprising GCN5L1) reduces or prevents the expression of a polypeptide encoded by the BLOC1S1 gene. Inhibition of gene or protein expression of a given target gene (e.g. BLOC1S1gene) may comprise e.g. inhibiting transcription of the gene, inhibiting post-transcriptional processing (e.g. splicing) of RNA transcribed from the gene, reducing the stability of RNA transcribed from the gene, promoting degradation of RNA transcribed from the gene, inhibiting translation of RNA transcribed from the gene into protein, inhibiting post-translational processing of a polypeptide encoded by the gene, reducing the stability of a polypeptide encoded by the gene, or promoting degradation of a polypeptide encoded by the gene.

Inhibition or induction/activation/promotion/upregulation of gene or protein expression may be achieved e.g. by altering/disrupting the nucleotide sequence of the gene, or altering/disrupting nucleotide sequence required for expression of the gene (e.g. a regulatory sequence governing expression of the gene). In some embodiments, inhibiting or induction/activation/promotion/upregulation gene or protein expression may comprise altering a nucleotide sequence, e.g. by substitution, deletion or insertion of one or more nucleotides. For example, in particular aspects and embodiments, the present disclosure contemplates inhibiting gene or protein expression by deletion of all or part of the nucleotide sequence of the relevant gene. For example, in particular aspects and embodiments, the present disclosure contemplates inducing/activating/promoting/upregulating gene or protein expression by introducing an activating mutation, introducing a regulatory sequence that enhances expression of the gene and/or by amplifying all or part of the nucleotide sequence of the relevant gene.

Altering/disrupting the nucleotide sequence to inhibit/prevent gene or protein expression from a gene may be referred to as gene 'knockout'. A gene 'knockin' may alter (e.g. increase) gene or protein expression e.g., by introduction of one or more copies of the target gene, or by operatively inserting a regulatory sequence that enhances expression of the target gene.

Nucleotides sequences may be disrupted e.g. by homologous recombination, or by target nucleic acid modification using site-specific nucleases (SSNs).

Modification by homologous recombination may involve the exchange of nucleic acid sequence through crossover events guided by homologous sequences, and is reviewed, for example, in Mortensen Curr Protoc Neurosci. (2007) Chapter 4:Unit 4.29 and Vasquez et al., PNAS (2001) 98(15): 8403-8410 both of which are hereby incorporated by reference in their entirety.

Gene editing using SSNs is reviewed e.g. in Eid and Mahfouz, Exp Mol Med. (2016) 48(10): e265, which is hereby incorporated by reference in its entirety. Enzymes capable of creating site-specific double strand breaks (DSBs) can be engineered to introduce DSBs to target nucleic acid sequences of interest. DSBs may be repaired by either error-prone non-homologous end-joining (NHEJ), in which the two ends of the break are rejoined, often with insertion or deletion of nucleotides. Alternatively, DSBs may be repaired by highly homology-directed repair (HDR), in which a DNA template with ends homologous to the break site is supplied and introduced at the site of the DSB. SSNs capable of being engineered to generate target nucleic acid sequence-specific DSBs include zinc-finger nucleases (ZFNs), transcription activator-like effector nucleases (TALENs) and clustered regularly interspaced palindromic repeats/CRISPR-associated-9 (CRISPR/Cas9) systems.

ZFN systems are reviewed e.g. in Umov et al., Nat Rev Genet. (2010) 11(9):636-46, which is hereby incorporated by reference in its entirety. ZFNs comprise a programmable Zinc Finger DNA-binding domain and a DNA-cleaving domain (e.g. a Fokl endonuclease domain). The DNA-binding domain may be identified by screening a Zinc Finger array capable of binding to the target nucleic acid sequence. TALEN systems are reviewed e.g. in Mahfouz et al., Plant Biotechnol J. (2014) 12(8):1006-14, which is hereby incorporated by reference in its entirety. TALENs comprise a programmable DNA-binding TALE domain and a DNA-cleaving domain (e.g. a Fokl endonuclease domain). TALEs comprise repeat domains consisting of repeats of 33-39 amino acids, which are identical except for two residues at positions 12 and 13 of each repeat which are repeat variable di-residues (RVDs). Each RVD may determine binding of the repeat to a nucleotide in the target DNA sequence according to the following relationship: "HD" binds to C, "NI" binds to A, "NG" binds to T and "NN" or "NK" binds to G (Moscou and Bogdanove, Science (2009) 326(5959):1501.). CRISPR/Cas9 and related systems e.g. CRISPR/Cpf1, CRISPR/C2c1, CRISPR/C2c2 and CRISPR/C2c3 are reviewed e.g. in Nakade et al., Bioengineered (2017) 8(3):265-273, which is hereby incorporated by reference in its entirety. These systems comprise an endonuclease (e.g. Cas9, Cpf1 etc.) and the single-guide RNA (sgRNA) molecule. The sgRNA can be engineered to target endonuclease activity to nucleic acid sequences of interest.

Disruption of a nucleotide sequence using SSNs can be achieved in an animal e.g. by administering nucleic acid encoding the components of the relevant SSN system to the animal. For example, the animal may be administered with one or more vectors comprising nucleic acid encoding the constituents of the SSN system for targeting the relevant gene.

Inhibition of gene or protein expression may also be achieved e.g. by treatment with an agent capable of reducing gene or protein expression. For example, inhibition of gene or protein expression may be achieved using an inhibitory nucleic acid, such as an antisense nucleic acid. Antisense nucleic acids may bind to target nucleic acid by complementary base pairing. Where the target nucleic acid is an RNA (e.g. RNA transcribed from the relevant gene), binding of the antisense nucleic acid to the target RNA may promote degradation of and/or inhibit translation of the RNA. An inhibitory nucleic acid may be an antisense oligonucleotide (ASO).

The use of inhibitory nucleic acids for gene silencing is reviewed e.g. in O'Keefe, Mater Methods (2013) 3:197, which is hereby incorporated by reference in its entirety. An inhibitory nucleic acid may inhibit gene or protein expression by RNA interference (RNAi). RNAi involves inhibition of gene expression and translation by targeted neutralisation of mRNA molecules. In some embodiments, the inhibitory nucleic acid is small interfering RNA (siRNA), a short hairpin RNA (shRNA), or a micro RNA (miRNA).

As used herein, the terms "small interfering RNA" or "siRNA", "short hairpin RNA" or "shRNA", "micro RNA" or "miRNA" encompass both naturally occurring sequences and synthetically produced sequences.

The design of miRNAs is discussed in John et al, PLoS Biology, 11(2), 1862-1879, 2004. Suitable siRNA, shRNA and miRNA sequences for targeting a given gene may be designed e.g. using siRNA Wizard (invivoGEN) or BLOCK-IT RNAi Designer (Invitrogen).

As background, siRNAs may be derived by processing of long double stranded RNAs and when found in nature are typically of exogenous origin. Micro-interfering RNAs (miRNAs) comprise endogenously encoded small non-coding RNAs. Both siRNA and miRNA may inhibit the translation of mRNAs bearing partially complimentary target sequences without RNA cleavage and degrade mRNAs bearing fully complementary sequences. siRNAs are typically double-stranded. To optimise the effectiveness of RNA mediated inhibition of the function of a target gene, the length of the siRNA molecule may be optimised for correct recognition of the siRNA by the RISC complex that mediates the recognition by the siRNA of the mRNA target. DNA sequences encoding miRNAs include the miRNA sequence and an approximate reverse complement. When this DNA sequence is transcribed into a single-stranded RNA molecule, the miRNA sequence and its reverse-complement may base pair to form a partially double stranded RNA segment.

ShRNAs are typically more stable than synthetic siRNAs. A shRNA may comprise short inverted repeats separated by a small loop sequence. One inverted repeat may be complimentary to the gene target. In cells, the shRNA is typically processed by DICER into siRNA which degrades the target gene mRNA and suppresses its expression. ShRNAs may be produced within a cell, e.g. by transcription from a vector. In various embodiments, there is provided use of the agent or composition in the manufacture of a medicament for treating a motor neuron disease. In various embodiments, there is provided use of the agent or composition in the manufacture of a medicament for treating ALS or an ALS-like disease.

In various embodiments, there is provided a method of treating ALS or an ALS-like disease in a subject, the method comprising administering to the subject the agent or composition, optionally a therapeutically effective amount of the agent or composition. In various embodiments, the method further comprises determining the subject's suitability for the treatment. In various embodiments, determining the subject's suitability for the treatment comprises determining/measuring a level of mitochondrial protein acetylation in the subject's motor neuron (or motor neuron derived from the subject); and comparing it to a level of mitochondrial protein acetylation in a healthy/control motor neuron, wherein an elevated level of mitochondrial protein acetylation in the subject's motor neuron as compared to the level in the healthy/control motor neuron is indicative that the subject is suitable for the treatment. In various embodiments, the method comprises determining/measuring a level of mitochondrial protein acetylation in the subject's motor neuron and comparing the level to a level of mitochondrial protein acetylation after administration of the agent or composition. In various embodiments, a reduction in the level of mitochondrial protein acetylation in the subject's motor neuron after administration of the agent or composition may indicate that the treatment is effective and/or may indicate an improvement of the disease in the subject. In various embodiments, an increase in the level of mitochondrial protein acetylation in the subject's motor neuron after administration of the agent or composition may indicate that the treatment is ineffective and/or may indicate a worsening of the disease in the subject. In various embodiments therefore, the method may be a method of determining an efficacy of the treatment or a prognosis method. It will be appreciated that the method may also be helpful in determining/monitoring disease progression in a subject by comparing the level of mitochondrial protein acetylation in a subject's sample at different timepoints, wherein a reduction in the level of mitochondrial protein acetylation at a later timepoint as compared to an earlier timepoint is indicative that the disease is improving, while an increase in the level of mitochondrial protein acetylation at a later timepoint as compared to an earlier timepoint is indicative that the disease is worsening.

In various embodiments, there is provided a method of identifying/diagnosing ALS or an ALS-like disease in a subject, the method comprising: determining/measuring a level of mitochondrial protein acetylation in the subject's motor neuron; and comparing it to a level of acetylation in a healthy/control motor neuron, wherein an elevated level of mitochondrial protein acetylation in the subject's motor neuron as compared to the level in the healthy/control motor neuron is indicative that the subject has or is predisposed to ALS or an ALS-like disease.

In various embodiments, the subject comprises a mammalian subject. In various embodiments, the subject comprises a human subject. In various embodiments, the motor neuron comprises a mammalian motor neuron. In various embodiments, the motor neuron comprises a human motor neuron.

In various embodiments, there is provided a method of identifying:

(a) a molecule capable of binding to a mitochondrial protein deacetylase (e.g. SIRT3) and/or a mitochondrial protein acetyltransferase (e.g. GCN5L1), the method comprising contacting the deacetylase and/or acetyltransferase with a candidate molecule and determining whether the candidate molecule binds to the deacetylase and/or acetyltransferase;

(b) a modulator of a mitochondrial protein deacetylase (e.g. SIRT3) and/or a mitochondrial protein acetyltransferase (e.g. GCN5L1), the method comprising contacting a cell (e.g. a motor neuron) with a candidate molecule and detecting elevated or reduced expression, amount or activity of the deacetylase and/or acetyltransferase in or of the cell;

(c) a molecule suitable for the treatment, prophylaxis or alleviation of ALS or an ALS-like disease, the method comprising determining if a candidate molecule is an agonist or antagonist of a mitochondrial protein deacetylase (e.g. SIRT3) and/or a mitochondrial protein acetyltransferase (e.g. GCN5L1), preferably by exposing a candidate molecule to the deacetylase and/or acetyltransferase or a cell (e.g. a motor neuron) expressing the deacetylase and/or acetyltransferase in order to determine if the candidate molecule is an agonist or antagonist thereof; or (d) an agonist or antagonist of a mitochondrial protein deacetylase (e.g. SIRT3) and/or a mitochondrial protein acetyltransferase (e.g. GCN5L1), the method comprising administering a candidate molecule to an animal and determining whether the animal exhibits increased or decreased expression, amount or activity of the deacetylase and/or acetyltransferase; and optionally isolating or synthesising the molecule, modulator, agonist or antagonist.

In some embodiments, the molecule, modulator, agonist or antagonist so identified comprises a deacetylase activator e.g. SIRT3 activator and/or an acetyltransferase inhibitor e.g. GCN5L1 inhibitor. In some embodiments, the molecule, modulator, agonist or antagonist so identified comprises an oligonucleotide sharing at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity with SEQ ID NO: 1, or a sequence differing from SEQ ID NO: 1 by about one nucleotide/base, about two nucleotides/bases, about three nucleotides/bases, about four nucleotides/bases, about five nucleotides/bases, by about six nucleotide/base, about seven nucleotides/bases, about eight nucleotides/bases, about nine nucleotides/bases or about ten nucleotides/bases. In some embodiments, the molecule, modulator, agonist or antagonist so identified comprises an oligonucleotide sharing at least about 75% sequence identity with SEQ ID NO: 1, or a sequence differing from SEQ ID NO: 1 by about one nucleotide, about two nucleotides, about three nucleotides, about four nucleotides or about five nucleotides. In some embodiments, there is provided the oligonucleotide for use in therapy.

In various embodiments, there is provided a method of screening for/identifying an agent or a composition for treating ALS or an ALS-like disease, the method comprising: contacting a cell e.g. an ALS or ALS-like motor neuron with a candidate agent or composition; and determining whether mitochondrial protein acetylation in the cell e.g. motor neuron is reduced after the contact; and wherein where mitochondrial protein acetylation in the cell e.g. motor neuron is reduced after the contact, concluding that the candidate agent or composition is an agent or a composition for treating ALS or an ALS-like disease, wherein where mitochondrial protein acetylation in the cell e.g. motor neuron is not reduced after the contact, concluding that the candidate agent or composition is not an agent or a composition for treating ALS or an ALS-like disease. Protein acetylation may be measured by methods known to those skilled in the art. For example, protein acetylation may be measured by detecting lysine acetylation through use of antibodies specific to acetyl-lysine residues. The measurement/determination may be qualitative, quantitative or semi-quantitative. Suitable methods for detecting lysine acetylation status include Western blot analysis, immunoprecipitation, enzyme-linked immunosorbent assay (ELISA) mass spectrometry and combinations of these methods. In one embodiment, determining whether mitochondrial protein acetylation in the motor neuron is reduced after the contact comprises detecting for acetylation at lysine-68.

In various embodiments, the screening/identifying method may comprise or further comprise determining whether a level of expression (e.g. gene and/or protein expression) of SIRT3 (or any complex comprising SIRT3) is increased, a level of RNA encoding SIRT3 is increased, a transcription of nucleic acid encoding SIRT3 is increased, proper post-transcriptional processing (e.g. splicing, translation, post-translational processing) of RNA encoding SIRT3 is promoted, a level of SIRT3 protein (or any protein complex comprising SIRT3) is increased, a degradation of SIRT3 (or any protein complex comprising SIRT3) is reduced, an interaction between SIRT3 (or any protein complex comprising SIRT3) and an interaction partner for SIRT3 (or an interaction partner for any protein complex comprising SIRT3) is promoted, a level of a function of SIRT3 (or any complex comprising SIRT3) is increased/enhanced, SIRT3 (or any complex comprising SIRT3) is activated, a level of deacetylase activity by SIRT3 (and/or any complex comprising SIRT3) is increased, a hyper-acetylation of mitochondrial proteins resulting from reduced SIRT3 activity is reduced/inhibited and/or a deacetylation of targets downstream of SIRT3 is promoted and/or whether the candidate agent binds to SIRT3 (or a complex thereof) after the contact, and wherein one or more of the above is achieved after the contact, concluding that the candidate agent is an agent for treating ALS or an ALS-like disease, wherein one or more of the above is not achieved after the contact, concluding that the candidate agent is not an agent for treating ALS or an ALS-like disease.

In various embodiments, the screening/identifying method may comprise or further comprise determining whether a level of expression (e.g. gene and/or protein expression) of GCN5L1 (or any complex comprising GCN5L1 is reduced, a level of RNA encoding GCN5L1 is reduced, a transcription of nucleic acid encoding GCN5L1 is reduced/inhibited, a post-transcriptional processing (e.g. splicing, translation, post-translational processing) of RNA encoding GCN5L1 is reduced/inhibited, a level of GCN5L1 protein (or any protein complex comprising GCN5L1) is reduced/inhibited, a degradation of GCN5L1 (or any protein complex comprising GCN5L1) is increased/promoted, an interaction between GCN5L1 (or any protein complex comprising GCN5L1) and an interaction partner for GCN5L1 (or an interaction partner for any protein complex comprising GCN5L1) is reduced/inhibited/disrupted, a level of a function of GCN5L1 (or any complex comprising GCN5L1) is reduced, an acetyltransferase activity of GCN5L1 (or any complex comprising GCN5L1) is inhibited, a level of acetyltransferase activity by GCN5L1 (or any complex comprising GCN5L1) is reduced, a hyper-acetylation of mitochondrial proteins resulting from increased GCN5L1 activity is reduced/inhibited and/or an acetylation of targets downstream of GCN5L1 is reduced/inhibited and/or whether the candidate agent binds to GCN5L1 (or a complex thereof) after the contact, and wherein one or more of the above is achieved after the contact, concluding that the candidate agent is an agent for treating ALS or an ALS-like disease, wherein one or more of the above is not achieved after the contact, concluding that the candidate agent is not an agent for treating ALS or an ALS-like disease.

In various embodiments, the screening/identifying method may comprise or further comprise determining whether the candidate agent is capable of improving one or more of the following properties in the cell e.g. an ALS or ALS-like motor neuron after the contact: mitochondrial dysfunction, metabolic respiration defect, altered morphology, abnormal mitochondria morphology, survival/basal survival, soma size, amount of primary neurites, endoplasmic reticulum (ER) stress, basal respiration, ATP-linked oxygen consumption rate (OCR), ATP production, spare respiratory capacity, oxidative phosphorylation, deacetylase expression and/or activity (e.g. sirtuin such as SIRT3), Complex I activity, mitochondrial $NAD^+$ levels, CHOP gene expression, spliced XBP1 (sXBP1) amounts/levels, extracellular acidification rate (ECAR) and mitophagy e.g. to be similar or more similar to that in a healthy/normal motor neuron and wherein the candidate agent is capable of improving one or more of the above properties, concluding that the candidate agent is an agent for treating ALS or an ALS-like disease, wherein the candidate agent is incapable of improving one or more of the above properties, concluding that the candidate agent is not an agent for treating ALS or an ALS-like disease.

The determination of the above properties may be carried out by methods known to those skilled in the art or the methods described herein. Further, the determination be qualitative, quantitative or semi-quantitative. For example, in some embodiments, determining whether a property is changed/modulated (e.g. reduced/increased/promoted/improved etc.) may comprise determining whether the property is changed/modulated by a certain extent e.g. by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% or at least about 100% or at least about 0.1 times, at least about 0.2 times, at least about 0.3 times, at least about 0.4 times, at least about 0.5 times, at least about 0.6 times, at least about 0.7 times, at least about 0.8 times or at least about 0.9 times or more than about 1 times e.g. at least about 1.05 times, at least about 1.1 times, at least about 1.15 times, at least about 1.2 times, at least about 1.25 times, at least about 1.3 times, at least about 1.35 times, at least about 1.4 times, at least about 1.45 times, at least about 1.5 times, at least about 1.55 times, at least about 1.6 times, at least about 1.65 times, at least about 1.7 times, at least about 1.75 times, at least about 1.8 times, at least about 1.85 times, at least about 1.9 times, at least about 2 times, at least about 2.5 times, at least about 3 times, at least about 3.5 times, at least about 4 times, at least about 4.5 times, at least about 5 times, at least about 5.5 times, at least about 6 times, at least about 6.5 times, at least about 7 times, at least about 7.5 times, at least about 8 times, at least about 8.5 times, at least about 9 times at least about 9.5 times or at least about 10 times.

In various embodiments, there is provided an oligonucleotide sharing at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% sequence identity with SEQ ID NO: 1, or a sequence differing from SEQ ID NO: 1 by about one nucleotide/base, about two nucleotides/bases, about three nucleotides/bases, about four nucleotides/bases, about five nucleotides/bases, by about six nucleotide/base, about seven nucleotides/bases, about eight nucleotides/bases, about nine nucleotides/bases or about ten nucleotides/bases. In some embodiments, there is provided an oligonucleotide sharing at least about 75% sequence identity with SEQ ID NO: 1, or a sequence differing from SEQ ID NO: 1 by about one nucleotide, about two nucleotides, about three nucleotides, about four nucleotides or about five nucleotides. In some embodiments, there is provided the oligonucleotide for use in therapy.

In various embodiments, there is provided a method of generating a heterozygous L144F mutation in SOD1 gene in a healthy human iPSC line, thereby generating a pair of isogenic iPSCs. In various embodiments, there is provided a method of generating a heterozygous G298S mutation in TDP43 gene in a healthy human iPSC line, thereby generating a pair of isogenic iPSCs. In various embodiments, there is provided method of generating a SIRT3 haploinsufficient human/mouse iPSC model. In various embodiments, there is provided a motor neuron disease model, such as an ALS or ALS-like disease model, the disease model comprising depleted SIRT3 expression and/or haploinsufficient SIRT3. In various embodiments, there is provided a method for motor neuron enrichment for metabolic flux measurements. In various embodiments, there is provided a method for in vitro characterization of iPSC-derived neurons, where hypo-oxidation and hyper-glycolytic metabolic profiles are hallmark of ALS motor neurons. In various embodiments, there is provided a method for activating SIRT3 in human motor neurons, thereby promoting healthy mitochondrial respiration and reducing hyper-glycolytic phenotype of ALS motor neurons. In various embodiments, there is provided a method for depleting GCN5L1 expression in human motor neurons, thereby promoting healthy mitochondrial respiration and reducing hyper-glycolytic phenotype of ALS motor neurons.

In various embodiments, there is provided a method, a product or a use as described herein.

EXAMPLES

Example embodiments of the disclosure will be better understood and readily apparent to one of ordinary skill in the art from the following discussions and if applicable, in conjunction with the figures. It should be appreciated that some modifications may be made without deviating from the scope of the invention. Example embodiments are not necessarily mutually exclusive as some may be combined with one or more embodiments to form new exemplary embodiments.

Results

Figure 1A:
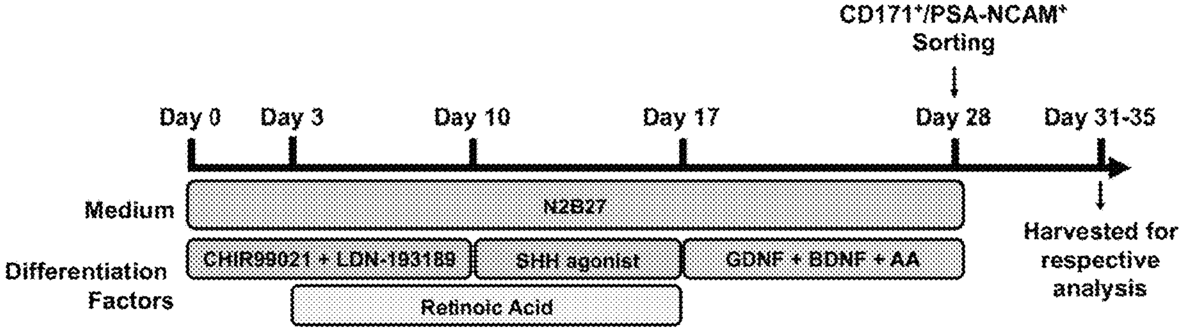
FIG. 1: ALS iPSC-derived MNs exhibit diseased phenotypes. (A) Schematic of the MN differentiation protocol. (B) Immunostaining of wild-type (BJ-iPS, 18a and GM23720), familial ALS (29d, 47a and 19f) and sporadic ALS (sALS1, sALS2, sALS3) iPSC-derived cultures at day 28 indicating the derivation of $ISL1^+SM132^+$ MNs. Cellular nuclei were counterstained with DAPI. Scale bars, 50 μm. (C) Quantification of $ISL1^+$ MNs from day 25 to day 35 demonstrating that wild-type MNs (BJ-iPS, 18a and GM23720) remain viable while familial and sporadic ALS MNs show significantly reduced survival over time. (D) qPCR quantification of ER stress transcripts CHOP and spliced XBP1 (sXBP1) in MN cultures at day 28. Fold changes are normalized to expression levels of respective mRNA in BJ-iPS. (E) Immunostaining of isogenic ALS (BJ-SOD1$^{L144F}$ and BJ-TDP43$^{G298S}$) iPSC-derived cultures at day 28 indicating the formation of $ISL1^+SM132^+$ MNs. Cellular nuclei were counterstained with DAPI. Scale bars, 50 μm. (F) Quantification of $ISL1^+$ MNs derived from BJ-SOD1$^{L144F}$ and BJ-TDP43$^{G298S}$ from day 25 to day 35 revealed an accelerated death phenotype similar to that of other ALS lines. (G) MN cultures derived from BJ-SOD1$^{L144F}$ and BJ-TDP43$^{G298S}$ show upregulation of CHOP and sXBP1 compared to its isogenic control line BJ-iPS. In (D) and (G), gene expression was normalized to ACTINB and HPRT. ***$p<0.001$, n.s. non-significant; two-tailed t test.
Figure 1B:
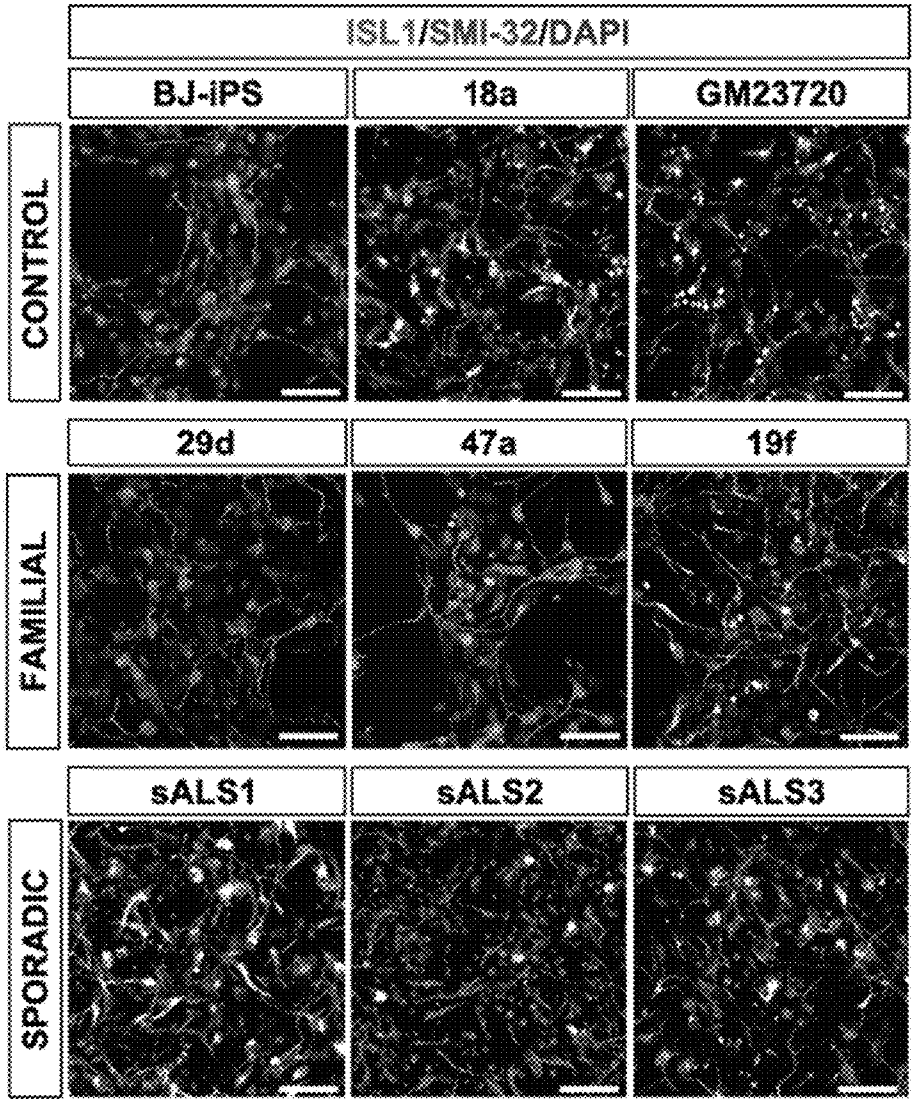
Figure 1C:
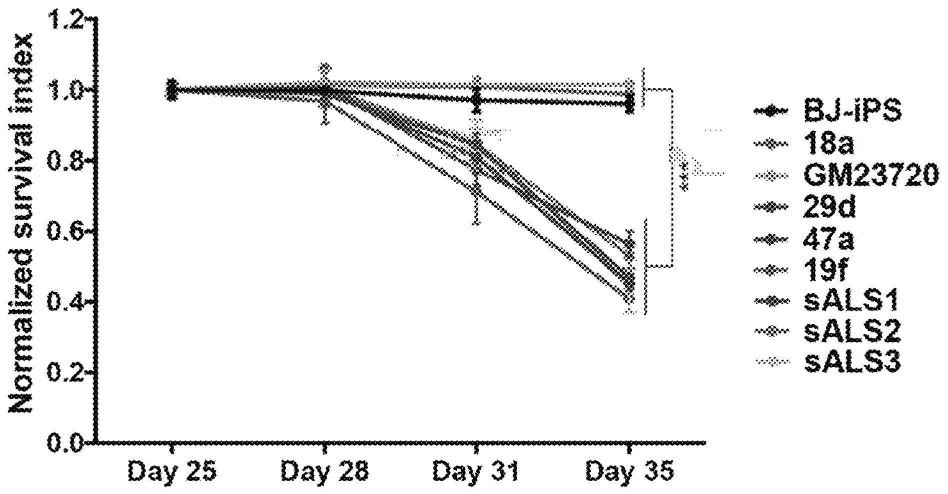
Figure 1D:
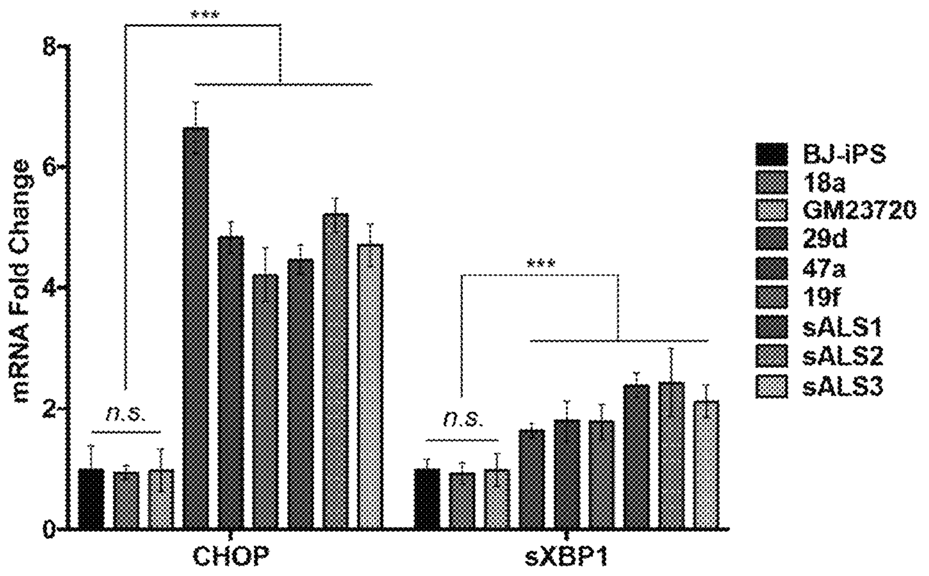

MNs Generated from ALS Patient iPSCs and Isogenic ALS Knock-In iPSCs Exhibit Reduced Mitochondrial Respiration and ATP Production MNs were differentiated from three healthy iPSC lines: BJ-iPS, 18a and GM23720, 3 sporadic ALS lines: sALS1, sALS2 and sALS3, as well as familial ALS iPSCs (harboring the following mutations): 29d ($SOD1^{L144F}$) 49a ($TDP43^{G298S}$) and 19f (C9ORF72 expanded GGGGCC repeats) using established protocols (FIG. 1A). Using this chemically defined protocol, $ISL1^{+}SM132^{+}$ MNs were effectively derived from all of these iPSC lines at day 28 (FIG. 1B). To confirm ALS phenotypes in these cell lines that were previously reported, the basal survival of $ISL1^{+}$ MNs was measured from day 25 to day 35 and it was found that an accelerated death phenotype is associated with the ALS MNs (FIG. 1C). Since elevated ER stress is also a molecular signature of ALS MNs, mRNA levels of key genes in the ER stress pathway were also measured and significant upregulation of CHOP and spliced XBP1 (sXBP1) was found (FIG. 1D).

Figure 1E:
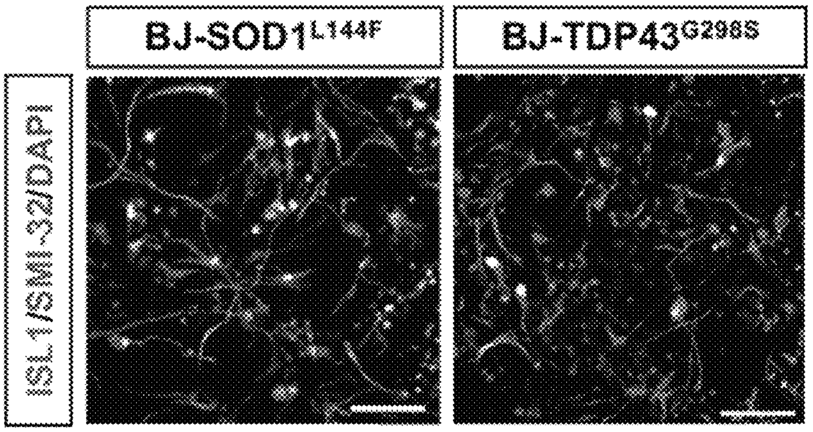
Figure 1F:
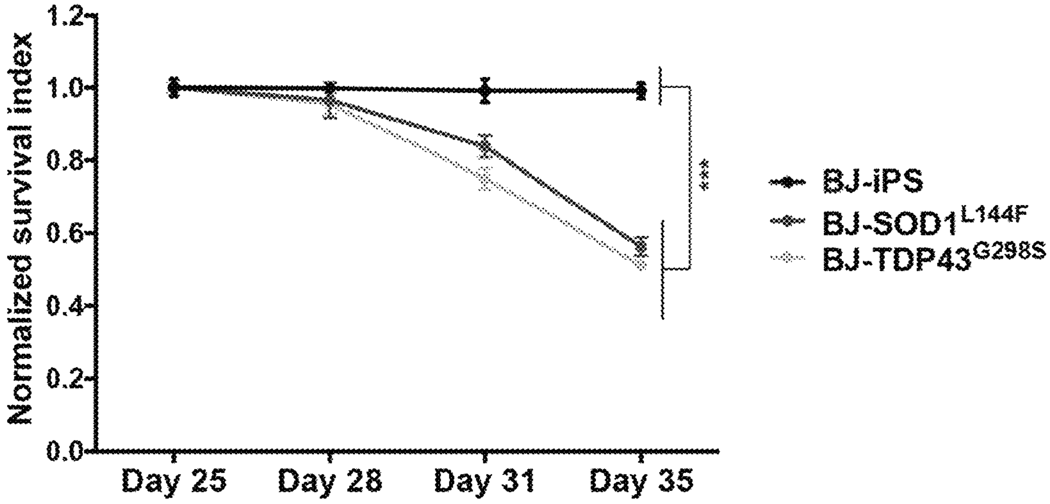
Figure 1G:
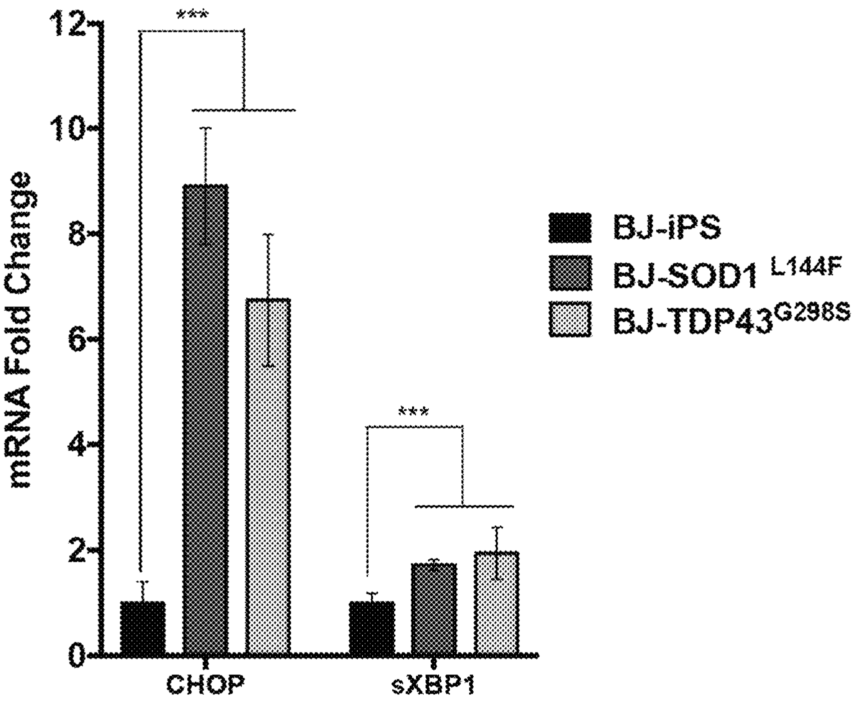
Figure 13A:
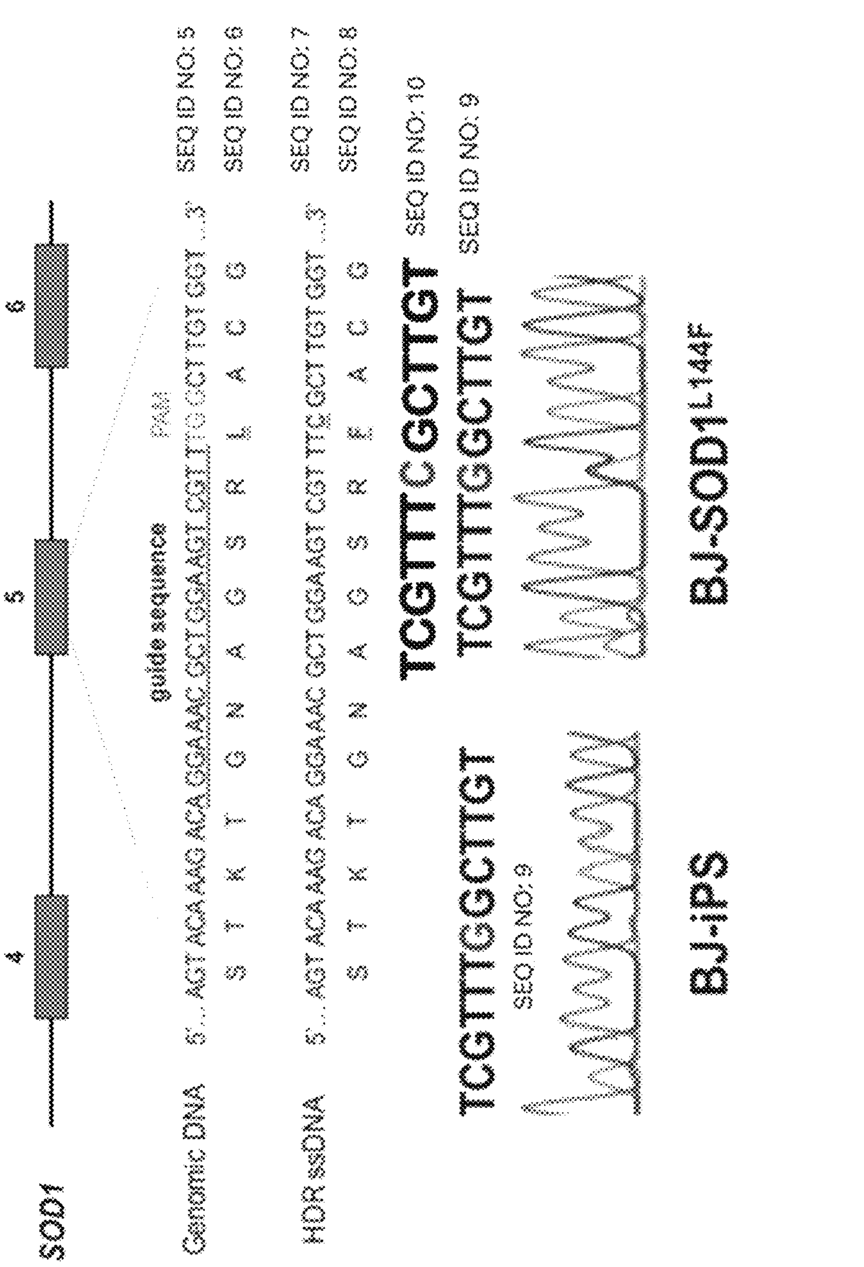
FIG. 13: Generation of isogenic lines using CRISPR/Cas9 technology (Related to FIGS. 1 and 5). Schematic summarizing the strategy for generating an isogenic knock-in for $SOD1^{L144F}$ and $TDP43^{G298S}$ mutation and isogenic knockout for SIRT3 into the BJ-iPS background. Guide RNA sequence is underlined with the PAM sequence highlighted in grey. (A) A single stranded oligonucleotide harboring the mutation serves as the repair template to facilitate the G to C transition within exon 5 that confers the leucine (L) to phenylalanine (F) mutation. (B) A single stranded oligonucleotide harboring the mutation serves as the repair template to facilitate the G to A transition within exon 5 that confers the glycine (G) to serine (S) mutation. (C) DNA sequencing confirms 6 bp and 9 bp deletion in BJ-$SIRT3^{+/-}$ #6 and #17 exon 1 respectively. (D) Both isogenic SIRT3 haploinsufficiency clones differentiates well into $ISL1^+$ $SM132^+$ MNs with similar efficiency as BJ-iPS. Cellular nuclei were counterstained with DAPI. Scale bars, 50 μm. n.s. non-significant. (SEQ ID Nos: 5-20).
Figure 13B:
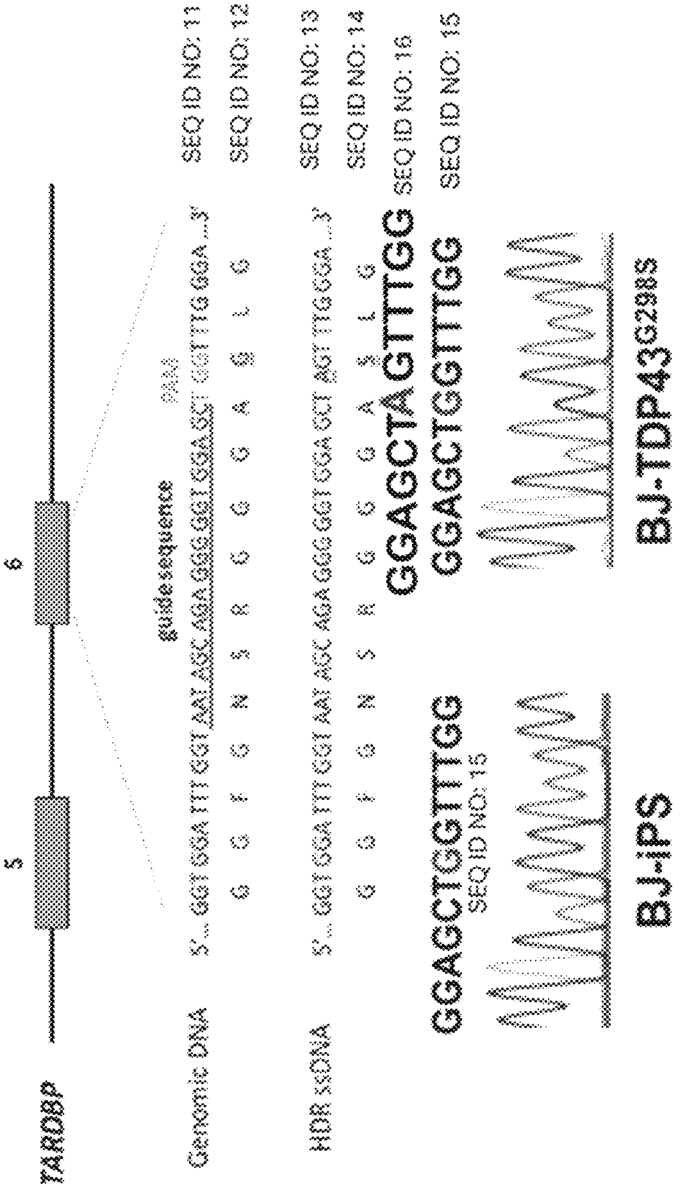

To ensure that the ALS-specific phenotypes and molecular profiles are not due to inherent variability between cell lines, isogenic controls in which the $SOD1^{L144F}$ and $TDP43^{G298S}$ mutations were introduced into the healthy BJ-iPS line using the CRISPR/Cas9 technology were generated (FIG. 1E; FIGS. 13A, 13B). Mutations were then confirmed by DNA-sequencing (FIGS. 13A, 13B). Similar to what was observed with the patient iPSC lines, MNs derived from the isogenic $SOD1^{L144F}$ (BJ-$SOD1^{L144F}$) and $TDP43^{G298S}$ (BJ-$TDP43^{G298S}$) knock-in lines also showed decreased MN survival and elevated expression of ER stress genes CHOP and sXBP1 (FIG. 1F, 1G).

Figure 2A:
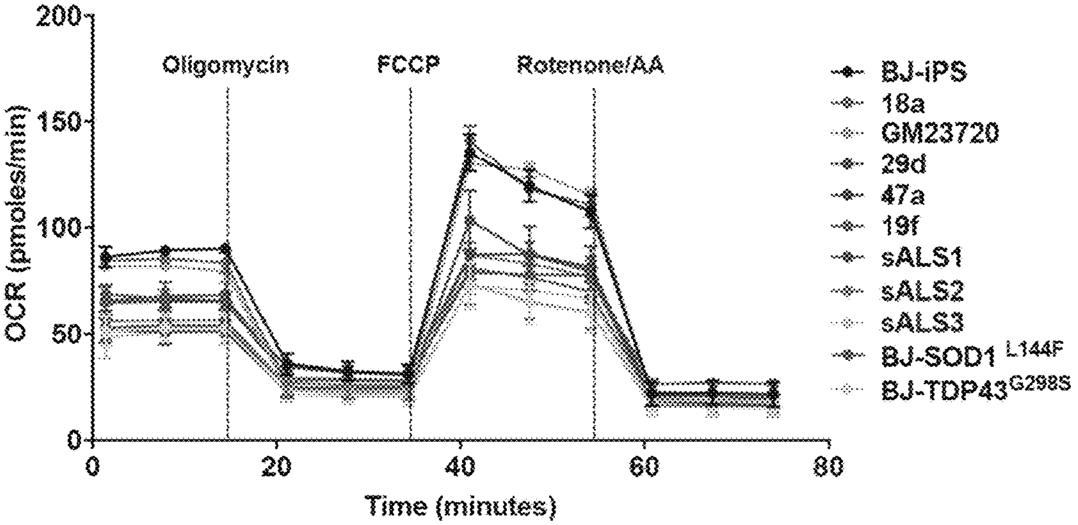
FIG. 2: Sporadic and familial ALS MNs show a hypo-oxidative and hyper-glycolytic metabolic profile. (A) Metabolic flux plots of healthy and ALS patient-derived sorted neurons, where oxygen consumption rate (OCR) was measured as a function of time. The MitoStress assay was used to measure bioenergetics parameters, by adding Complex V inhibitor Oligomycin, mitochondrial uncoupler FCCP and Complexes I and III inhibitors Rotenone and Antimycin A (AA). (B) Basal respiration, ATP production and spare respiration were calculated for sorted neurons from each of the cell lines and demonstrated reduced mitochondrial respiration in ALS MNs. (C) Metabolic flux plots of healthy and ALS patient-derived sorted neurons, where extracellular acidification rate (ECAR) was measured as a function of time. The Glycolysis stress assay was used to measure bioenergetics parameters, by adding glucose, Complex V inhibitor Oligomycin, and hexokinase inhibitor 2-DG. (D) Basal acidification, glycolysis and glycolytic capacity were calculated for sorted neurons from each of the cell lines and demonstrated elevated glycolysis in ALS MNs. (E) OCR measurements using the MitoStress assay was performed and calculated for cortical neurons derived from healthy, ALS and diseased isogenic iPSCs at day 28. (F) Metabolic flux analyses were performed using the MitoStress assay. Basal respiration, ATP production and spare respiration calculated for BJ-iPS, BJ-SOD1$^{L144F}$ and BJ-TDP43$^{G298S}$ cortical neurons reveal no significant changes in basal respiration and ATP production. Likewise, healthy and ALS patient iPSC-derived cortical neurons reveal no significant changes in basal respiration and ATP production. (G) OCR measurements using the MitoStress assay was performed and calculated for cardiomyocytes derived from healthy, ALS and diseased isogenic iPSCs at day 28. (H) Metabolic flux analyses were performed using the MitoStress assay. Basal respiration, ATP production and spare respiration calculated for BJ-iPS, BJ-SOD1$^{L144F}$ and BJ-TDP43$^{G298S}$ cardiomyocytes reveal no significant changes in basal respiration and ATP production. Likewise, healthy and ALS patient iPSC-derived cardiomyocytes reveal no significant changes in basal respiration and ATP production. ***$p<0.001$, n.s. non-significant; two-tailed t test.
Figure 2B:
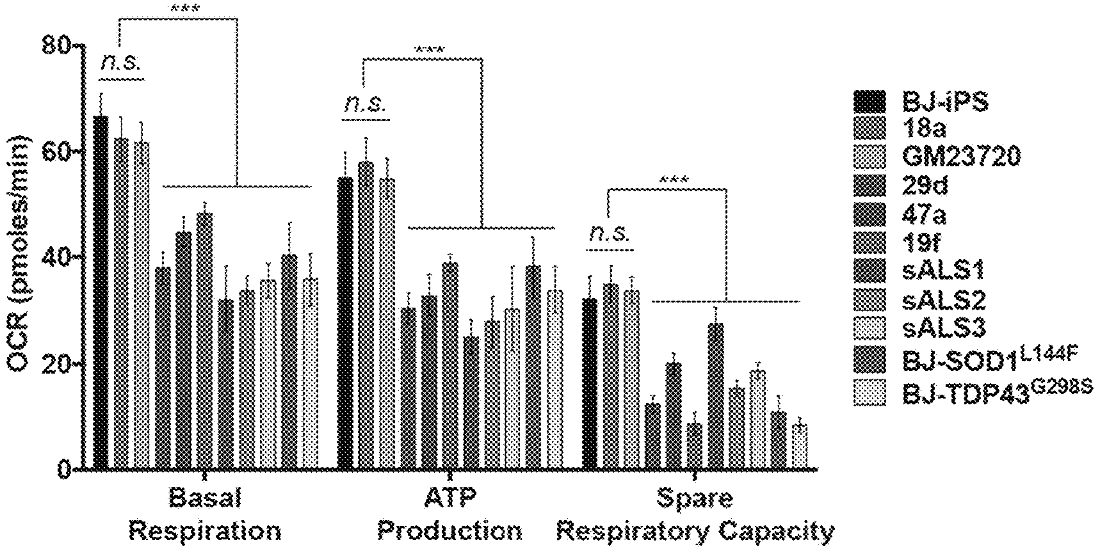
Figure 14A:
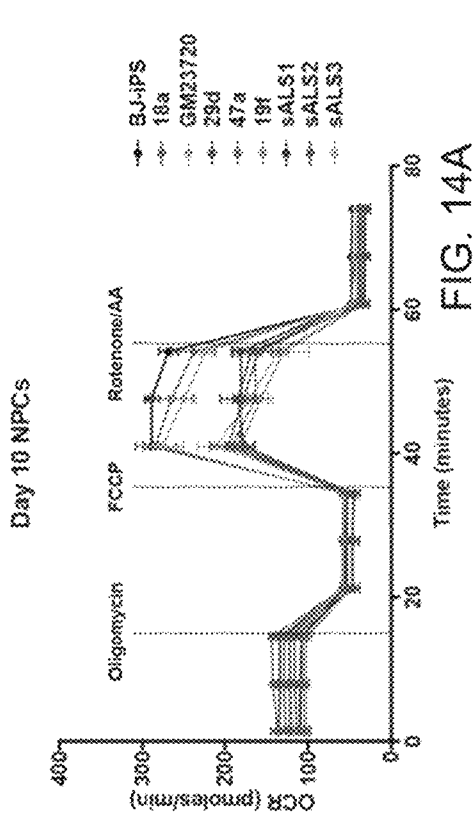
FIG. 14: Metabolic flux measurements in day 10 NPCs reveal insignificant changes between ALS and healthy cells (Related to FIG. 2). (A) OCR measurements using the MitoStress assay was performed and calculated for wild-type and ALS NPCs at day 10. (B) Basal respiration, ATP production and spare respiration were calculated for NPCs from each of the cell lines reveal no significant differences in ATP production but significantly reduced spare respiration in ALS NPCs. (C) OCR measurements using the MitoStress assay was performed and calculated for wild-type and isogenic ALS NPCs at day 10. (D) Basal respiration, ATP production and spare respiration were calculated for NPCs from each of the cell lines reveal no significant differences in ATP production but significantly reduced spare respiration in isogenic ALS NPCs. (E) ECAR measurements using the Glycolysis stress assay was performed and calculated for wild-type and ALS NPCs at day 10. (F) Basal acidification, glycolysis and glycolytic capacity were calculated for NPCs from each of the cell lines reveals no significant differences in glycolysis. (G) ECAR measurements using the Glycolysis stress assay was performed and calculated for wild-type and isogenic ALS NPCs at day 10. (H) Basal acidification, glycolysis and glycolytic capacity were calculated for NPCs from each of the cell lines reveals no significant differences in glycolysis. ***$p<0.001$, n.s. non-significant.
Figure 14B:
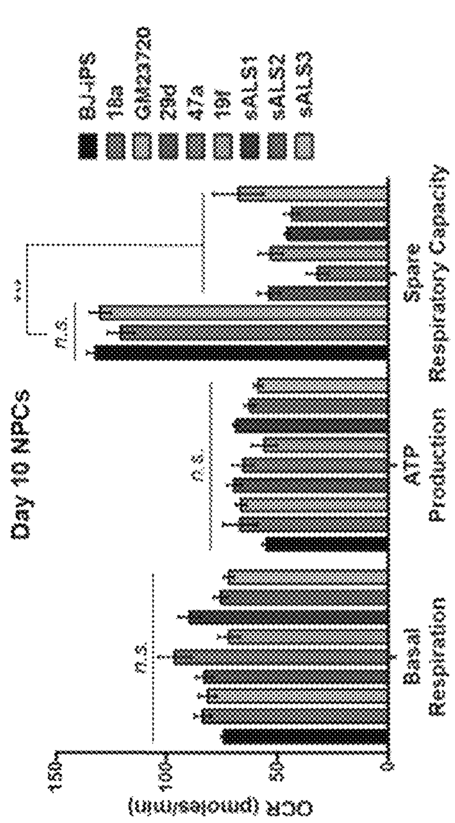

Although it has been shown that ALS neurons have abnormal mitochondria, it has not been established if these morphological abnormalities have any effects on mitochondrial functions in ALS MNs. Since oxidative phosphorylation is critical for maintenance of neuronal metabolism and survival, it was investigated if mitochondrial respiration in ALS MNs could be compromised. To enrich for MNs in the iPSC-derived cultures, magnetic sorting was performed using a cocktail of PSA-NCAM and CD171 antibodies. Using this sorting strategy, $ISL1^{+}$ MNs were enriched to approximately 60% (FIGS. 14A, 14B) without the use of AraC, which is sometimes used to deplete neural progenitor cells (NPCs) in the cultures but also induces neuronal death through oxidative stress. To investigate whether ALS MNs exhibit metabolic respiration defects, oxygen consumption rate (OCR) of these sorted neurons was measured as a function of time using an extracellular flux analyzer. It was found that both familial and sporadic ALS lines displayed significantly reduced basal respiration, decreased ATP-linked OCR as well as spare respiratory capacity compared to the healthy MNs (FIGS. 2A, 2B). Likewise, MNs derived from BJ-$SOD1^{L144F}$ and BJ-$TDP43^{G298S}$ isogenic iPSCs exhibited similar reductions in basal respiration (p<0.0001), ATP production (p<0.0001) and spare respiratory capacity (p<0.01), similar to 29d and 47a MNs that also possess the heterozygous L144F mutation in SOD1 and G298S mutation in TDP43 respectively (FIGS. 2A, 2B).

Figure 2C:
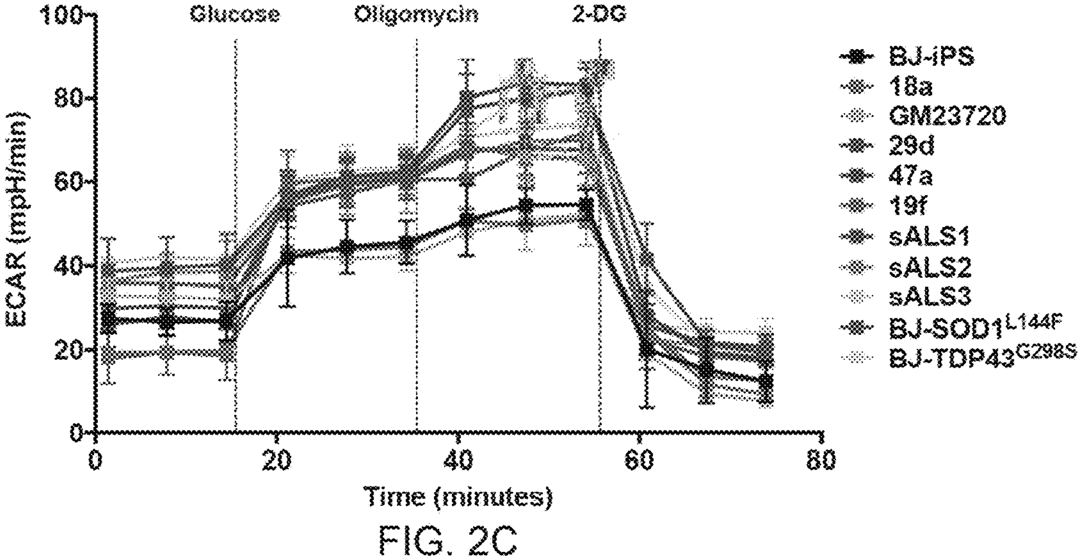
Figure 2D:
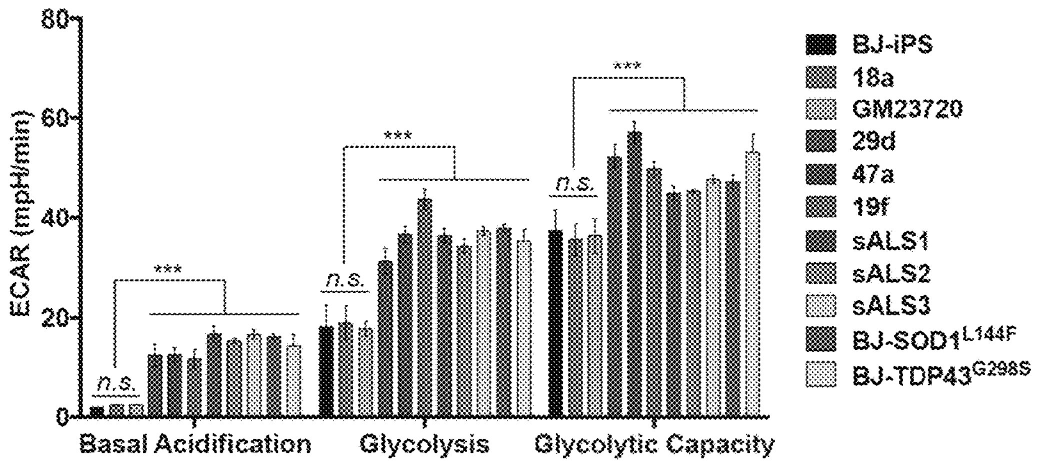
Figure 14C:
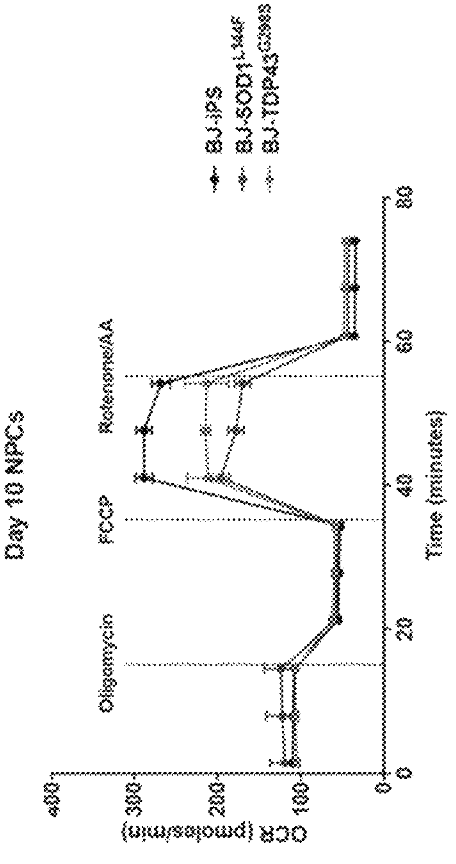
Figure 14D:
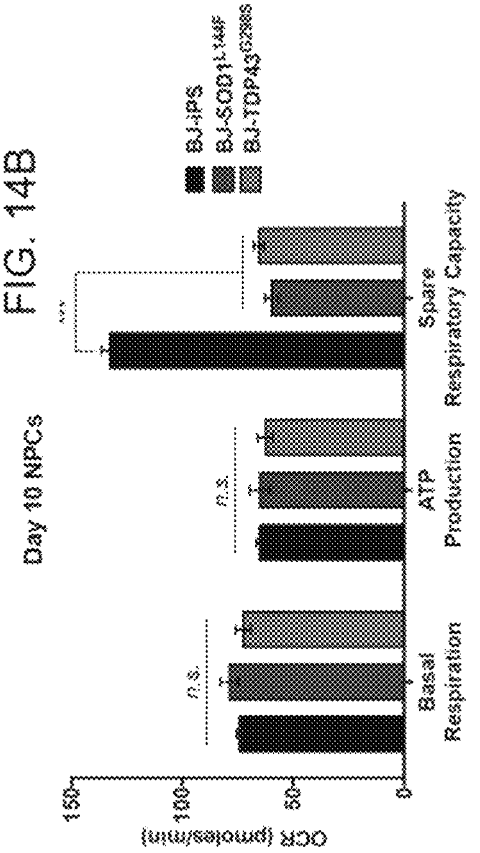
Figure 14E:
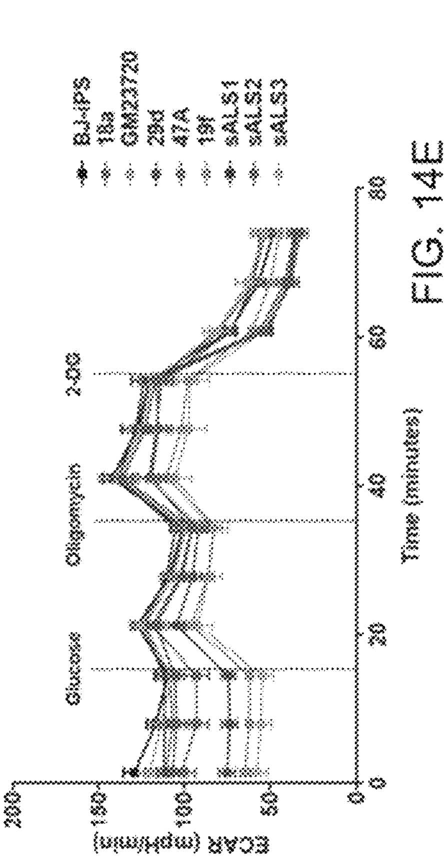
Figure 14F:
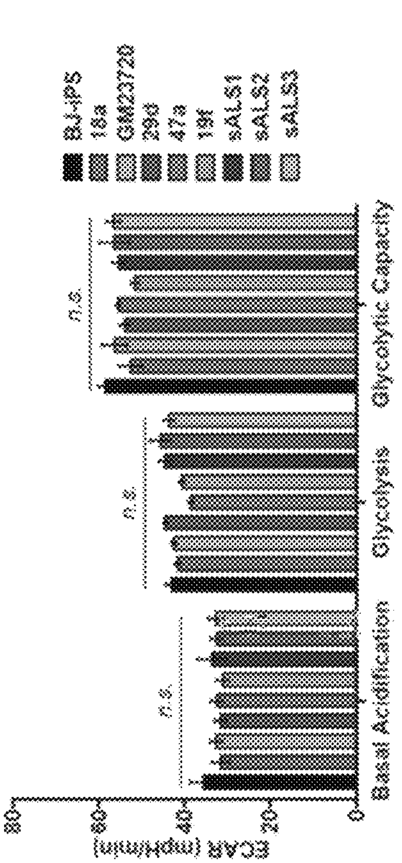
Figure 14G:
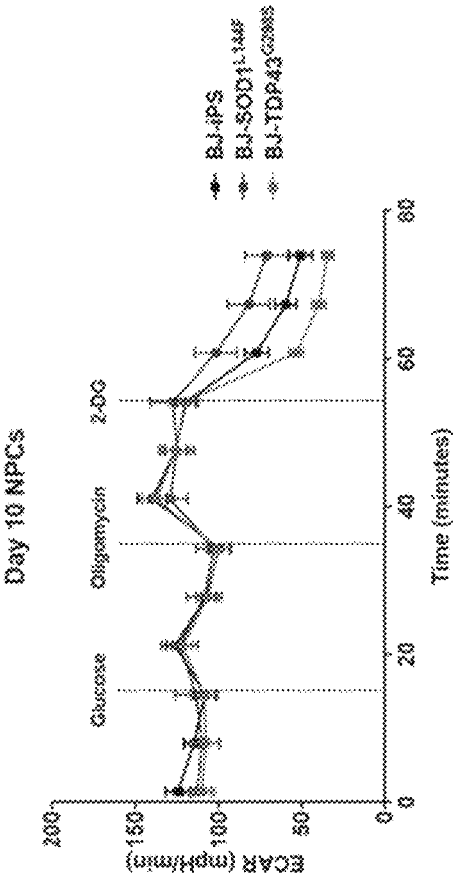
Figure 14H:
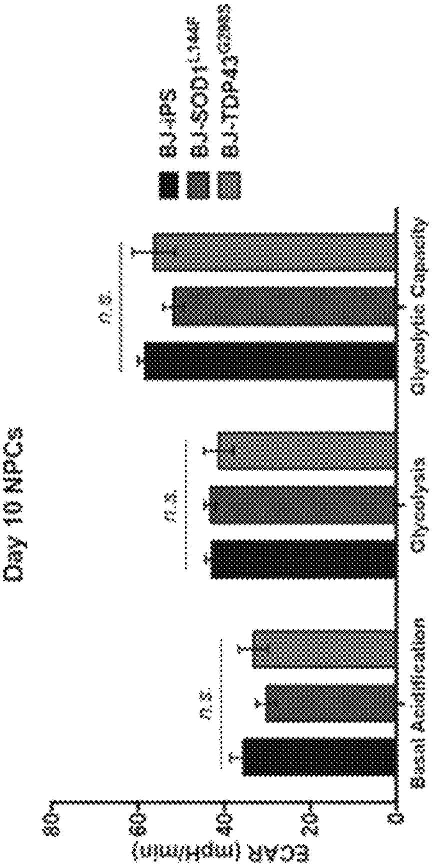

Since ATP production in diseased MNs is reduced by at least 25% in the various ALS lines, it was reasoned that these neurons would have to turn to other sources of energy to fuel their metabolic needs. To find out whether these neurons switch to glycolysis to meet their energy demands, extracellular acidification rate (ECAR) was measured and it was found that ALS MNs exhibited increased glycolysis and glycolytic capacity when compared to healthy MNs (FIGS. 2C, 2D), demonstrating a shift in cellular metabolism. Similarly, this shift of cellular metabolism from oxidative phosphorylation to glycolysis was recapitulated in BJ-$SOD1^{L144F}$ and BJ-$TDP43^{G298S}$ MNs compared to BJ-iPS MNs, revealing that this is an ALS specific metabolic feature rather than due to variation between cell lines (FIGS. 2C, 2D). To assess the specificity of these metabolic changes in MNs, OCR of day 10 NPCs was measured and it was found that ALS NPCs revealed no significant changes to the basal respiration and ATP-linked OCR. However, reduced spare respiratory capacity was reduced by approximately half in ALS NPCs (FIGS. 14C, 14D). Furthermore, glycolysis profiles of day 10 NPCs do not show significant changes between healthy and ALS cells (FIGS. 14E, 14F).

Figure 2E:
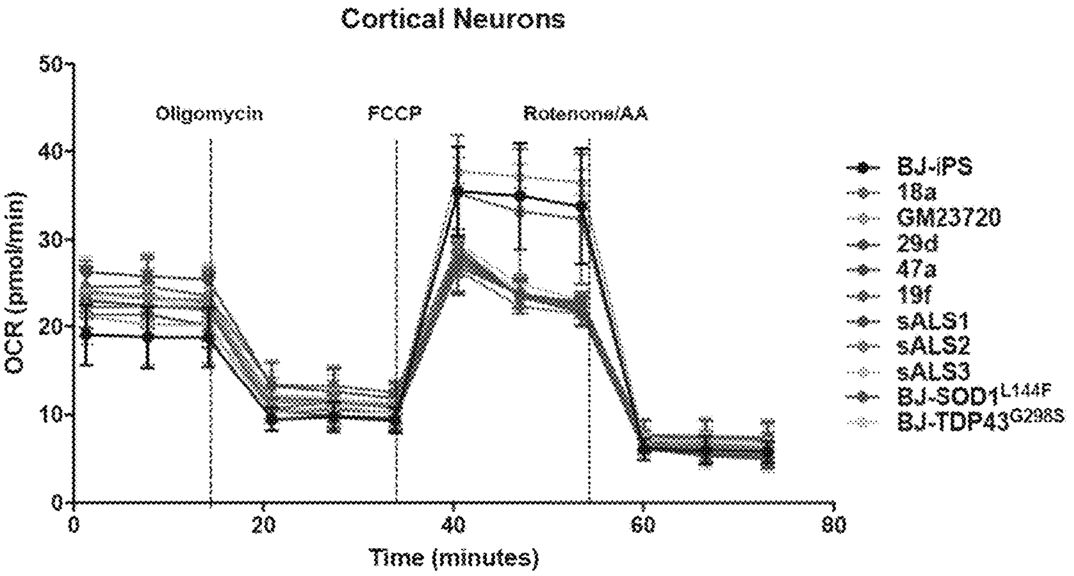
Figure 2F:
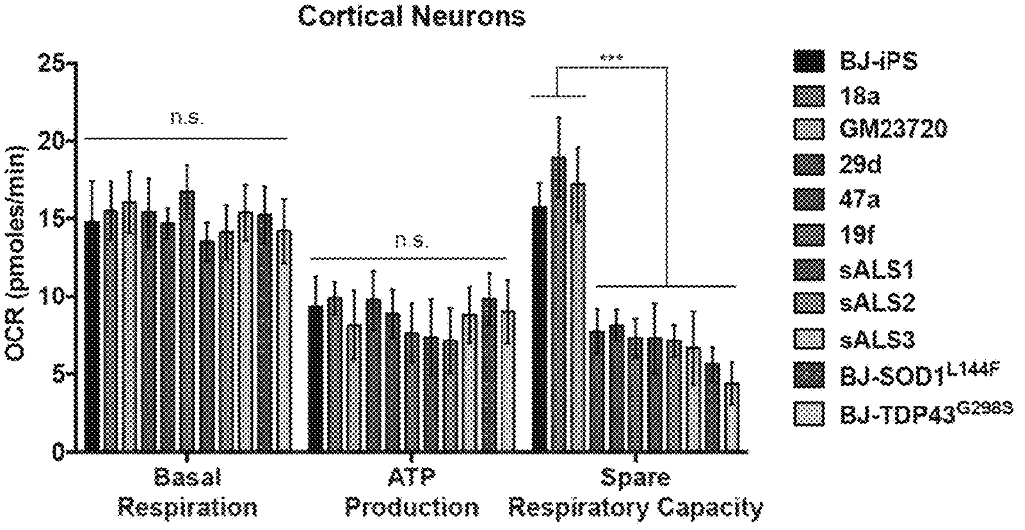
Figures 15A, 15B, 15C:
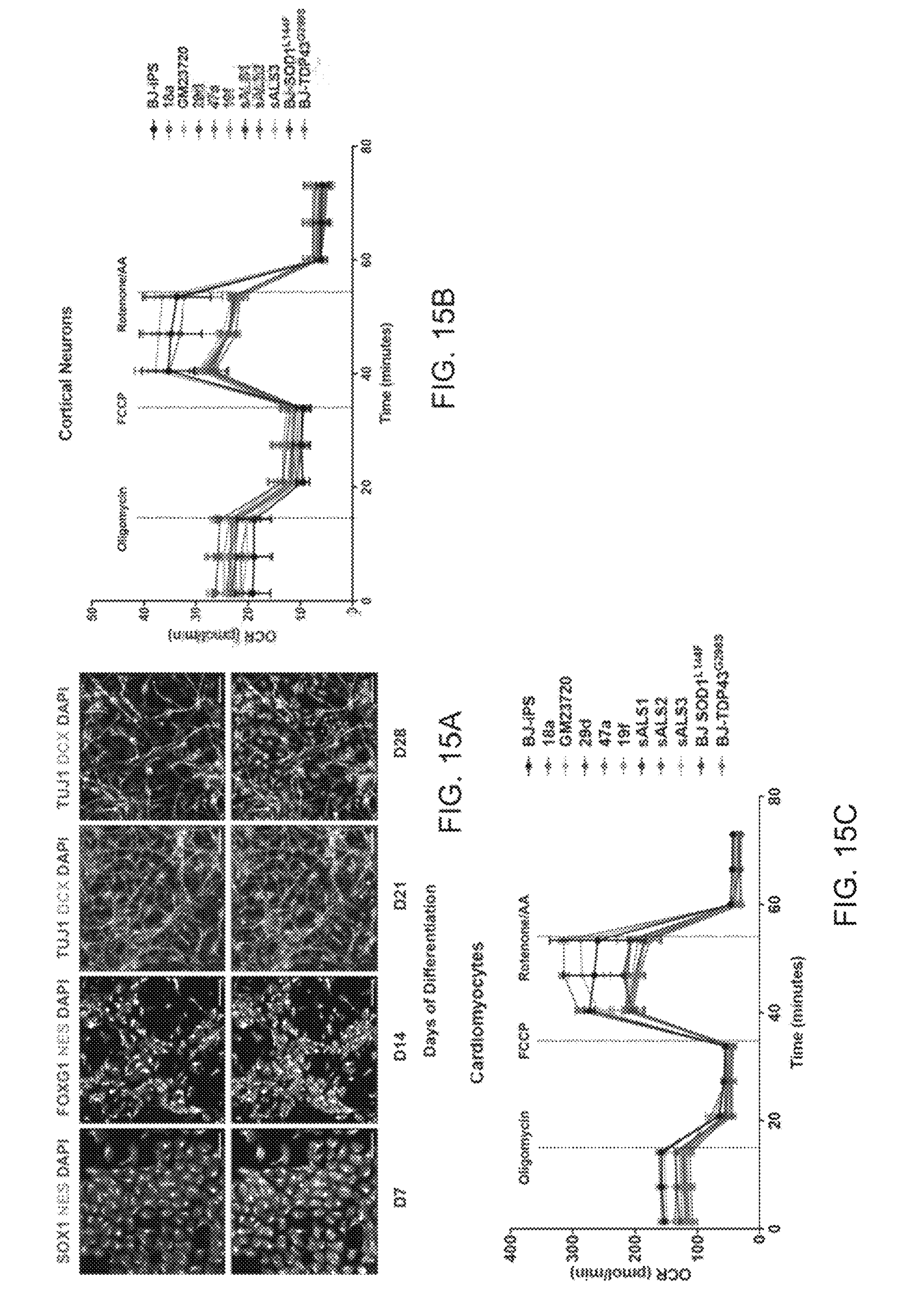
FIG. 15: Metabolic flux measurements in other metabolically active cell types reveal insignificant changes between ALS and healthy cells (Related to FIG. 3). (A) Immunostaining of iPSC-derived cultures at different timepoints of cortical neuron differentiation. Cellular nuclei were counterstained with DAPI. Scale bars, 50 μm. (B) OCR measurements using the MitoStress assay was performed and calculated for cortical neurons derived from healthy, ALS and diseased isogenic iPSCs at day 28. (C) OCR measurements using the MitoStress assay was performed and calculated for cardiomyocytes derived from healthy, ALS and diseased isogenic iPSCs at day 28. ***$p<0.001$, n.s. non-significant.

Other Metabolically Active Cell Types Derived from ALS iPSCs do not Show Overt Reduction in Mitochondrial Respiration Next, it was wondered if ALS-causing mutations affect all actively respiring cell types or specifically MNs. To this end, all iPSCs were differentiated towards $BRN2^{+}SATB2^{+}$ cortical neurons using a 28-day protocol (FIGS. 15A-15B). These neurons were then replated on 96-well plates for metabolic flux analyses. OCR measurements revealed that basal respiration and ATP production were not significantly different between BJ-$SOD1^{L144F}$ and BJ-$TDP43^{G298S}$ cortical neurons versus their isogenic BJ-iPS cortical neurons (FIGS. 2E, 2F). Likewise, cortical neurons derived from familial and sporadic ALS iPSCs do not show significant differences in basal respiration and ATP production compared to the 3 healthy controls. (FIGS. 2E. 2F) It was, however, noted that spare respiratory capacity is more than halved in all the ALS cortical neurons, which suggests that these cells may be more susceptible to metabolic stress.

Figure 2G:
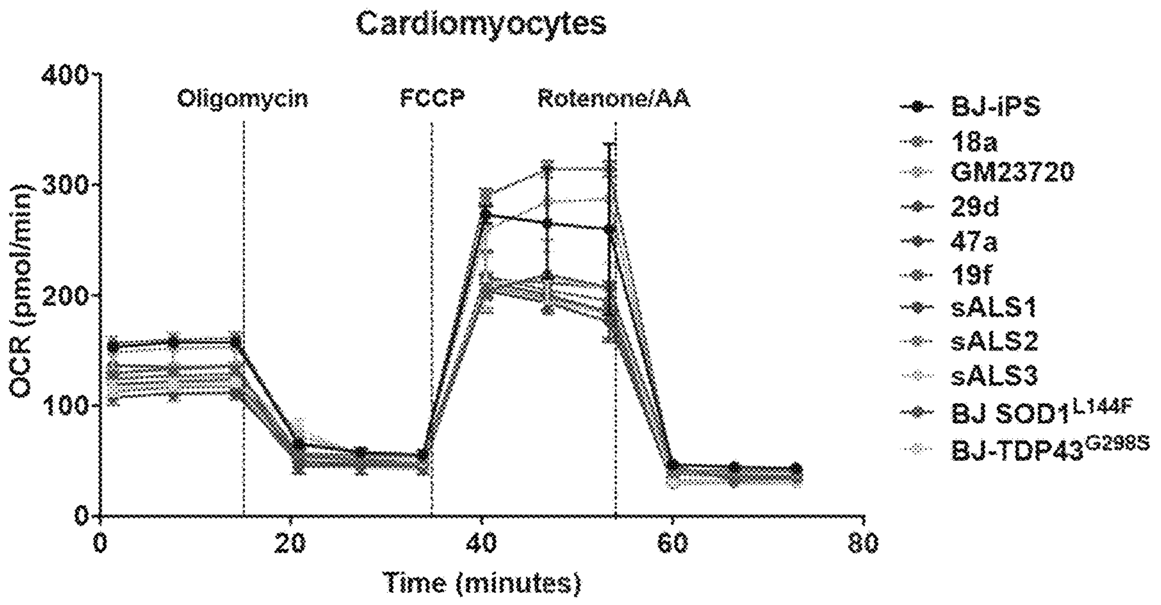
Figure 2H:
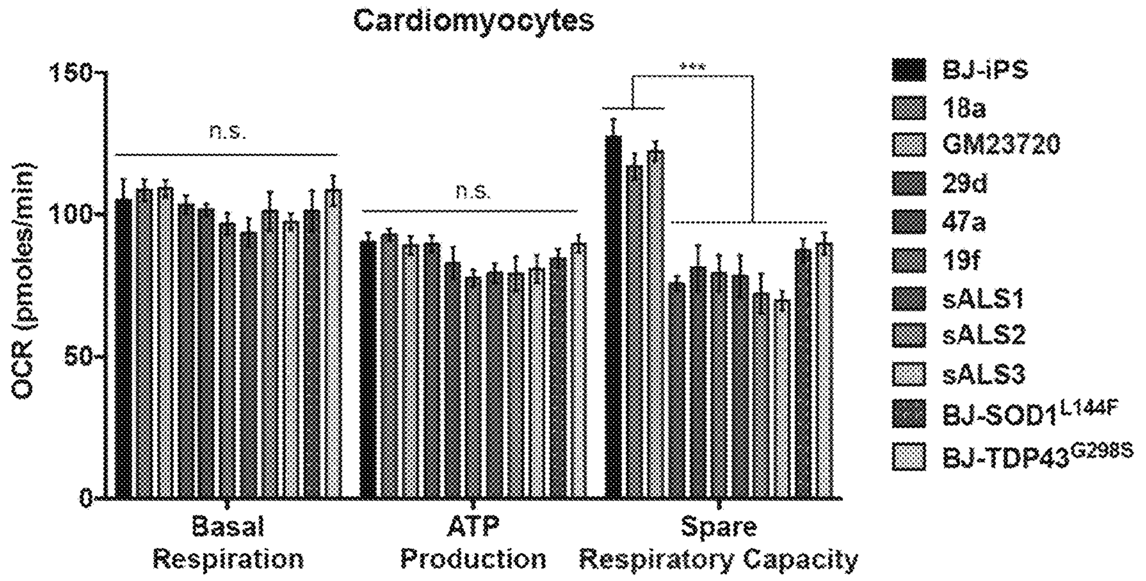

To investigate non-neural cell types, $cTnT^+$ cardiomyocytes were also derived from all the iPSCs (FIG. 15C) and metabolic flux analyses were performed. BJ-$SOD1^{L144F}$ and BJ-$TDP43^{G298S}$ cardiomyocytes were not significantly different from their isogenic healthy control in terms of basal respiration and ATP production, although total respiratory capacity was also reduced (FIGS. 2G. 2H). Likewise, similar results were also obtained for familial and sporadic ALS patient-derived cardiomyocytes (FIGS. 2G, 2H). Taken together, the results revealed that reduced mitochondrial respiration and the concomitant elevation of glycolysis is a metabolic hallmark of ALS MNs.

Figure 3A:
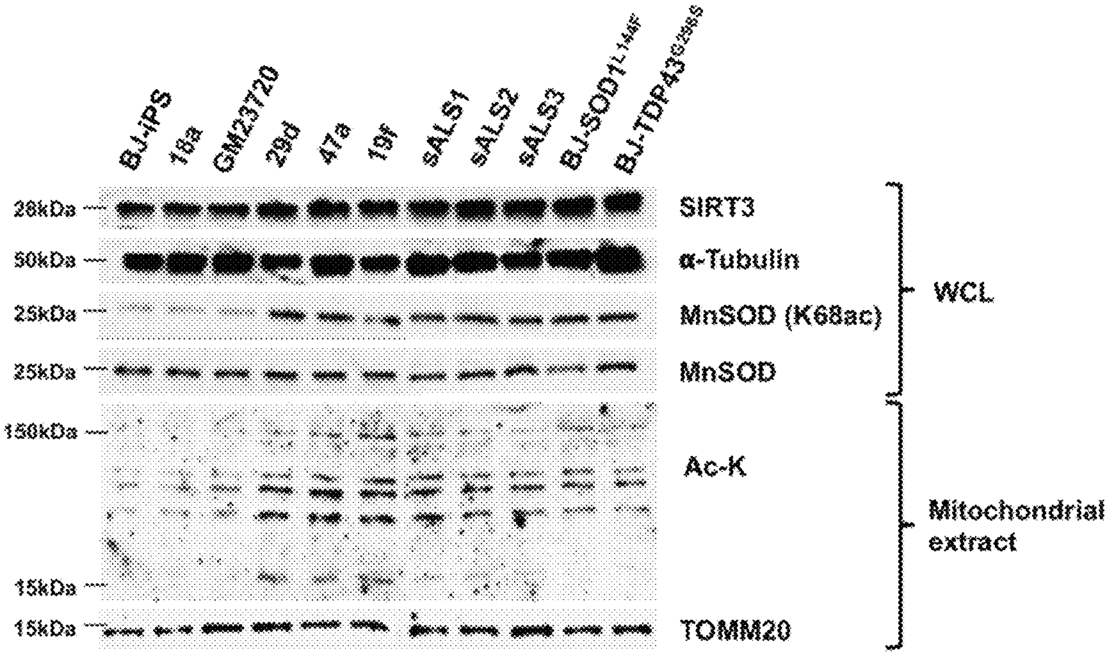
FIG. 3: Hyper-acetylation of mitochondrial proteins in familial and sporadic ALS MNs. (A) Western blot analyses of iPSC-derived MNs at day 28 probing for SIRT3, total MnSOD, MnSOD with specific acetylation at lysine-68 (MnSOD K68ac) on whole cell lysate as well as probing for acetyl-lysine proteins in purified mitochondrial extracts. (B) Densitometric analyses of Western blot bands reveal no significant changes in SIRT3 protein levels in ALS versus healthy MNs. (C) Densitometric analysis of MnSOD (K68ac) normalized to total MnSOD revealed approximately 5-fold upregulation of MnSOD(K68ac) in all of the ALS iPSC-derived MNs. This indicates reduced SIRT3 activity in ALS MNs. (D) Immunohistochemistry of control and sporadic ALS patients (SALS) lumbar sections revealed increased MnSOD (K68ac) signals in SALS patients lumbar motor neurons (arrow). Lipofuscin is visible in large, healthy motor neurons, a function of normal cellular aging and unrelated to disease (*). Scale bars, 2.5 mm (left panel) and 100 μm (right panel). (E) Quantification of MnSOD (K68ac) signals in both control (n=380) and SALS (n=216) lumbar motor neurons demonstrates increased MnSOD (K68ac) signals in SALS patients. (F) Densitometric analysis of acetyl-lysine signals normalized to TOMM20 revealed approximately 3-fold increase in acetylation of mitochondria proteins in all of the ALS iPSC-derived MNs. (G) Complex I activity in healthy and ALS MNs were measured, which revealed significant decline of between 30 to 80% in the ALS MNs. *$p<0.05$, $p<0.01$, *$p<0.001$, n.s. non-significant; two-tailed t test.
Figure 3B:
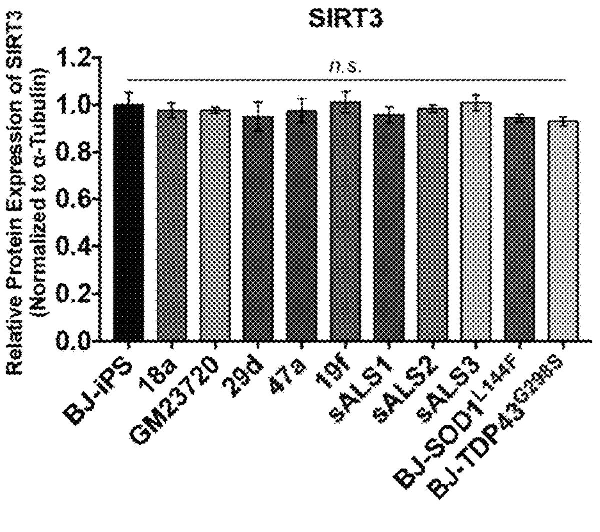
Figure 3C:
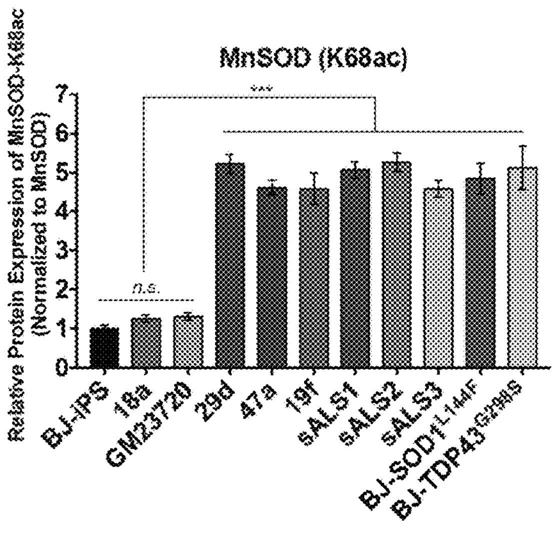
Figure 3D:
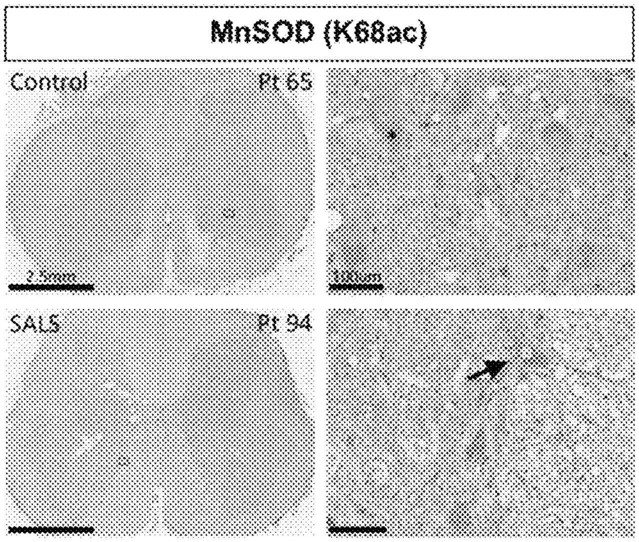
Figure 3E:
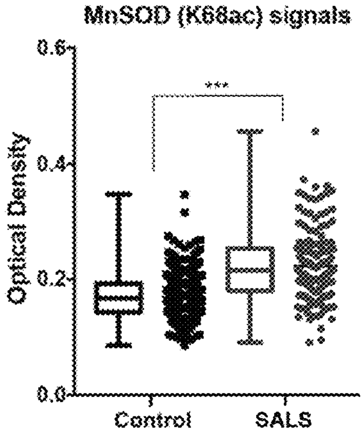
Figure 3F:
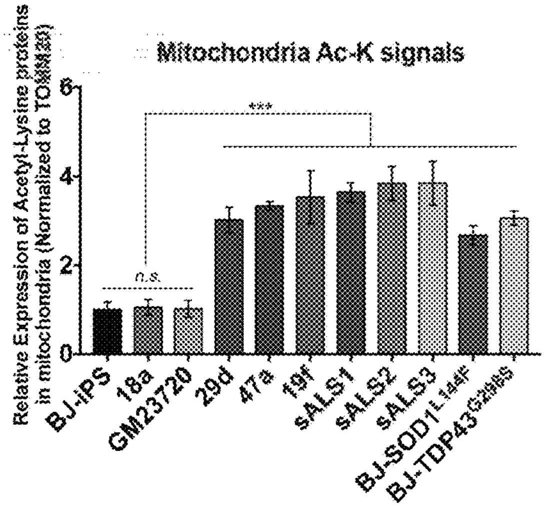
Figure 3G:
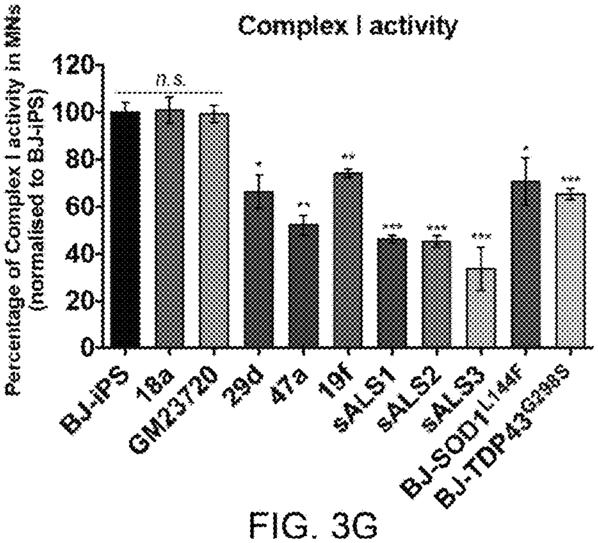

ALS MN Metabolic Defects Associated with Hyper-Acetylation of Mitochondrial Proteins Having established that mitochondrial respiration defects are common, and unique to both familial and sporadic ALS, it was sought to understand the mechanisms that underlie these defects. Mitochondrial respiration is known to be fine-tuned by the acetylation of mitochondrial proteins, and this process is controlled by the mitochondrial deacetylase SIRT3 as well as GCN5L1, the proposed acetyltransferase that catalyzes the reverse reaction. Since it has been shown that SIRT3 depletion leads to mitochondrial protein hyper-acetylation in muscles, cardiac and liver tissues, it was investigated if the loss of SIRT3 resulted in the ALS-specific metabolic defects observed. However, Western blot analysis did not reveal significant changes in SIRT3 levels between healthy and ALS MNs or MNs from the set of isogenic iPSC lines (FIGS. 3A, 3B). It was postulated that SIRT3 activity could be affected even though expression levels were unchanged. Therefore, to determine SIRT3 activity, relative acetylation of lysine 68 on MnSOD (MnSOD K68ac), one of the best-characterized SIRT3 target, was measured. Indeed, Western blot analyses revealed much higher MnSOD K68ac in all of the ALS MN cultures, including the sporadic ALS MNs and isogenic MNs, compared to healthy controls, suggesting reduced SIRT3 activity (FIGS. 3A, 3C). Human post-mortem lumbar spinal cord sections were also analyzed by immunohistochemistry, which confirmed higher MnSOD K68ac signals in alpha MNs of lumbar spinal cord in sporadic ALS patients compared with non-ALS controls (FIGS. 3D, 3E). Since SIRT3 has multiple targets in the mitochondria, it is expected that loss of SIRT3 activity would impact global mitochondrial acetylation. To confirm this, mitochondrial extracts were harvested from all the iPSC-derived MNs and immunoblotting of acetylated proteins was performed using a specific antibody against acetyl-lysine. Western blot analysis revealed significantly higher intensities of acetylated proteins in all of the ALS lines compared to the healthy controls, concurring with the MnSOD K68ac assay (FIGS. 3A, 3F). SIRT3 interactome studies have revealed several Complexes I subunits amongst its downstream target. Expanding on these studies, it was found that reduced Complex I activity was observed in all of the ALS MNs (FIG. 3G), which explained the lower basal mitochondrial respiration observed in these ALS MNs (FIG. 2).

Loss of SIRT3 Function Mimics ALS Phenotypes

Figure 4A:
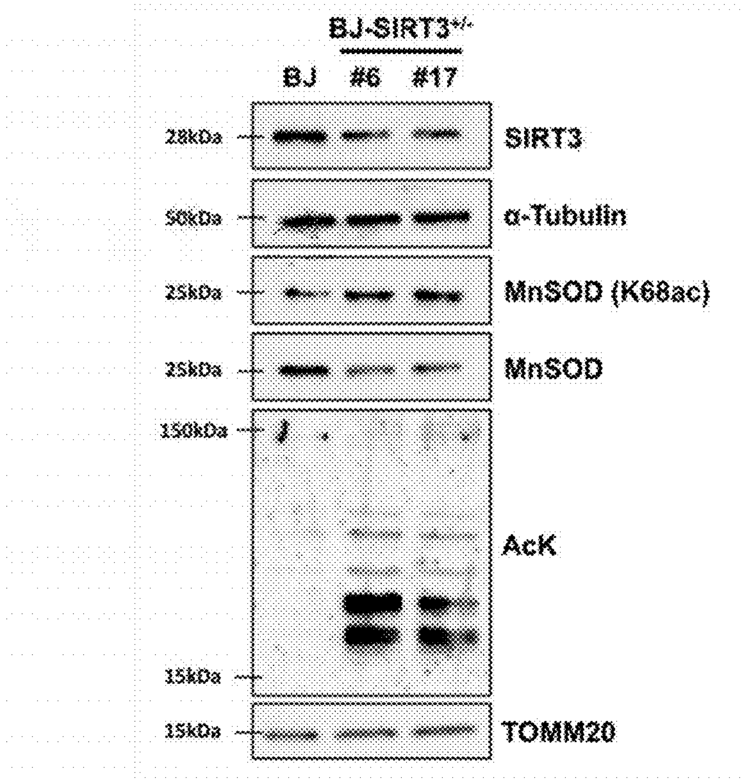
FIG. 4: SIRT3 deficiency in MNs results in ALS-like phenotypes. (A) Western blot analysis of day 28 MNs derived from BJ-iPS and two isogenic $SIRT3^{+/-}$ (#6 and #17) clones confirmed reduction in SIRT3 protein, along with increased MnSOD (K68ac) and increased acetylation of mitochondrial proteins. (B) Densitometric analyses of Western blot bands reveal 50% decrease in SIRT3 protein levels and increased MnSOD (K68ac) in both $SIRT3^{+/-}$ #6 and #17 versus healthy MNs. (C) qPCR measurements of CHOP and sXBP1 show significant upregulation of both ER stress transcripts in $SIRT3^{+/-}$ #6 and #17 relative to the isogenic BJ-iPS control. (D) Measurements of OCR using the MitoStress assay of day 28 MNs differentiated from BJ-iPS, $SIRT3^{+/-}$ #6 and #17. (E) Measurements of basal respiration, ATP production and spare respiration of day 28 MNs differentiated from BJ-iPS, $SIRT3^{+/-}$ #6 and #17. (F) Measurements of ECAR using the Glycolysis Stress assay of day 28 MNs differentiated from BJ-iPS, $SIRT3^{+/-}$ #6 and #17. (G) Measurements of basal acidification, glycolysis and glycolytic capacity of day 28 MNs differentiated from BJ-iPS, $SIRT3^{+/-}$ #6 and #17. (H) Quantification of $ISL1^+$ MNs derived from both BJ-$SIRT3^{+/-}$ clones from day 25 to day 35 revealed a progressive death phenotype as compared to its healthy control (BJ-iPS). (I) Representative images of $ISL1^+SM132^+$ MNs derived from BJ-iPS, BJ-$SIRT3^{+/-}$ #6 and #17 iPSCs, showing cell body sizes (outlined in white dotted lines) from MNs at day 28, and at day 31. Scale bars, 50 μm. (J) Quantification of mean cell body size and number of primary neurites of both BJ-$SIRT3^{+/-}$ clones reveal deteriorating neuronal health from day 28 to day 31. $p<0.01$, *$p<0.001$, n.s. non-significant; two-tailed t test.
Figure 4B:
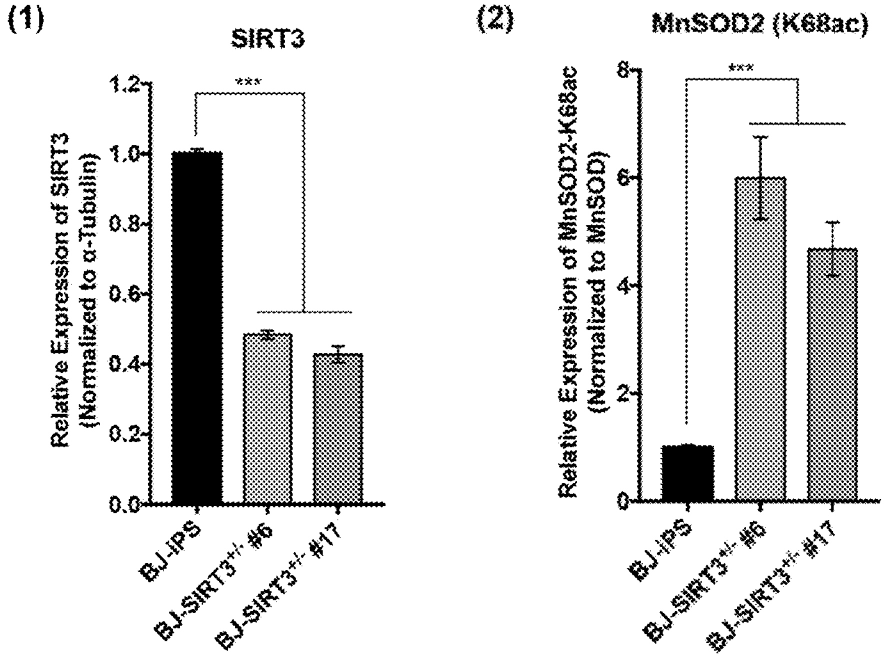
Figure 4C:
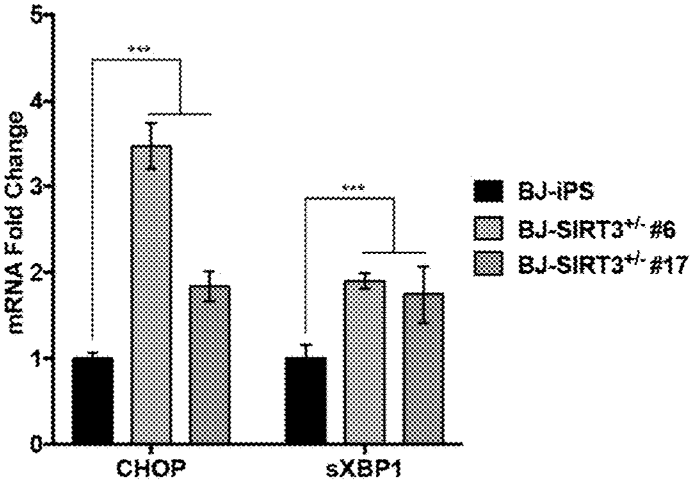
Figure 4D:
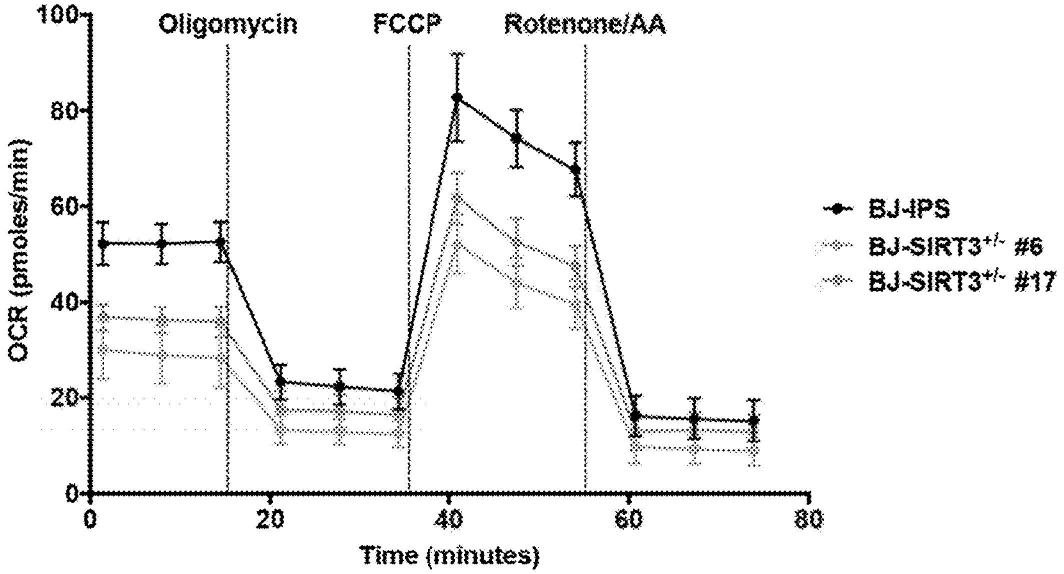
Figure 4E:
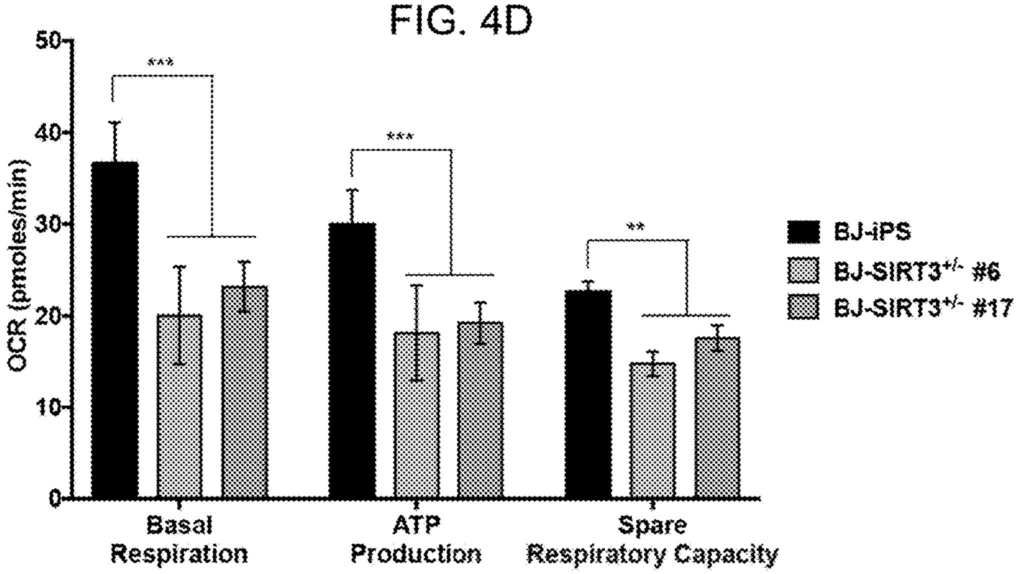
Figure 4F:
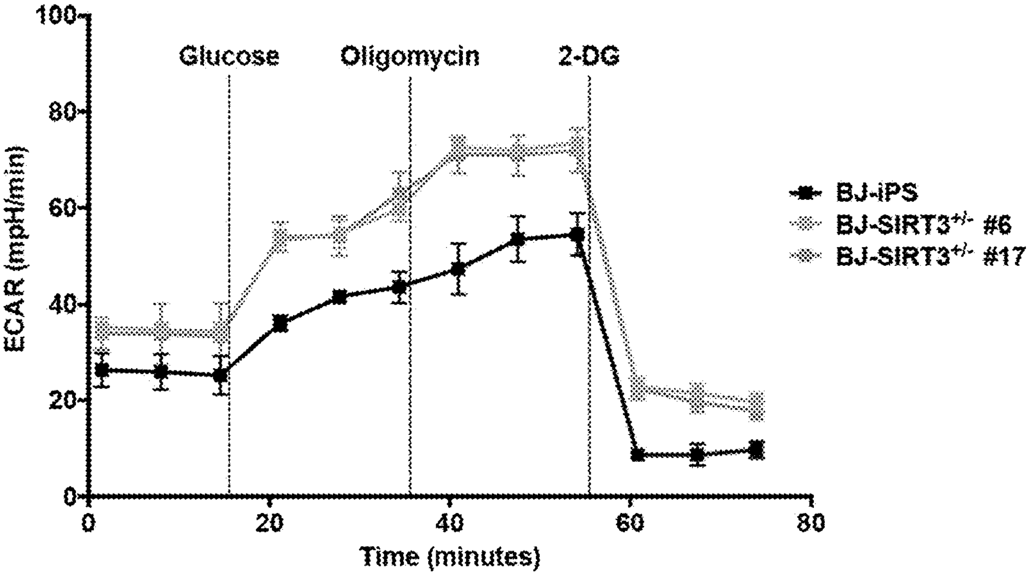
Figure 4G:
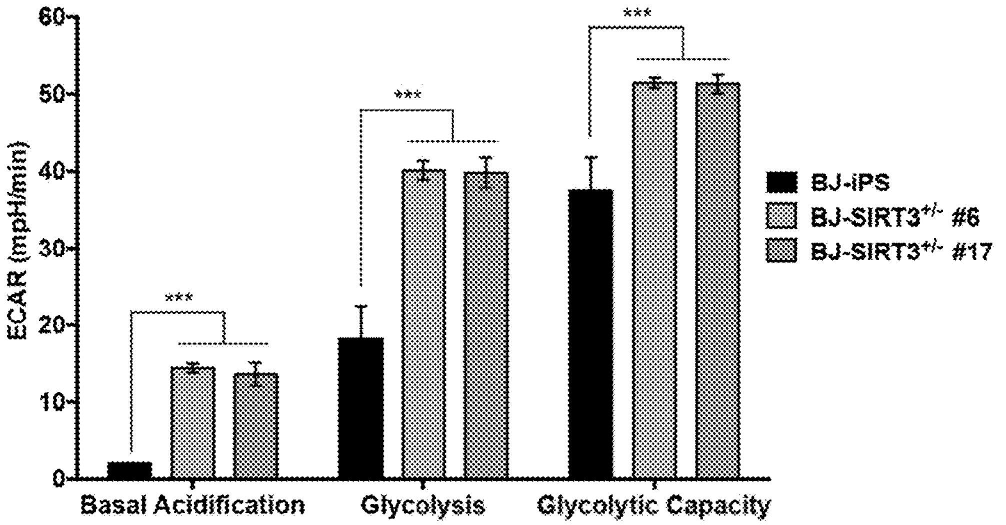
Figure 4H:
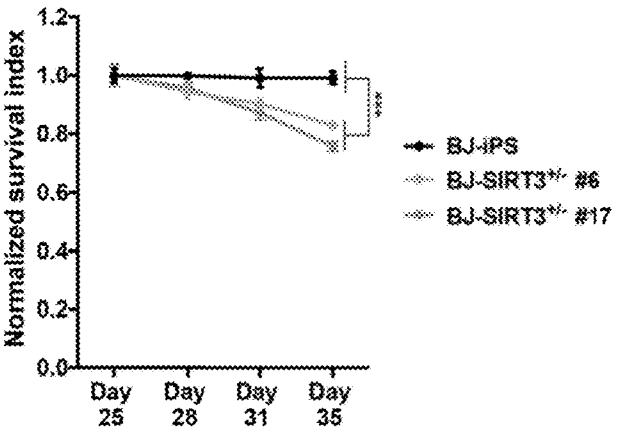
Figure 4I:
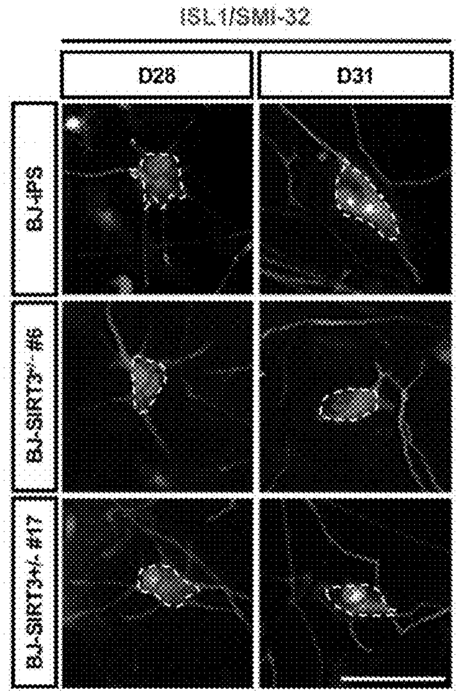
Figure 4J:
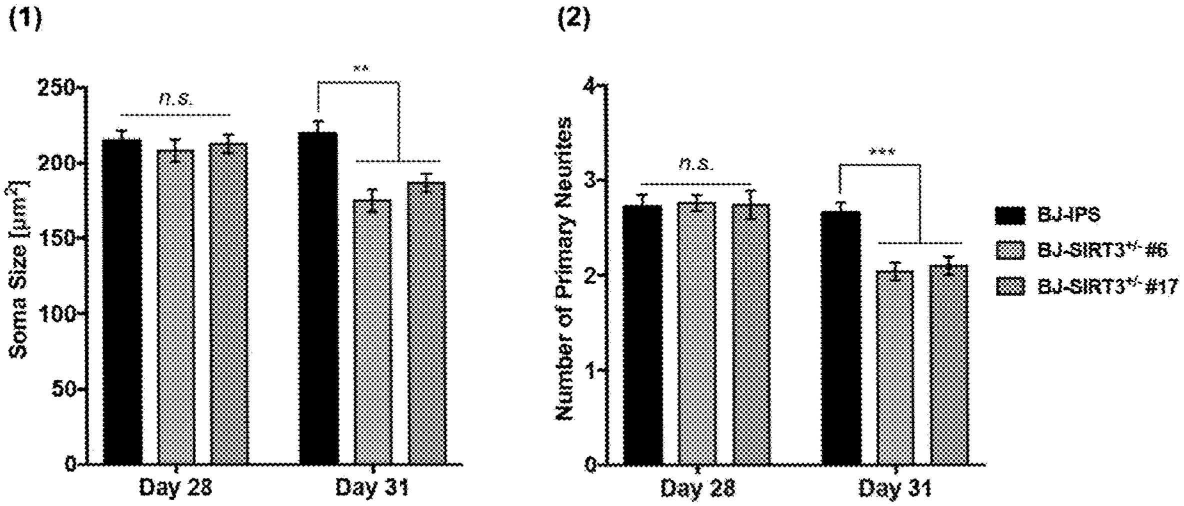
Figure 13C:
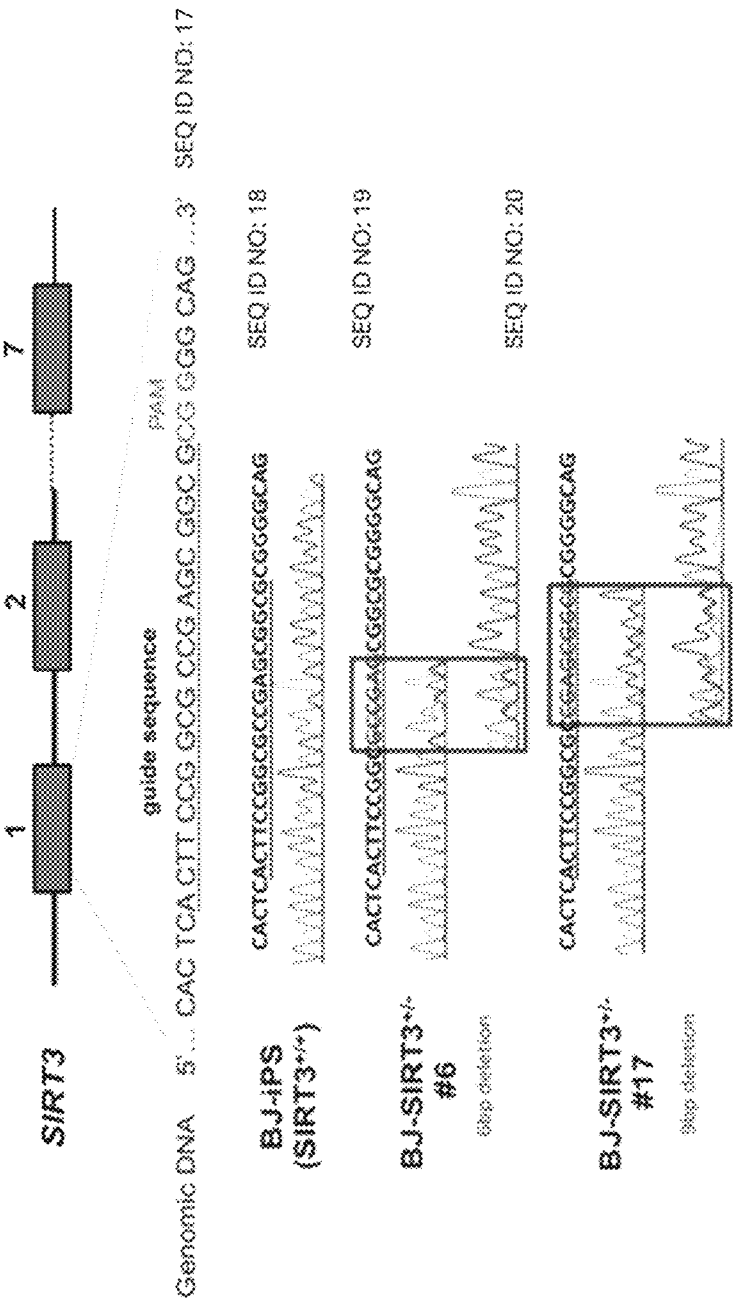
Figure 13D:
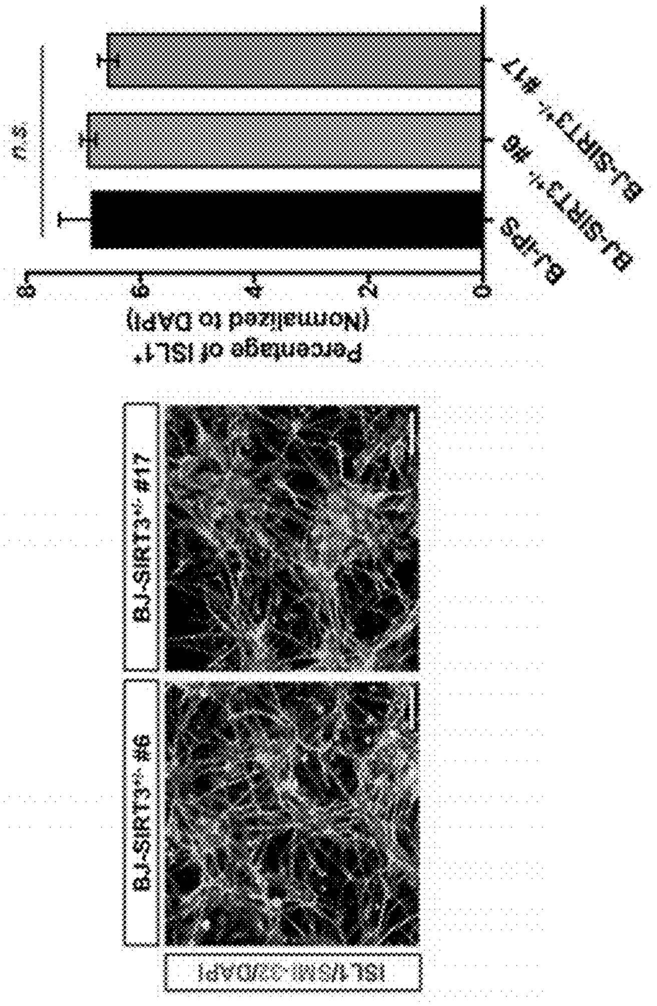

To assess the function of SIRT3 in regulating mitochondrial bioenergetics, genetic models of SIRT3 depletion were created and RNA interference was performed to study effects of SIRT3 depletion on MN survival and function. Using the CRISPR/Cas9 approach, multiple isogenic SIRT3 haploinsufficient ($SIRT3^{+/-}$) iPSC lines were generated (FIG. 13C). Out of 66 clones that were screened in total, 31 were heterozygous knockouts (47%) while none of them were total knockouts, suggesting that SIRT3-deficient iPSCs were unviable. $SIRT3^{+/-}$ clones #6 and #17 were randomly selected and it was showed that both clones differentiated into MNs with approximately the same efficiencies as the isogenic control BJ-iPS (FIG. 13D). Both BJ-$SIRT3^{+/-}$ #6 and #17 were verified by Western blot to show a 50% reduction of SIRT3 protein. MnSOD K68ac levels were also significantly higher in BJ-$SIRT3^{+/-}$ #6 and #17, suggesting that SIRT3 is important in regulating acetylation status of mitochondrial proteins (FIGS. 4A, 4B). Furthermore, purified mitochondrial extracts also showed that clones #6 and #17 had more acetyl-lysine residues (FIG. 4A), consistent with the hyper-acetylated mitochondrial profiles seen in the ALS iPSC-derived MNs (FIG. 3A). A constellation of in vitro ALS phenotypes has been shown, which includes accelerated MN death, elevated ER stress signaling, smaller cell bodies and a hypo-oxidative/hyper-glycolytic metabolic profile (FIG. 2). Therefore, it was sought to determine if loss of SIRT3 could induce ALS phenotypes in vitro. Measurements of ER stress transcripts in the day 28 MNs from both $SIRT3^{+/-}$ clones revealed significant upregulation of CHOP and sXBP1 mRNAs (FIG. 4C), similar to that seen in all the ALS MNs tested (FIG. 1D). Metabolic flux measurements confirmed that MNs derived from both $SIRT3^{+/-}$ clones exhibited reduced mitochondrial respiration (FIGS. 4D, 4E) and elevated glycolysis simultaneously (FIGS. 4F, 4G). Phenotypically, motor neurons derived from both $SIRT3^{+/-}$0 clones had reduced survival (FIG. 4H) and significantly reduced soma sizes and primary neurites at day 31 (FIGS. 4I, 4J). Given that $SIRT3^{+/-}$ MNs display ALS-like phenotypes, this suggests that partial loss of SIRT3 activity contributes to ALS pathogenesis.

Figure 16A:
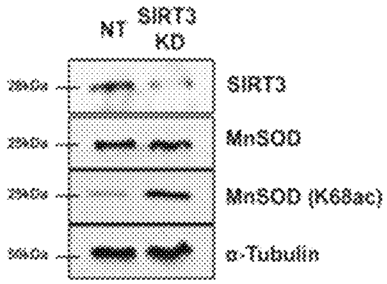
FIG. 16: SIRT3 activation or GCN5L1 inhibition reverses disease phenotypes in ALS MNs (Related to FIG. 5). (A) Western blot analyses at day 28 confirming SIRT3 knockdown and increased MnSOD (K68ac) levels in si-SIRT3 conditions. (B) Densitometric analyses of Western blot bands reveal significant increase in MnSOD (K68ac) levels in si-SIRT3 conditions. (C) Measurements of basal respiration, ATP production and spare respiration of neurons in si-NT (dark grey) and si-SIRT3 (light grey) conditions. (D) Measurements of intracellular $NAD^+$:NADH ratio in healthy and ALS MNs revealed reduced $NAD^+$ availability in ALS MNs. (E) Measurement of soma size and primary neurites show overall improvement in neuronal morphology in NAM supplemented ALS MNs. (F) Western blot analyses at day 31 confirming SIRT3 overexpression in ALS MNs did not reduce MnSOD (K68ac) levels, further validating that SIRT3 activity is affected in ALS MNs. (G-I) Measurements of basal respiration, ATP production and spare respiration of neurons in control (black) and SIRT3 overexpressing (grey) conditions. (J) qPCR quantification of GCN5L1 transcripts in GCN5L1 knockdown MN cultures at day 31. Fold changes are normalized to non-targeting MN cultures. (K) Measurement of soma size and primary neurites show overall improvement in neuronal morphology in GCN5L1 knockdown ALS MNs. *$p<0.05$, $p<0.01$, *$p<0.001$, n.s. non-significant.
Figure 16B:
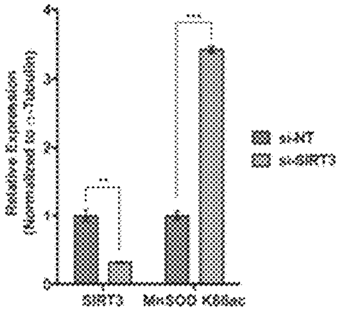
Figure 16C:
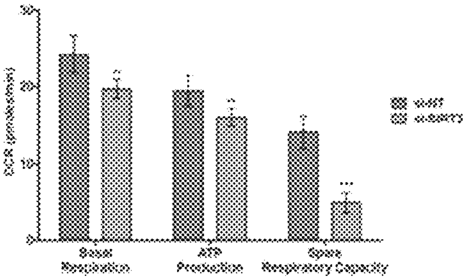

Next, to confirm the earlier findings with $SIRT3^{+/-}$ MNs, small interfering RNA (siRNA)-mediated knockdown was performed to transiently deplete SIRT3 levels in healthy BJ-iPS MNs at day 25. At day 28, 70% knockdown at both mRNA and protein levels was confirmed, together with increased MnSOD K68ac, indicative of decreased SIRT3 activity (FIGS. 16A, 16B). Analyses of these neurons at day 28 also revealed reduced OCR parameters (FIG. 16C). Taken together, these results suggest that SIRT3 is important in maintaining mitochondrial bioenergetics in MNs and depletion of SIRT3 leads to ALS-like phenotypes.

SIRT3 Activation or GCN5L1 Inhibition Improves Metabolic Defects in ALS MNs

Figure 5A:
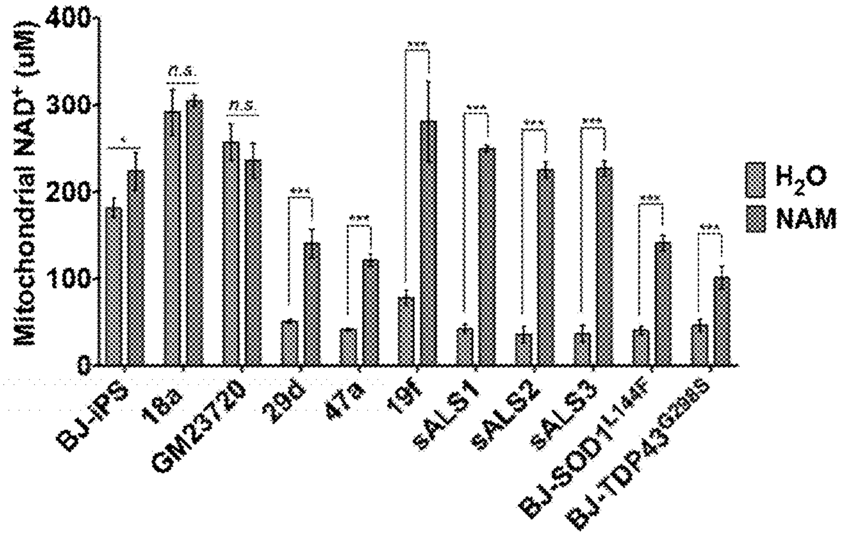
FIG. 5: NAM supplementation reverses mitochondrial respiration defect and improves neuronal morphology in ALS MNs. (A) Measurements of mitochondrial $NAD^+$ levels in healthy and ALS MNs after NAM supplementation revealed increased mitochondrial $NAD^+$ availability in ALS MNs. (B) WT and ALS iPSC-derived MNs were treated with either $H_2O$ or NAM from day 28 to day 35. Number of $ISL1^+$ MNs were quantified and normalized to number of $ISL1^+$ MNs in respective cell lines at day 28. NAM supplementation prevents MN death in ALS MNs. (C-E) Measurements of basal respiration, ATP production and spare respiration respectively in healthy and ALS MNs treated with water as a control or 0.5 mM NAM. (F) Representative images of $ISL1^+SM132^+$ MNs of BJ-$SOD1^{L144F}$ and BJ-$TDP43^{G298S}$ illustrating NAM supplementation promotes healthier neuronal morphologies. MN cell body sizes are outlined by white dotted lines. Scale bars, 50 μm. (G) Measurement of soma size and primary neurites show overall improvement in neuronal morphology in NAM supplemented ALS MNs. ***$p<0.001$, n.s. non-significant; two-tailed t test.
Figure 5B:
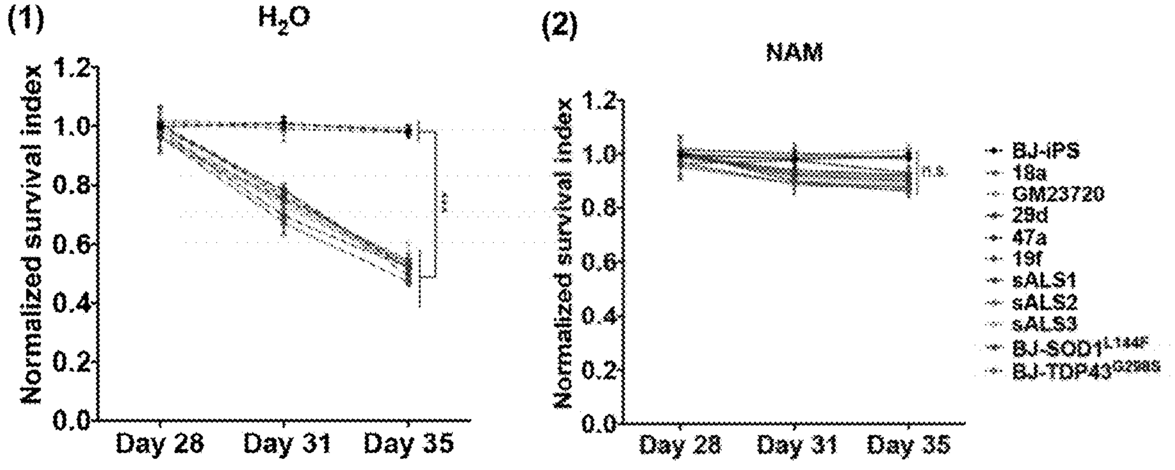
Figure 5C:
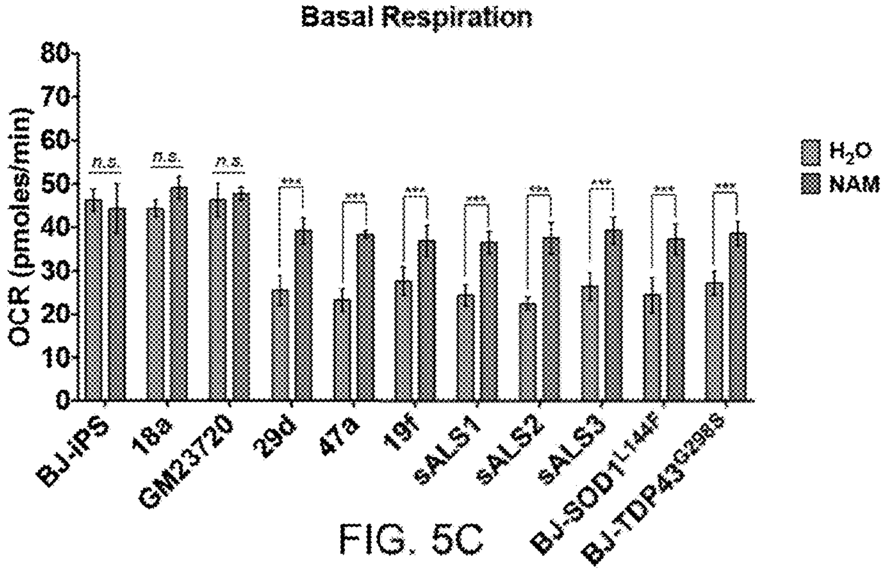
Figure 5D:
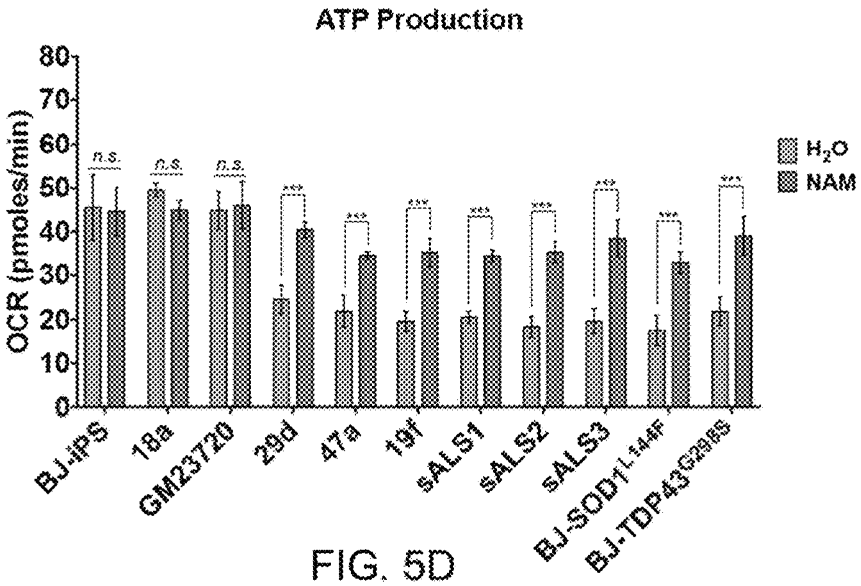
Figure 5E:
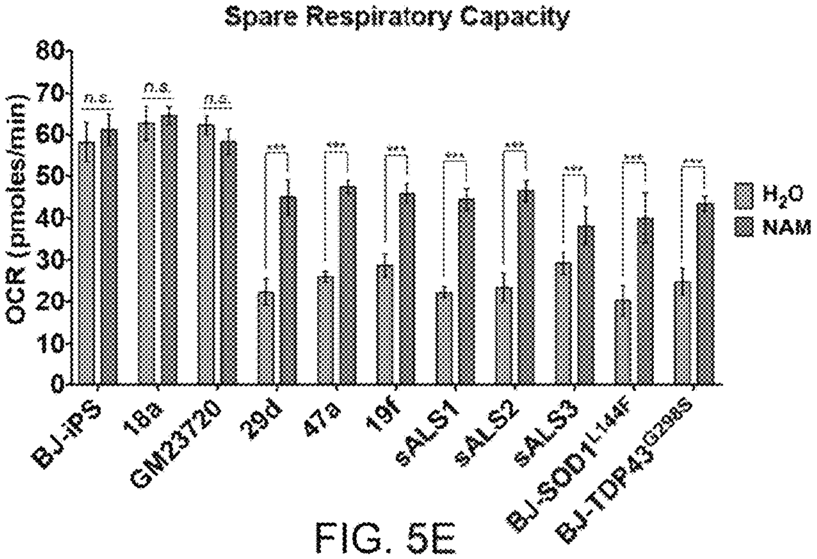
Figure 5F:
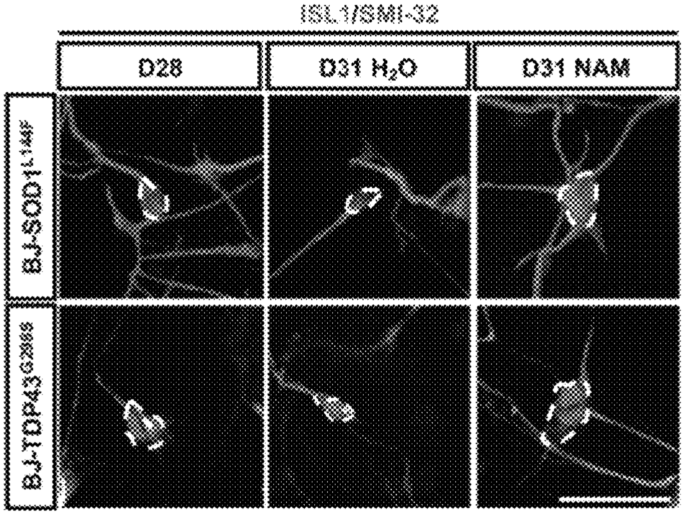
Figure 5G:
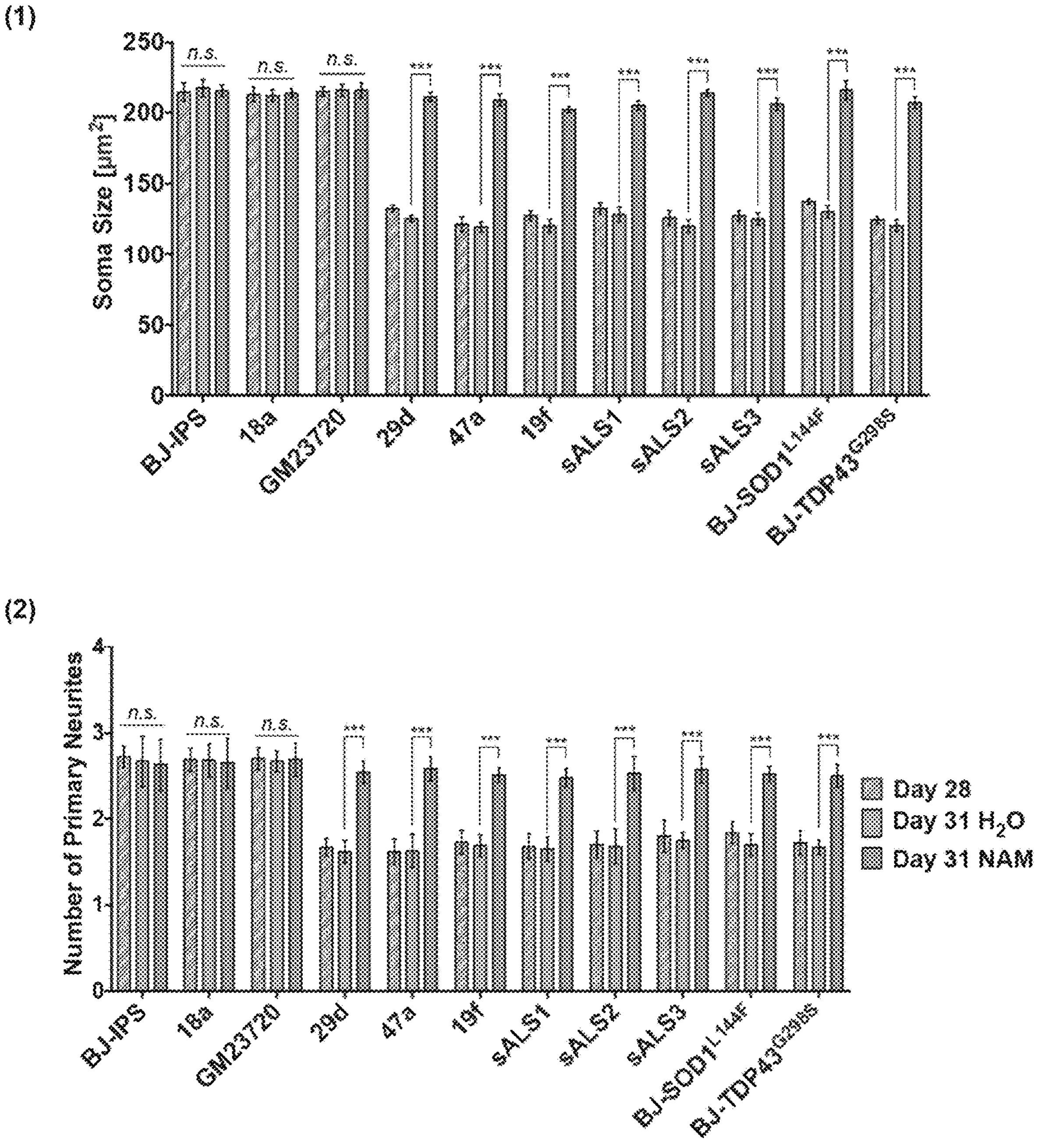

Since SIRT3 is a $NAD^+$-dependent deacetylase, one possibility for reduction in SIRT3 activity is insufficient levels of mitochondrial $NAD^+$ in ALS MNs. To investigate this, $NAD^+$ levels were measured in isolated mitochondria extracted from iPSC-derived MNs and it was found that there was 60-80% reduction in $NAD^+$ levels in the mitochondria of sporadic, familial and isogenic ALS MNs when compared to healthy controls (FIG. 5A). Using 0.5 mM Nicotinamide (NAM), a precursor of $NAD^+$, it was demonstrated that mitochondrial $NAD^+$ levels were significantly elevated in ALS MNs (FIG. 5A) and promoted ALS MN survival (FIG. 5B). NAM supplementation increased mitochondrial NAD+ levels in ALS MNs (FIG. 5A), leading to significantly improved basal mitochondrial respiration, ATP production as well as spare respiratory capacity (FIGS. 5C-E). It is worth pointing out that NAM supplementation did not elevate mitochondrial $NAD^+$ levels and had no significant effects on mitochondrial respiration of healthy MNs, indicating targeted rescue of ALS MNs. Moreover, addition of exogenous NAM to cell culture media was able to promote healthier neuronal morphologies similar to that of wild-type MNs (FIGS. 5F, 5G).

Figure 16D:
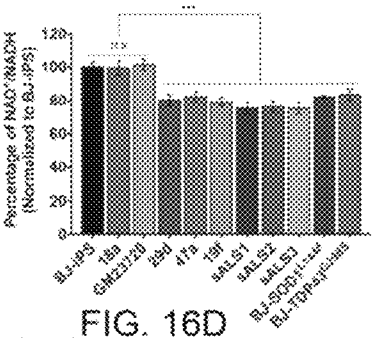
Figure 16E:
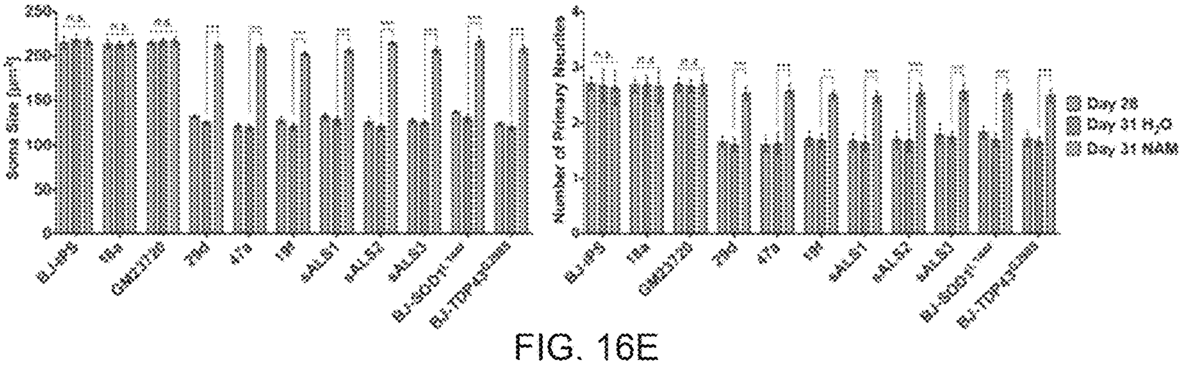

Next, it was wondered if overexpression of SIRT3 could improve ALS MN metabolic defects. Using either an inducible SIRT3-expressing lentivirus or control GFP virus, all the iPSC-derived MNs were infected at day 28 and harvested at day 31 for analyses. By means of immunoblotting, it was verified that SIRT3 is reliably over-expressed in both healthy and ALS iPSC-derived MNs, but MnSOD K68ac signals were not reduced in the SIRT3 over-expressing ALS MNs (FIG. 16D). Of note, SIRT3 over-expression significantly improved basal respiration, ATP production and spare respiratory capacity in healthy MNs but has no significant effects in the ALS MNs (FIGS. 16E-G), confirming the earlier results that SIRT3 activity rather than expression is limiting in the ALS MNs. Therefore, it is not surprising that simply over-expressing SIRT3 without the addition of NAM or other $NAD^+$ precursors would have no significant effects on mitochondrial respiration in ALS MNs.

Figure 8:
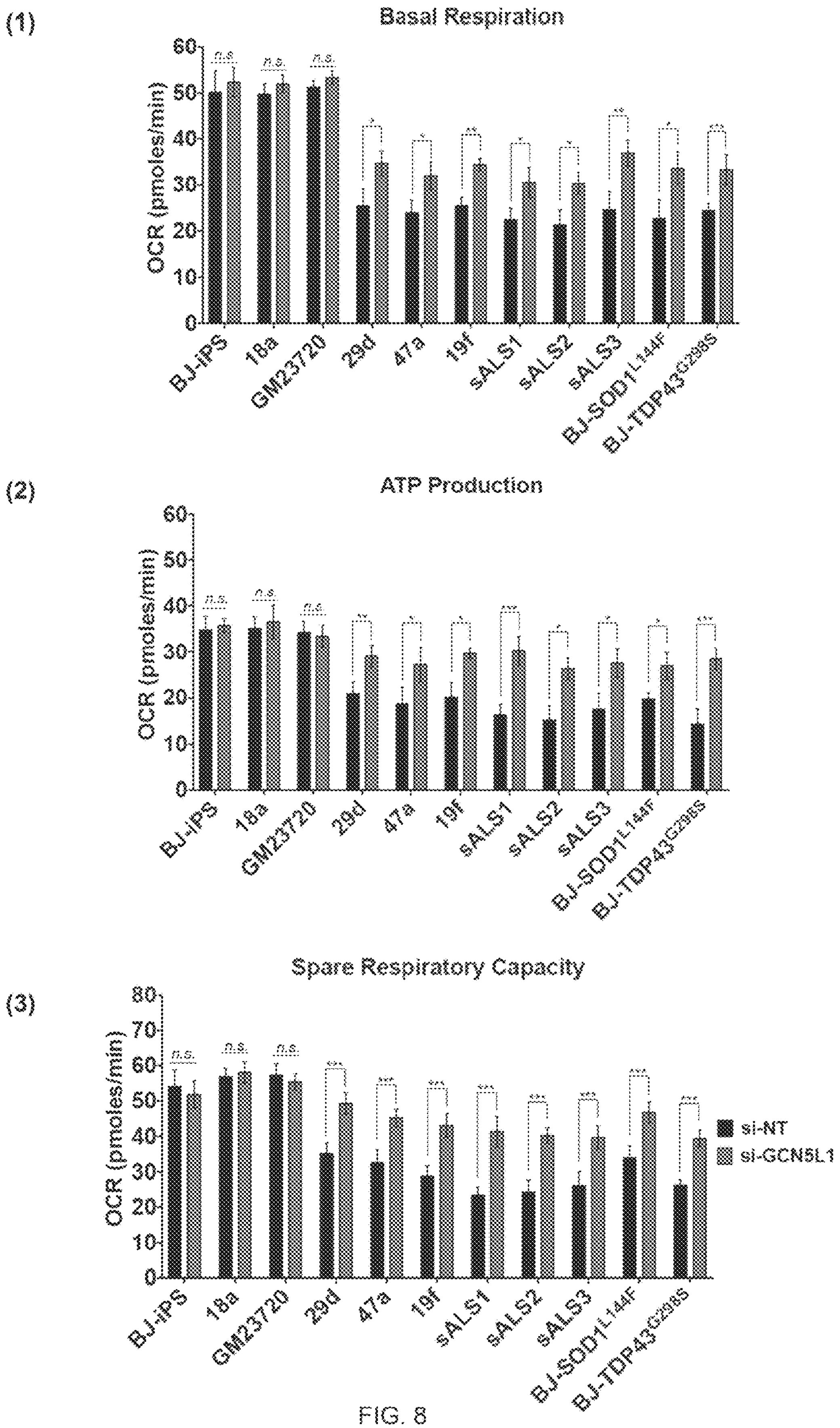
FIG. 8: GCN5L1 knockdown rescued ATP production reverses metabolic defects in ALS MNs. Measurements of basal respiration, ATP production and spare respiration respectively in healthy and ALS MNs treated with non-targeting and GCN5L1 siRNA, showing that GCN5L1 knockdown rescued ATP production back to healthy levels.
Figure 9:
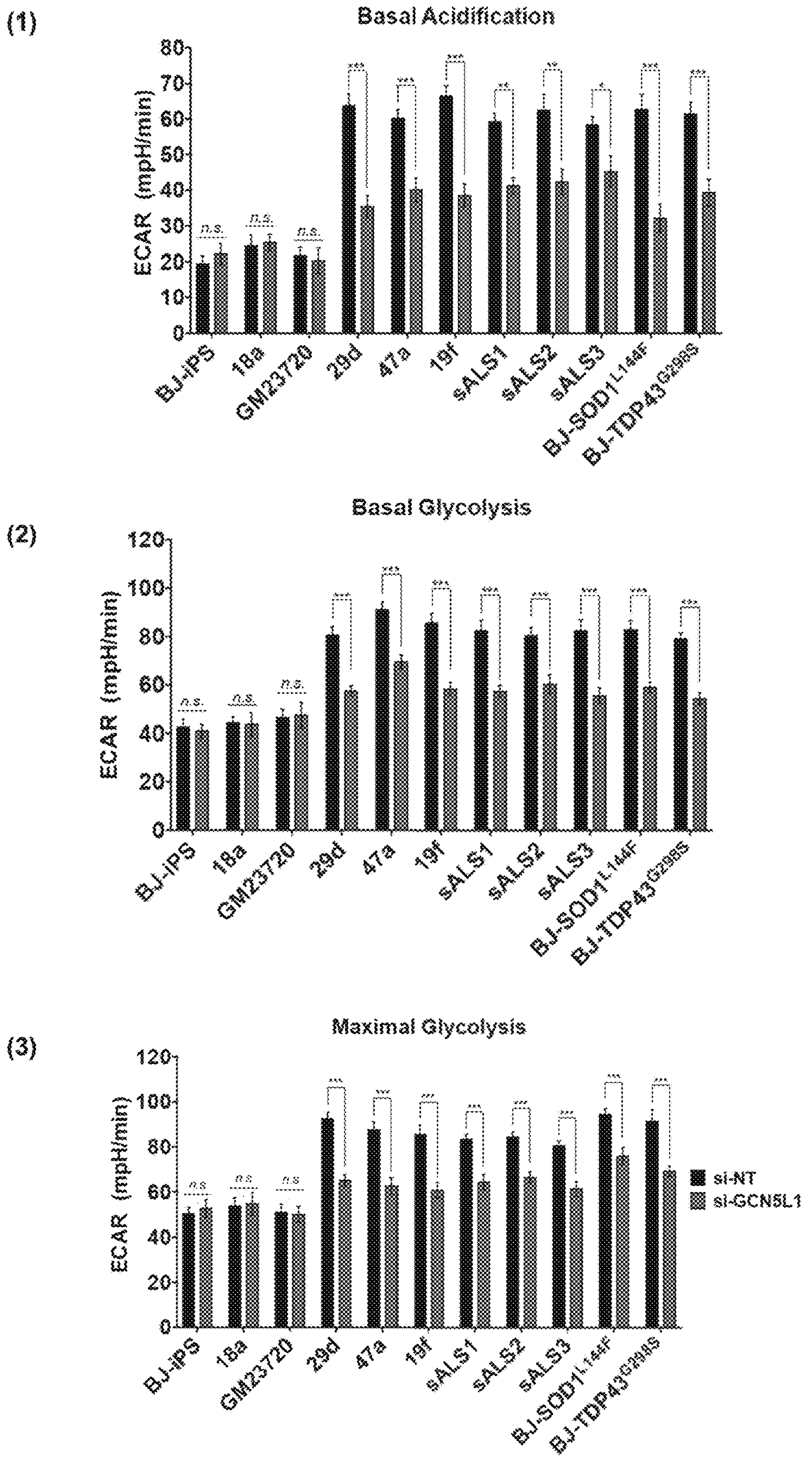
FIG. 9: GCN5L1 knockdown reduced hyper-glycolytic phenotype in ALS MNs. Measurements of basal acidification, basal glycolysis and glycolytic capacity respectively in healthy and ALS MNs treated with non-targeting and GCN5L1 siRNA. In summary, GCN5L1 knockdown reduced hyper-glycolytic phenotype in ALS MNs.
Figure 10:
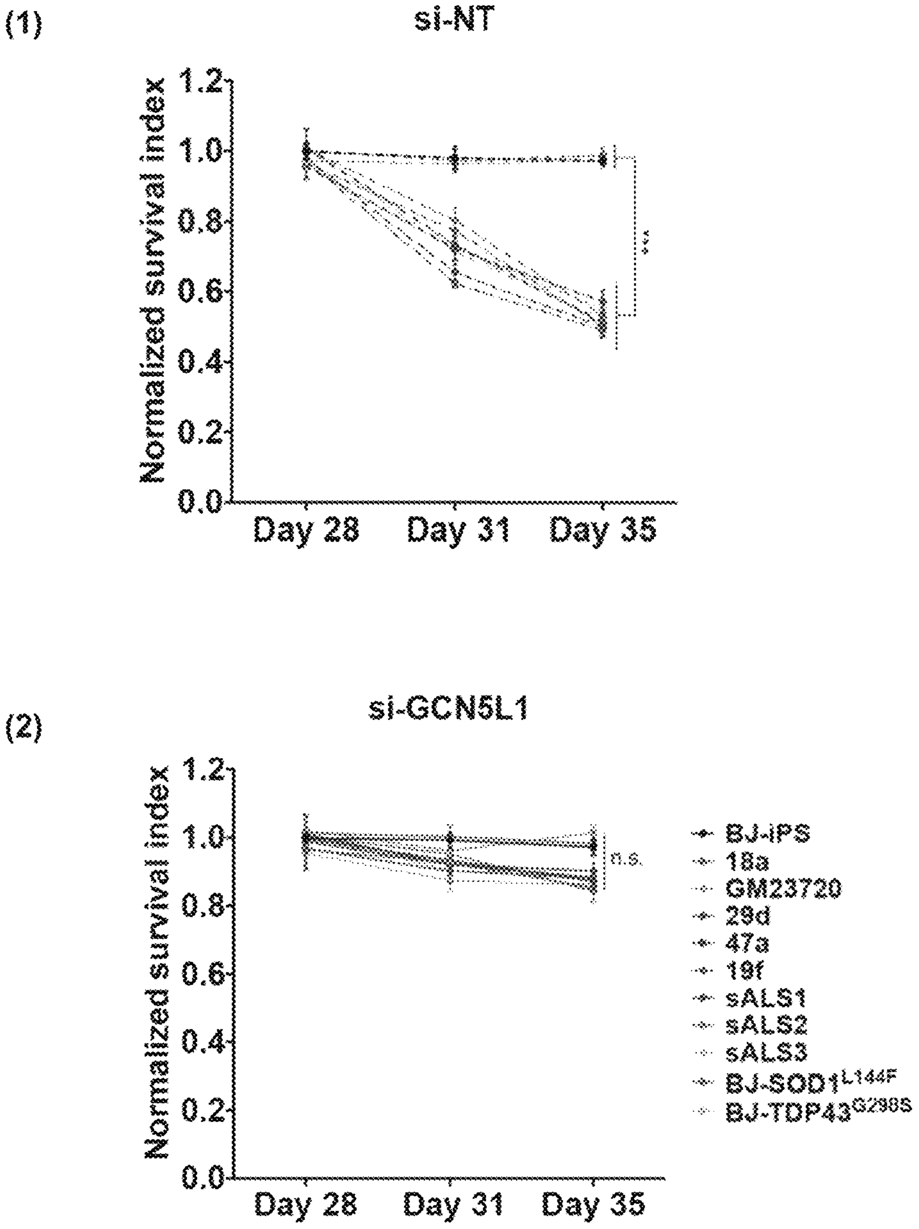
FIG. 10: GCN5L1 knockdown promotes MN survival in ALS MNs. WT and ALS iPSC-derived MNs were treated with either non-targeting or GCN5L1 siRNA from day 28 to day 35. Number of $ISL1^+$ MNs were quantified and normalized to number of $ISL1^+$ MNs in respective cell lines at day 28. GCN5L1 knockdown prevents MN death in ALS MNs.
Figure 11:
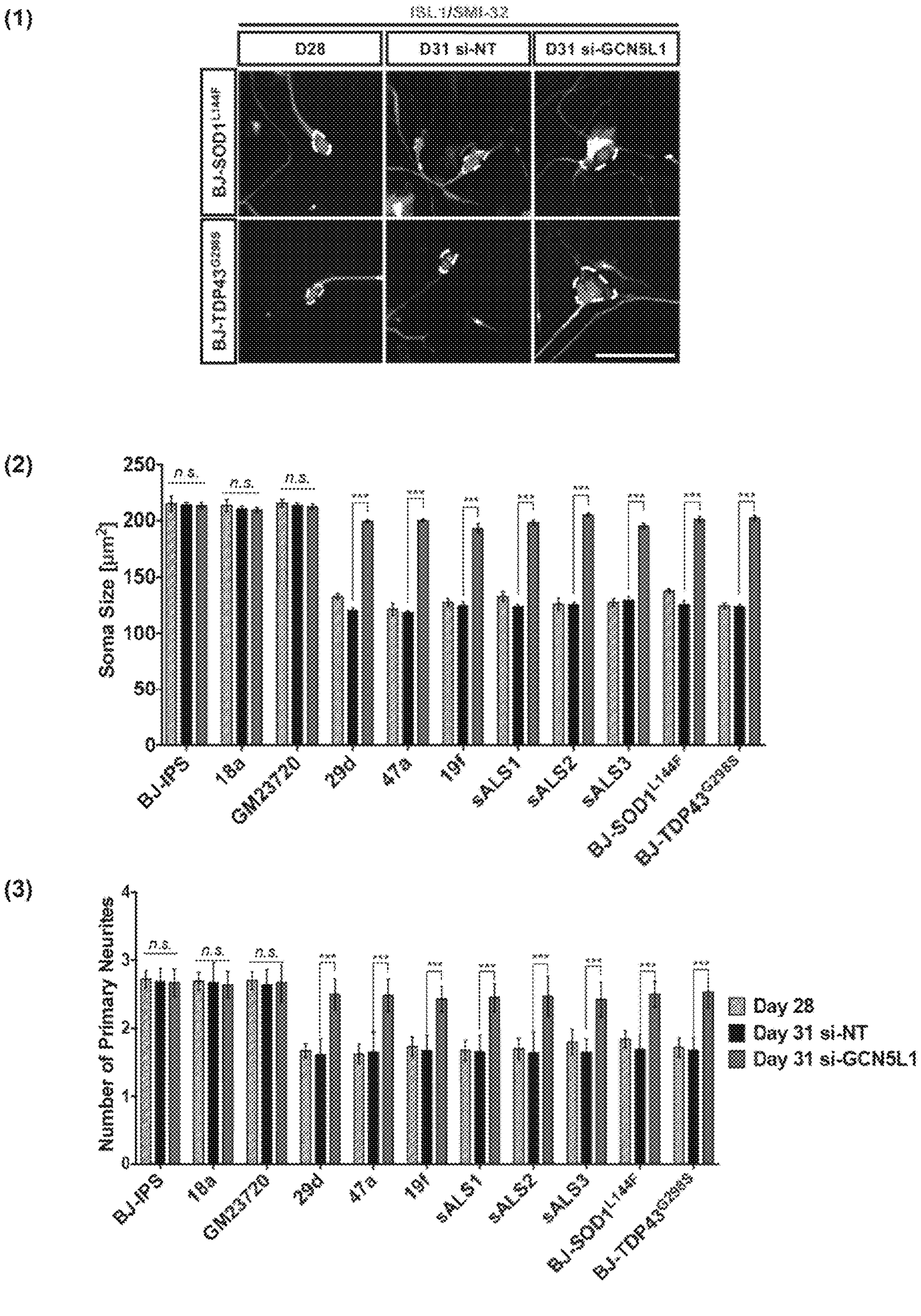
FIG. 11: GCN5L1 knockdown promotes healthier neuronal morphologies. Representative images of $ISL1^+SM132^+$ MNs of BJ-$SOD1^{L144F}$ and BJ-$TDP43^{G298S}$ illustrating GCN5L1 knockdown promotes healthier neuronal morphologies at day 31. Scale bars, 50 μm.
Figure 12:
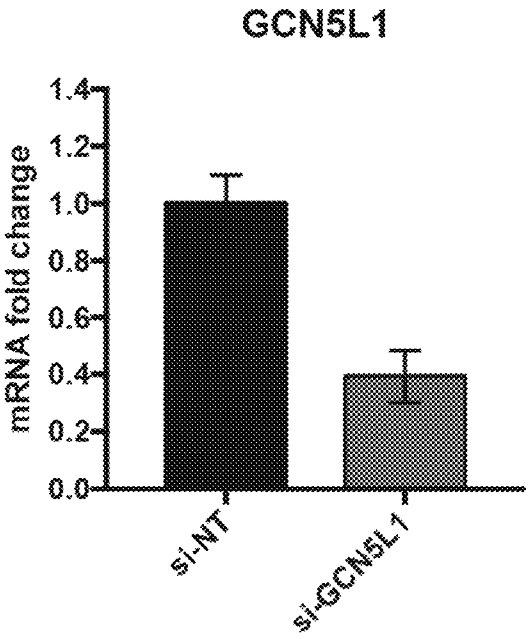
FIG. 12: Confirmation of GCN5L1 knockdown by siRNA. MNs transfected with siRNA against human GCN5L1 showed a 60% reduction of GCN5L1, which was sufficient to promote healthier morphologies and correct the metabolic phenotypes associated with ALS MNs.
Figures 16F, 16G, 16H, 16I, 16J, 16K:
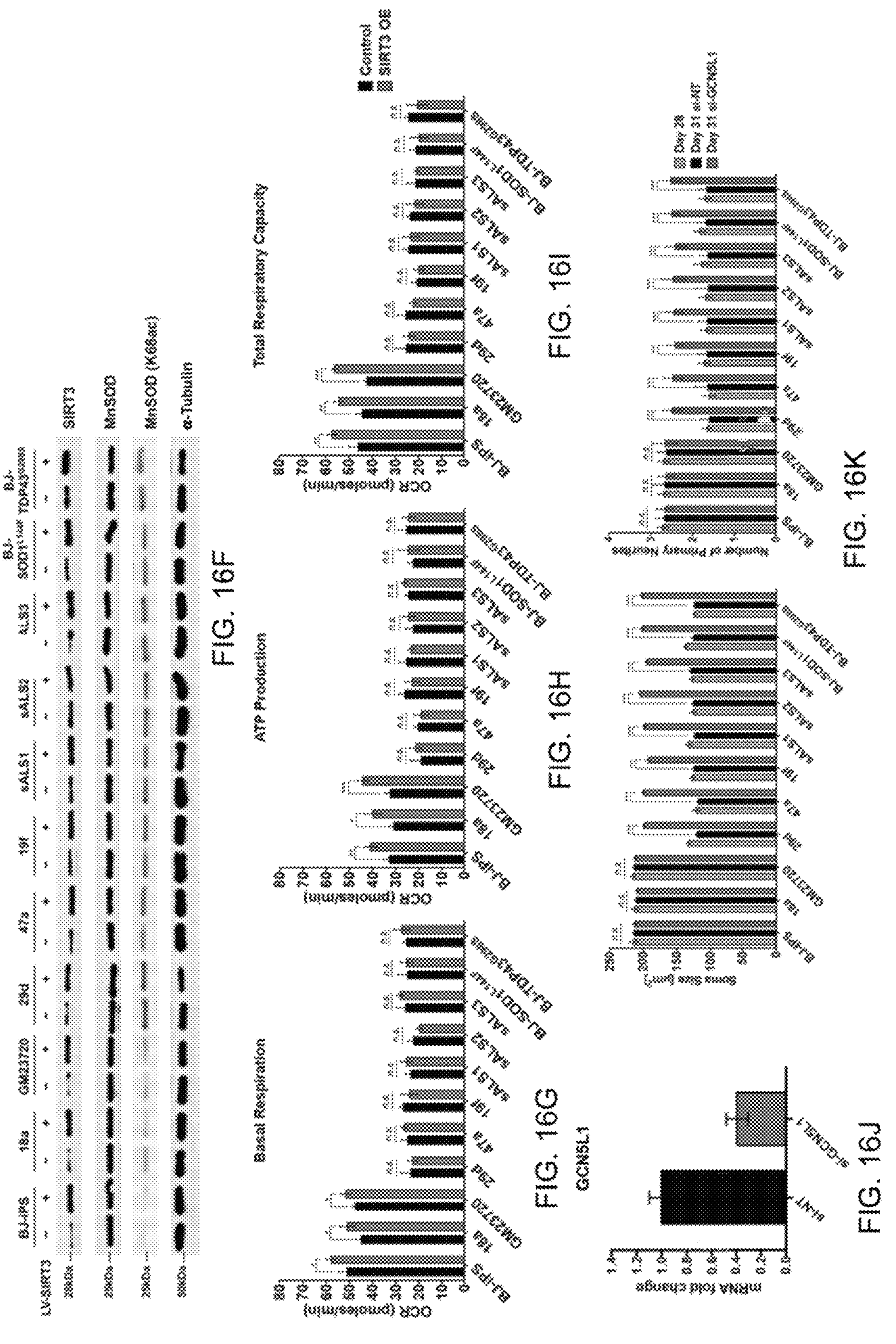

Since GCN5L1 has been implicated to promote acetylation in the mitochondria, it was next investigated if silencing GCN5L1 could improve metabolic defects in ALS MNs and other associated phenotypes. To this end, the iPSC-derived MNs were transfected with siRNAs targeting GCN5L1 and achieved 60% knockdown (FIG. 16J). Metabolic flux analyses using the MitoStress kit revealed significant improvements in basal respiration, ATP production and spare respiratory capacity in GCN5L1 knockdown ALS MNs (FIG. 8). In addition, ECAR measurements demonstrated reduced basal acidification and glycolysis rates, suggesting that GCN5L1 knockdown corrects the hallmark metabolic defect in ALS MNs (FIG. 9). Knockdown of GCN5L1 also promoted survival of ISL1+ MNs and healthier neuronal morphologies (FIG. 10; FIG. 16K).

Figure 6A:
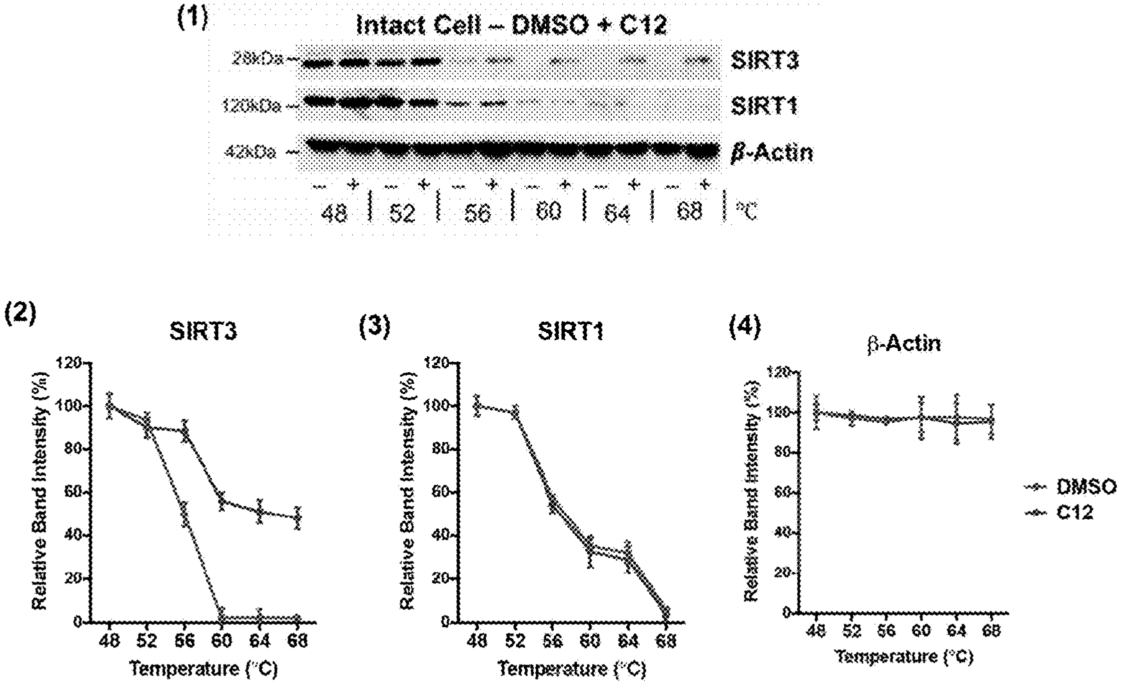
FIG. 6: A small molecule activator of SIRT3, but not Riluzole or Edaravone, improves neuronal morphologies in ALS MNs. (A) Representative Western blot and CETSA melt curves in intact cell for SIRT3 target with C12 (at 20 μM). (B) Western blot analyses at day 31 revealed reduction in mitochondria Ac-K signals in ALS MNs upon C12 treatment. (C) WT and ALS iPSC-derived MNs were treated with either DMSO/$H_2O$ or C12/Riluzole/Edaravone from day 28 to day 35. Number of $ISL1^+$ MNs were quantified and normalized to number of $ISL1^+$ MNs in respective cell lines at day 28. C12, Riluzole and Edaravone treatment prevents MN death in ALS MNs. (D-F) qPCR quantification of ER stress transcripts CHOP and spliced XBP1 (sXBP1) in MN cultures at day 31 treated with controls or C12/Riluzole/Edaravone. Fold changes are normalized to expression levels of respective mRNA in BJ-iPS MNs treated with DMSO or water. Gene expression was normalized to ACTINB and HPRT. ***$p<0.001$, n.s. non-significant; two-tailed t test.
Figure 6B:
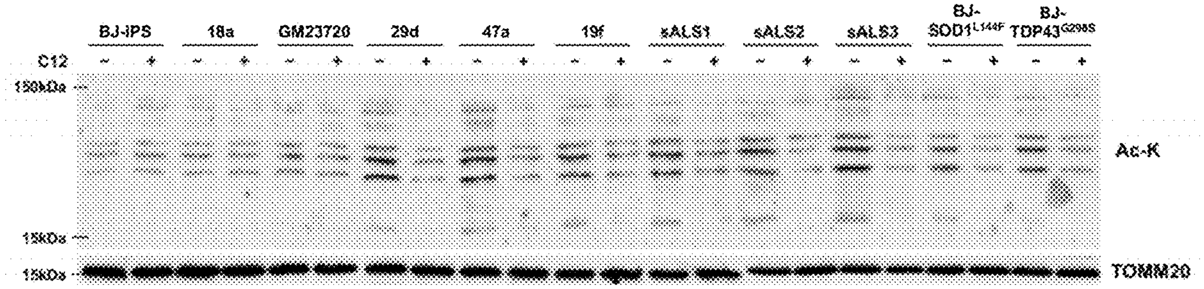
Figures 17A, 17B, 17C, 17D:
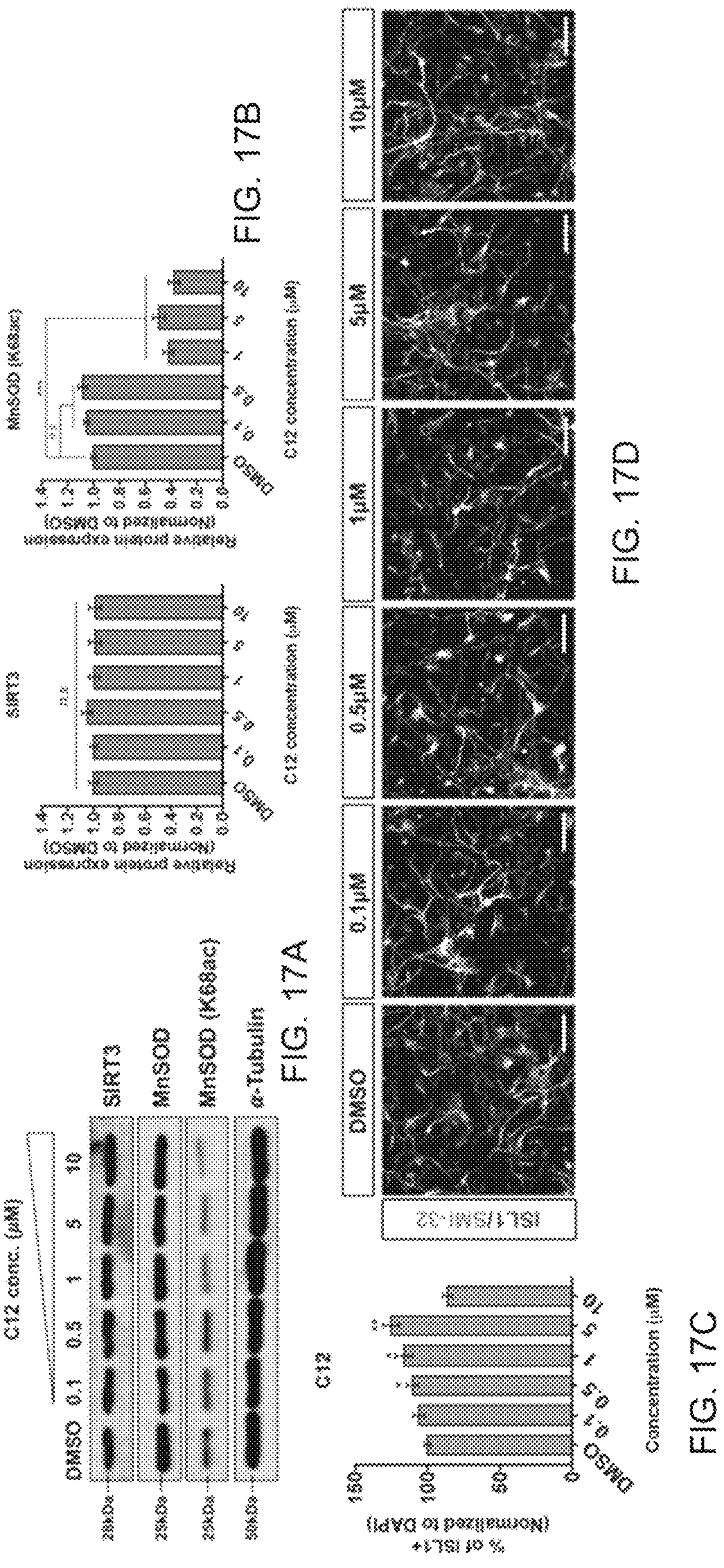
FIG. 17: C12 activates SIRT3 and alleviates ALS diseased phenotypes (Related to FIGS. 6 and 7). (A) Western blot analyses at day 31 revealed a dose dependent reduction in MnSOD (K68ac) levels and no significant changes in SIRT3 protein expression as C12 concentration increased. (B) Densitometric analyses of Western blot bands reveal no significant changes in SIRT3 levels and significant reduction in MnSOD (K68ac) levels in a dose dependent manner in C12 treated MNs. (C) ALS MNs treated with C12 show improvement in motor neuron survival at 5 μM. (D) Representative images of $ISL1^+SM132^+$ ALS MNs illustrates C12 treatment improves motor neuron survival at 5 μM. (E-F) qPCR quantification of ER stress transcripts CHOP and spliced XBP1 (sXBP1) in MN cultures at day 31 treated with DMSO or C12. Fold changes are normalized to expression levels of respective mRNA in BJ-iPS MNs treated with DMSO or water. (G-I) Measurements of glycolysis and glycolytic capacity respectively in healthy and ALS MNs treated with DMSO as a control (light grey) or 5 μM C12 (dark grey). *$p<0.05$, $p<0.01$, *$p<0.001$, n.s. non-significant.

A Small Molecule Activator of SIRT3, but not Riluzole or Edaravone, Improves Mitochondrial Bioenergetics in ALS MNs While there are no known specific GCN5L1 inhibitors described to date, a small number of SIRT3 activators have been identified, including a specific SIRT3 agonist previously identified as 7-hydroxy-3-(4'-methoxyphenyl) coumarin or C12 that changes the conformation of SIRT3 active site with high affinity and promotes deacetylation of downstream targets. To evaluate the specificity of C12 binding to SIRT3, cellular thermal shift assay (CETSA) was used and it was confirmed that C12 promotes thermal stability of SIRT3, but not another abundantly expressed sirtuin, SIRT1 (FIG. 6A). A dose response assay for C12 was next performed by treating MNs derived from one of the ALS lines (BJ-$SOD1^{L144F}$) with increasing doses of C12. Western blot analysis showed reduction of MnSOD K68ac signals in a dose-dependent manner while SIRT3 and total MnSOD protein levels remains unchanged (FIGS. 17A, 17B). It was also noted that treatment with 10 μM C12 was cytotoxic (FIGS. 17C, 17D), and it was decided to perform subsequent experiments using 5 μM C12. By treating the panel of ALS MNs with 5 μM C12, it was further demonstrated that mitochondrial acetyl-lysine signals were significantly reduced in all the ALS cultures (FIG. 6B), confirming that C12 promotes mitochondrial deacetylation.

Figure 6C:
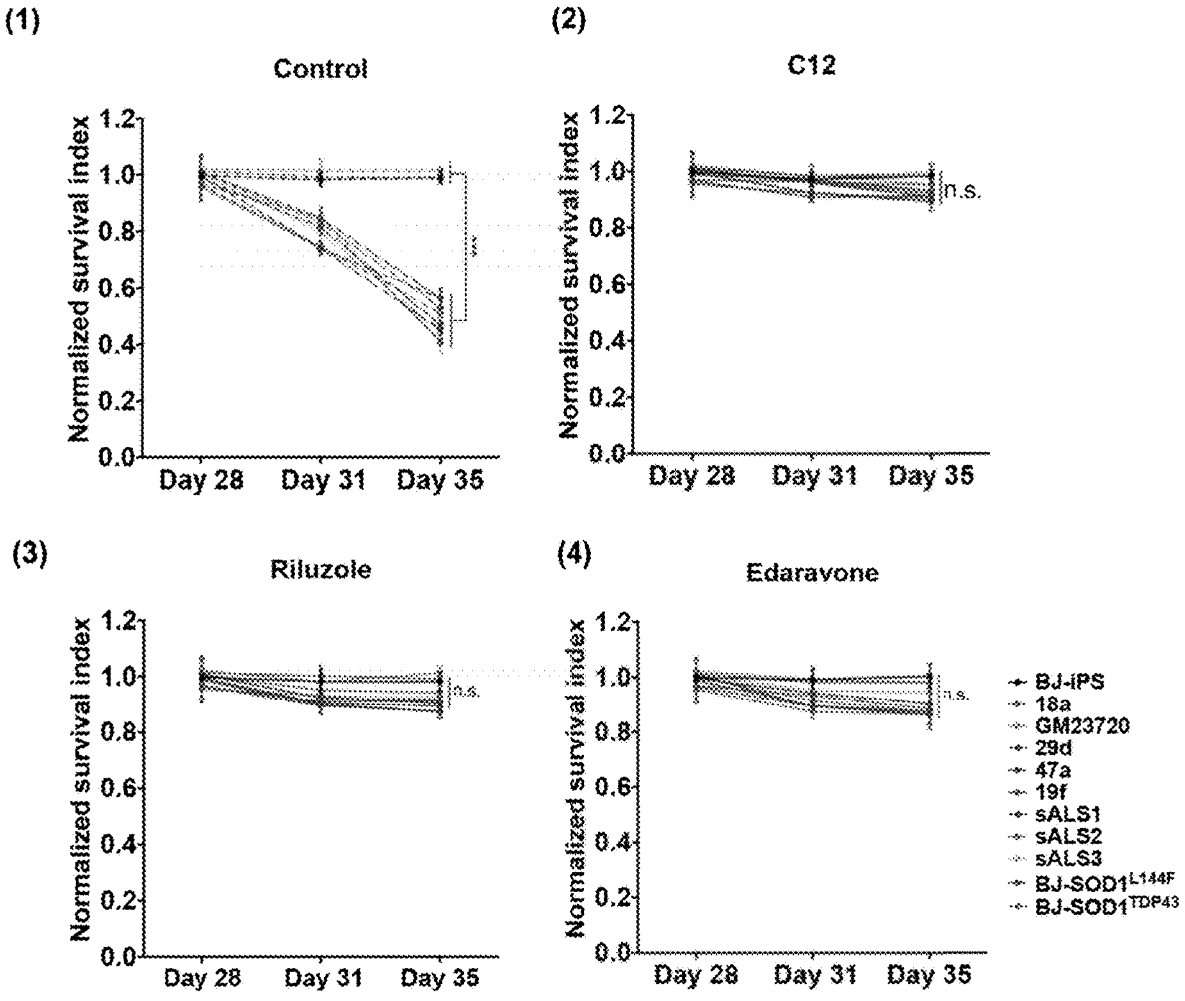
Figure 6D:
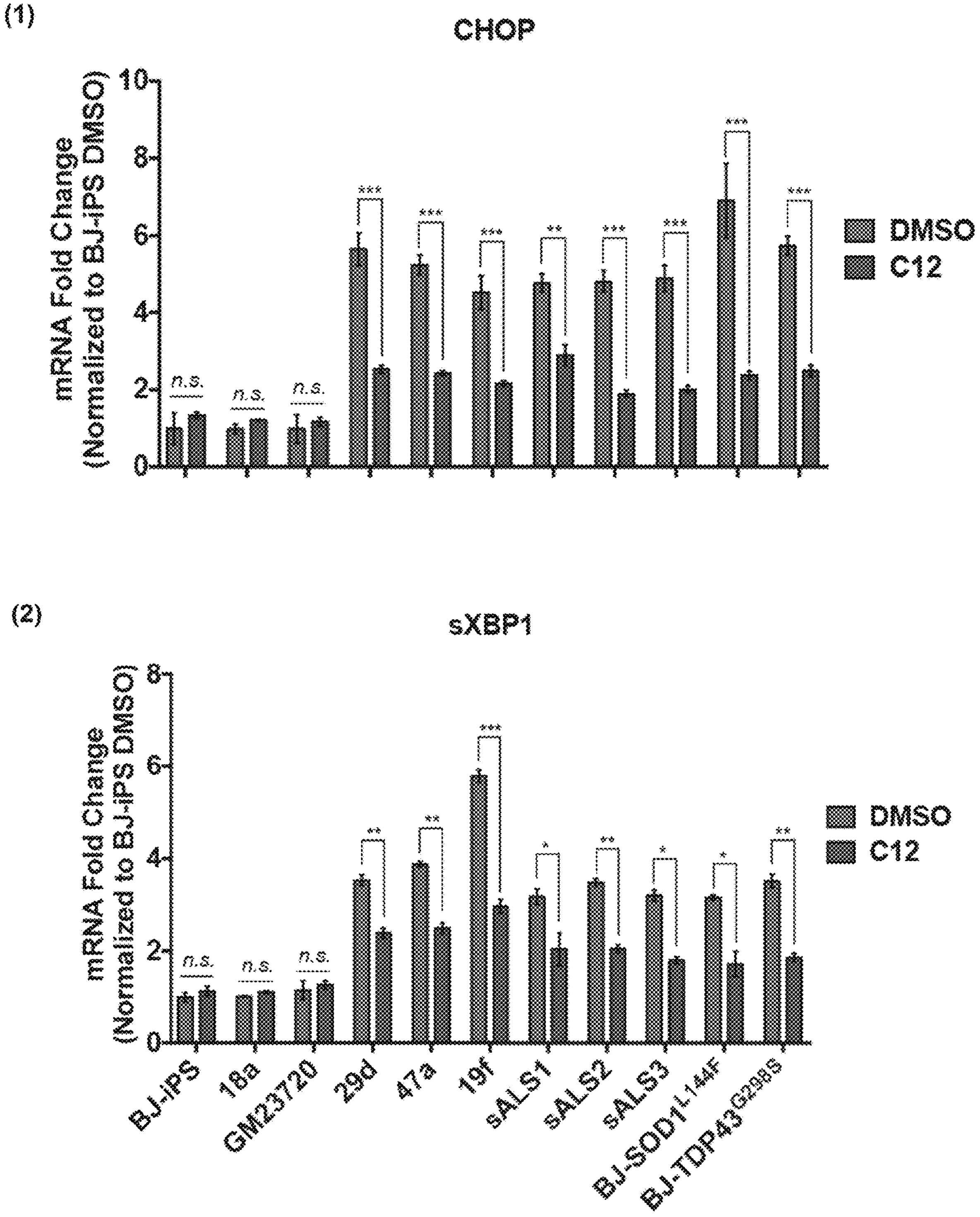
Figure 6E:
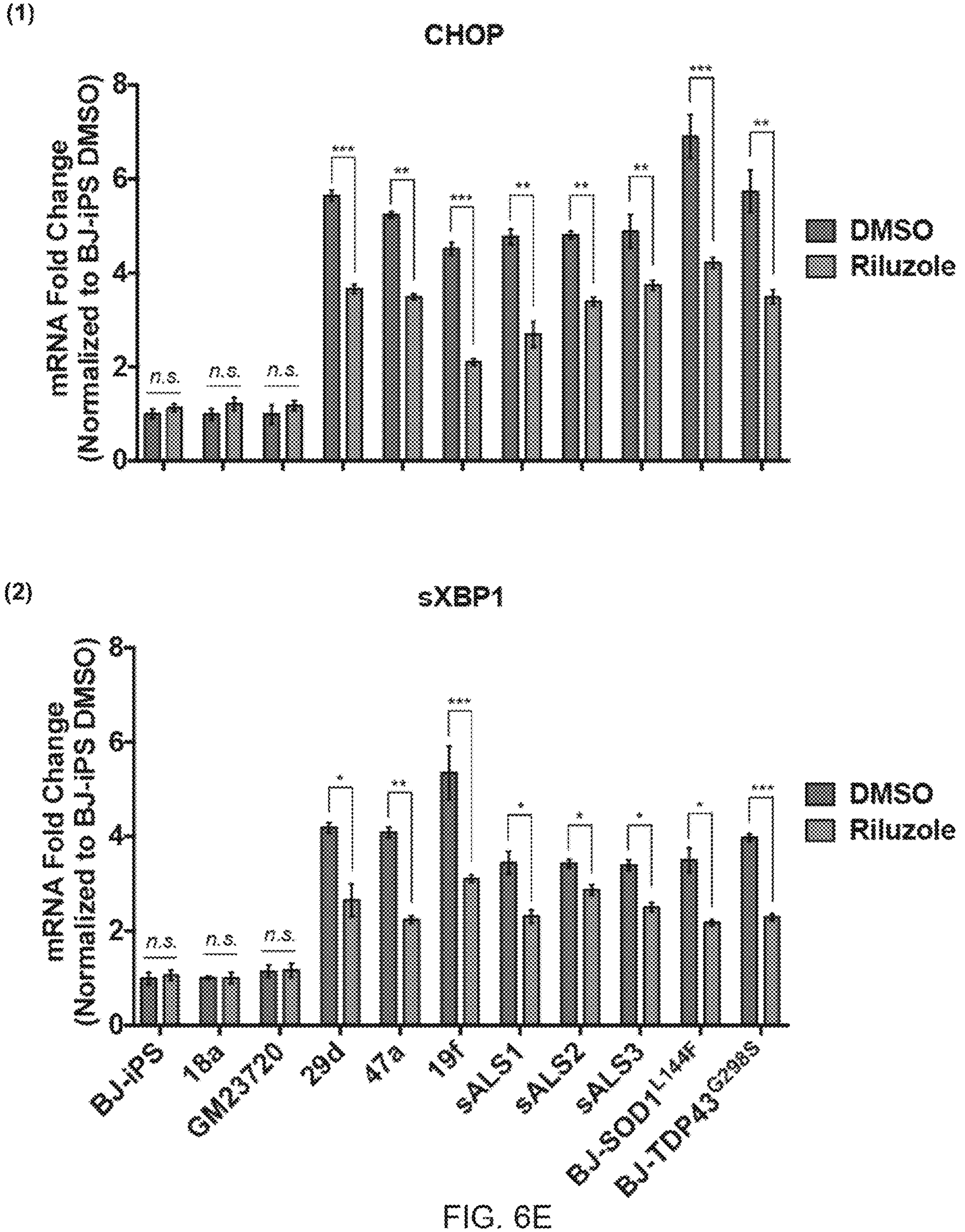
Figure 6F:
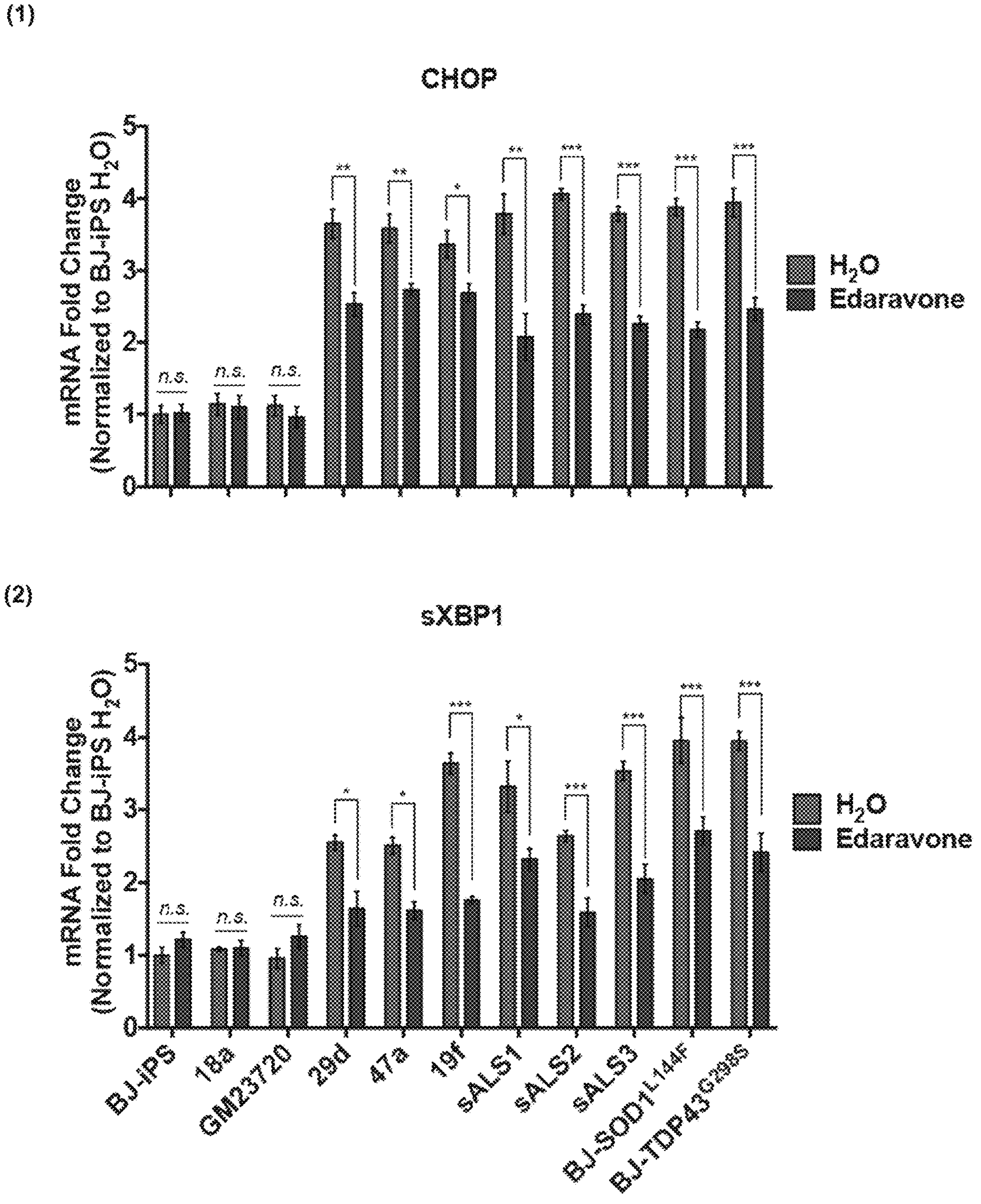

The effects of C12 were next compared vis-à-vis the FDA-approved treatments for ALS, namely Riluzole and Edaravone. Riluzole functions by blocking sodium channel and Edaravone works as a ROS scavenger. However, it is currently not known whether Riluzole and Edaravone would regulate mitochondrial respiration. To this end, the iPSC-derived MNs were treated with Riluzole, Edaravone or DMSO and water controls from day 28 to 31. The repertoire of iPSC-derived MNs was treated with C12, Riluzole, Edaravone or DMSO and water controls from day 28 to 31. First, it was found that all three compounds promoted ALS MN survival (FIG. 6C). Likewise, all three compounds significantly reduced expressions of ER stress transcripts CHOP and sXBP1 in all the ALS MNs (FIGS. 6D-F).

Figure 7A:
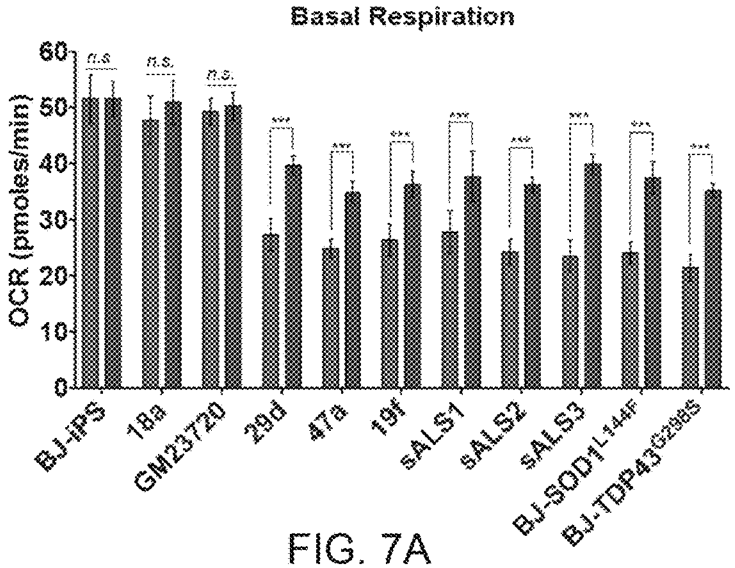
FIG. 7: A small molecule activator of SIRT3, but not Riluzole or Edaravone, reverses metabolic defects in ALS MNs. (A-C) Measurements of basal respiration, ATP production and spare respiration respectively in healthy and ALS MNs treated with DMSO and C12. Of note, C12 treatment rescued ATP production back to healthy levels. (D-F) Measurements of basal respiration, ATP production and spare respiration respectively in healthy and ALS MNs treated with DMSO and Riluzole. Of note, Riluzole treatment are not able to revert ALS MNs mitochondrial bioenergetics defects. (G-I) Measurements of basal respiration, ATP production and spare respiration respectively in healthy and ALS MNs treated with water and Edaravone. Of note, Edaravone treatment are not able to revert ALS MNs mitochondrial bioenergetics defects. (J) Representative images of $ISL1^+SM132^+$ MNs of BJ-iPS, BJ-$SOD1^{L144F}$ and BJ-$TDP43^{G298S}$ illustrates only C12 treatment promotes healthier neuronal morphologies, showing cell body sizes (outlined in white dotted lines) from MNs at day 28, and at day 31. Scale bars, 50 μm. ***$p<0.001$, n.s. non-significant; two-tailed t test.
Figure 7B:
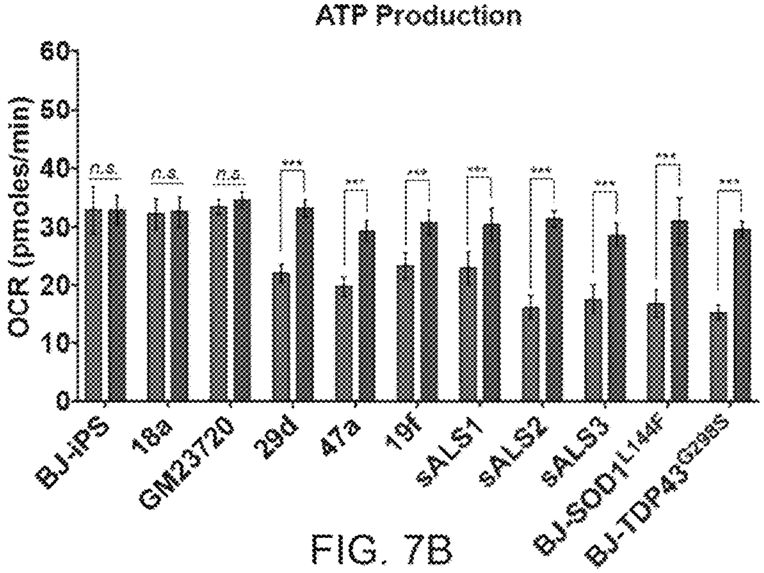
Figure 7C:
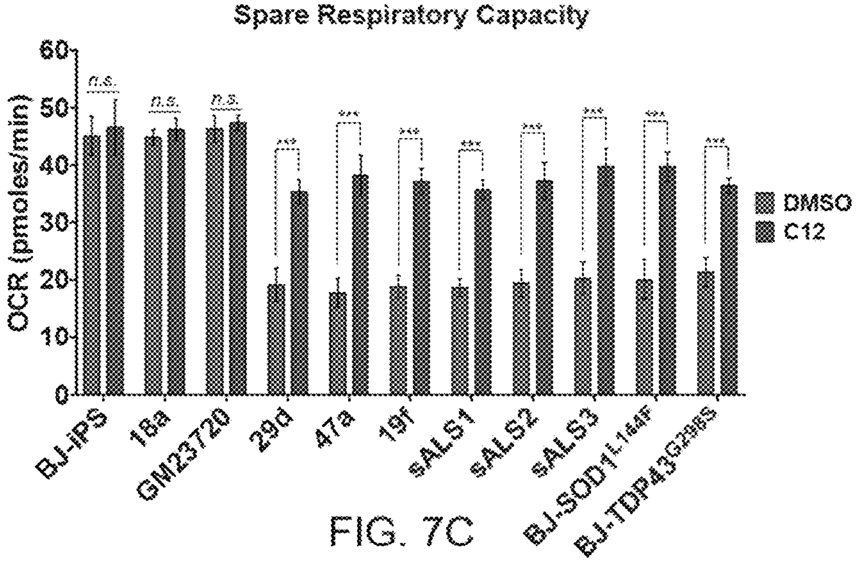
Figure 7D:
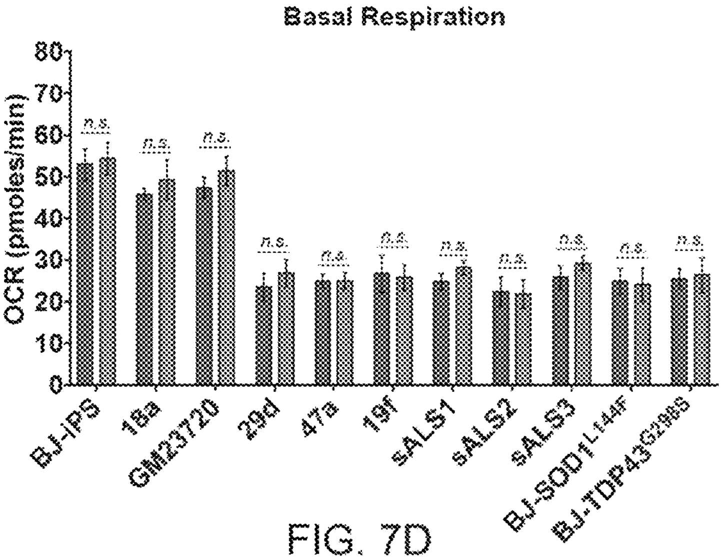
Figure 7E:
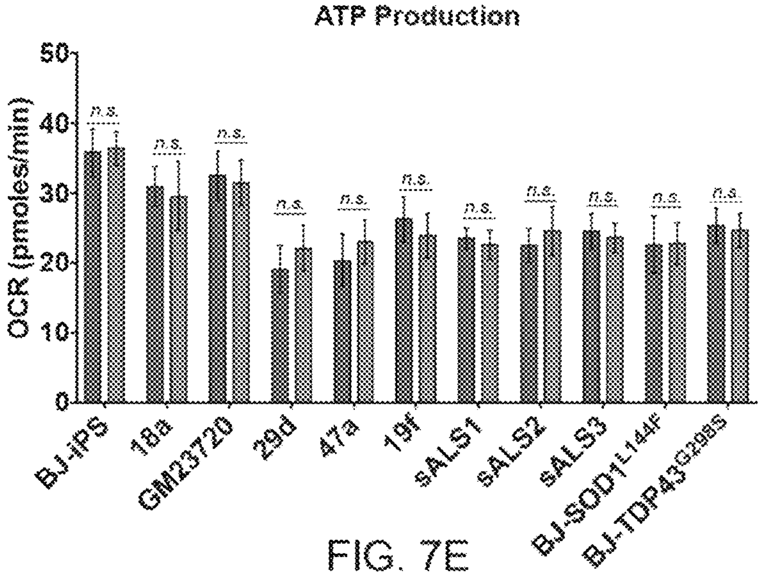
Figure 7F:
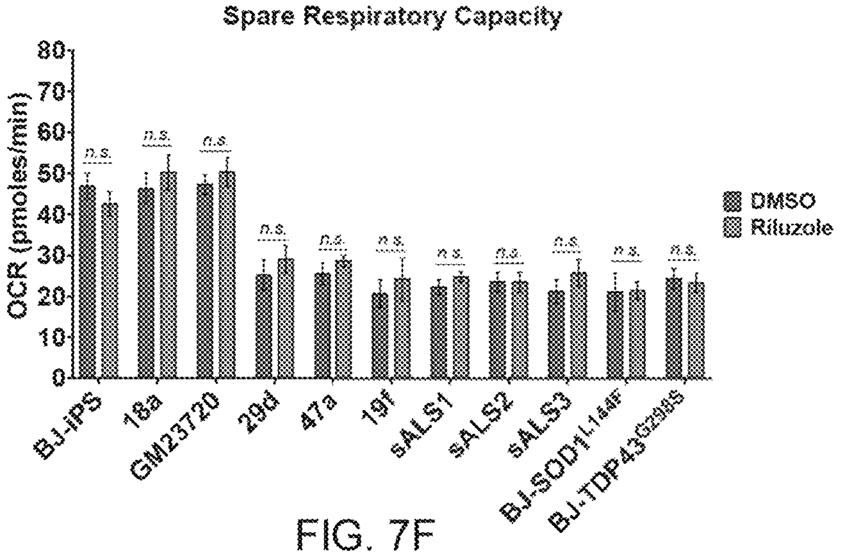
Figure 7G:
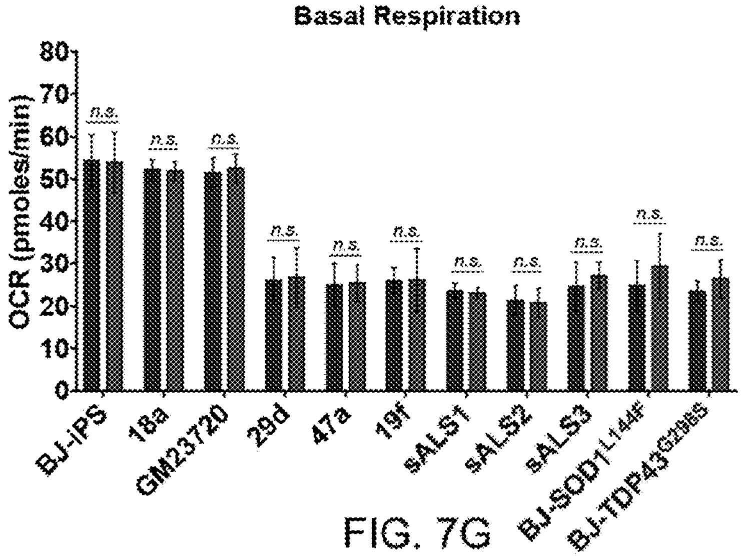
Figure 7H:
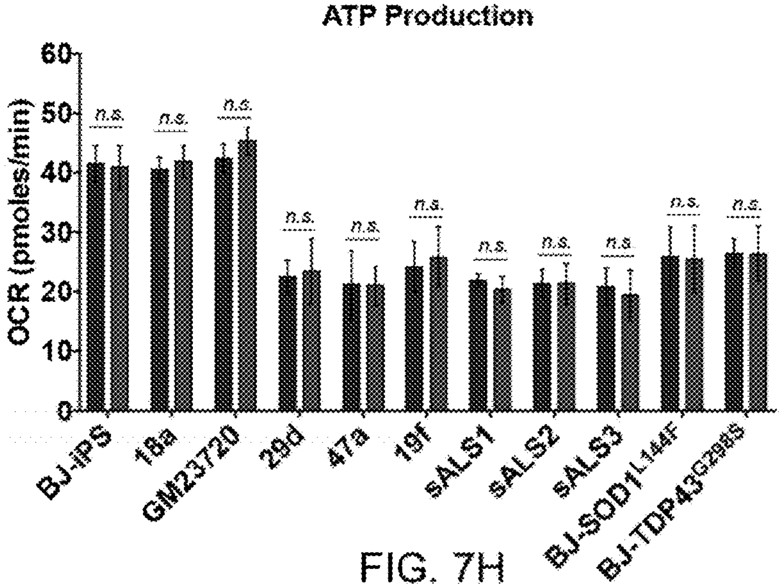
Figure 7I:
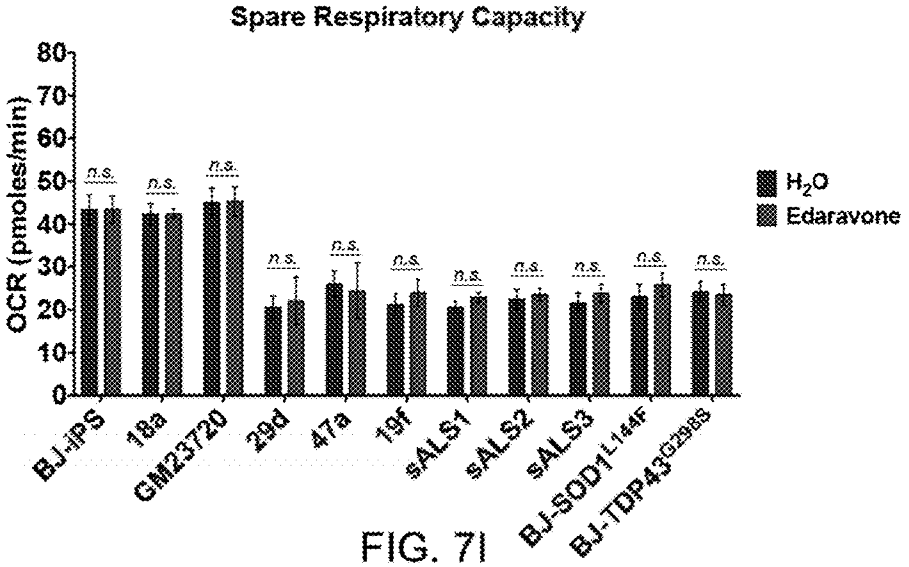
Figure 7J:
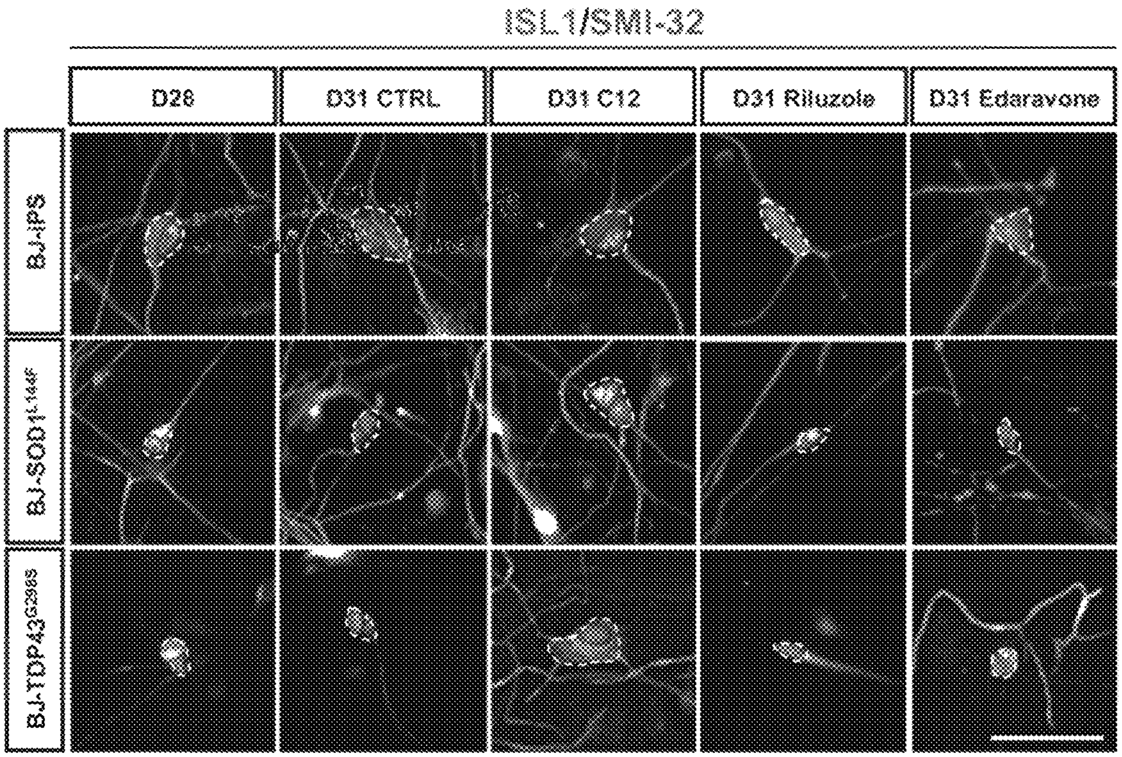
Figures 17E, 17F, 17G, 17H, 17I:
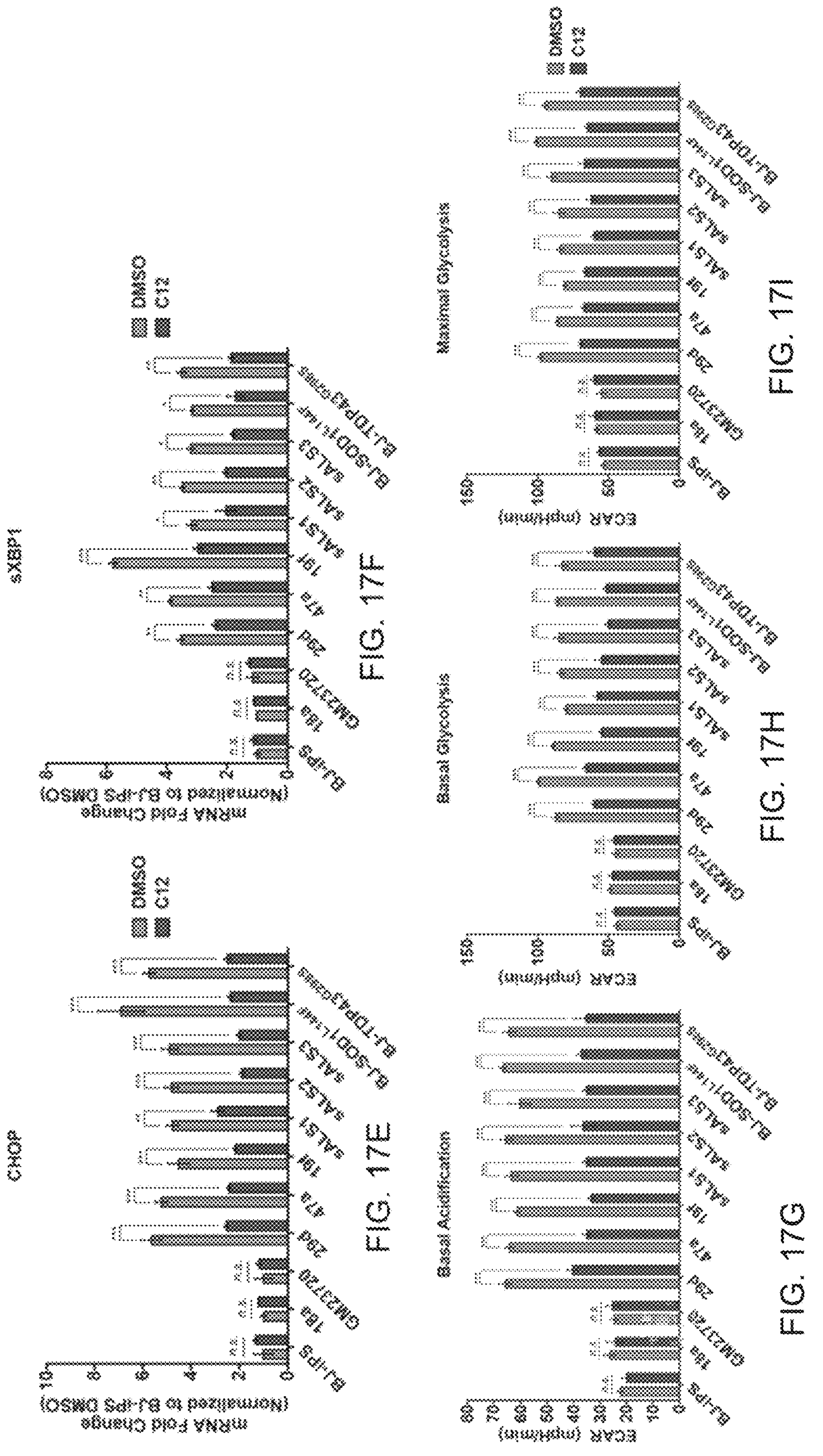
Figure 18A:
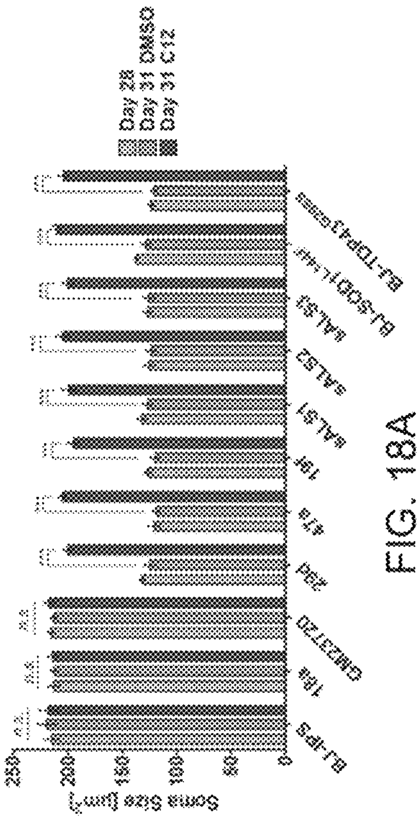
FIG. 18: C12 treatment, but not Riluzole or Edaravone treatment, improves neuronal morphologies in ALS MNs (Related to FIG. 7). (A-B) Measurement of soma size and primary neurites show overall improvement in neuronal morphology in C12 treated ALS MNs. (C) Representative images of $ISL1^+SM132^+$ MNs derived from healthy and ALS iPSCs, showing cell body sizes (outlined in white dotted lines) from MNs at day 28, and at day 31 after treatment of C12. Scale bars, 50 μm. (D) Representative images of $ISL1^+SM132^+$ MNs derived from healthy and ALS iPSCs, showing cell body sizes (outlined in white dotted lines) from MNs at day 28, and at day 31 after treatment with Riluzole or Edaravone. Scale bars, 50 μm. (E-H) Treatment of ALS MNs with Riluzole or Edaravone did not improve neuronal morphologies. Measurement of soma sizes and number of primary neurites of treated neurons show no significant change compared to their respective controls. ***p<0.001, n.s. non-significant.
Figure 18B:
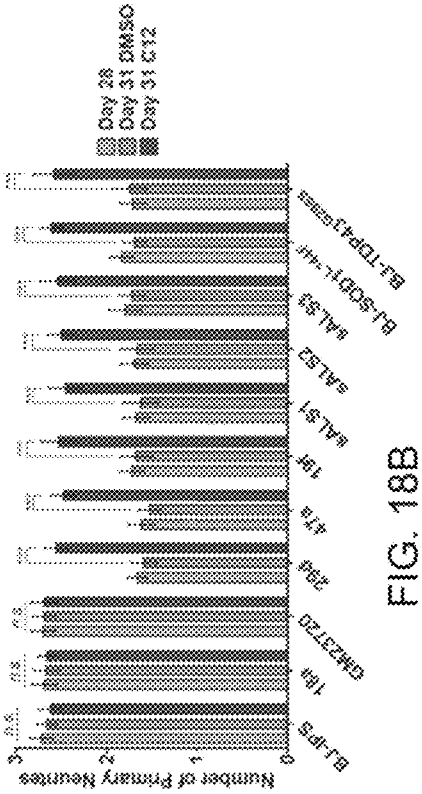
Figure 18C:
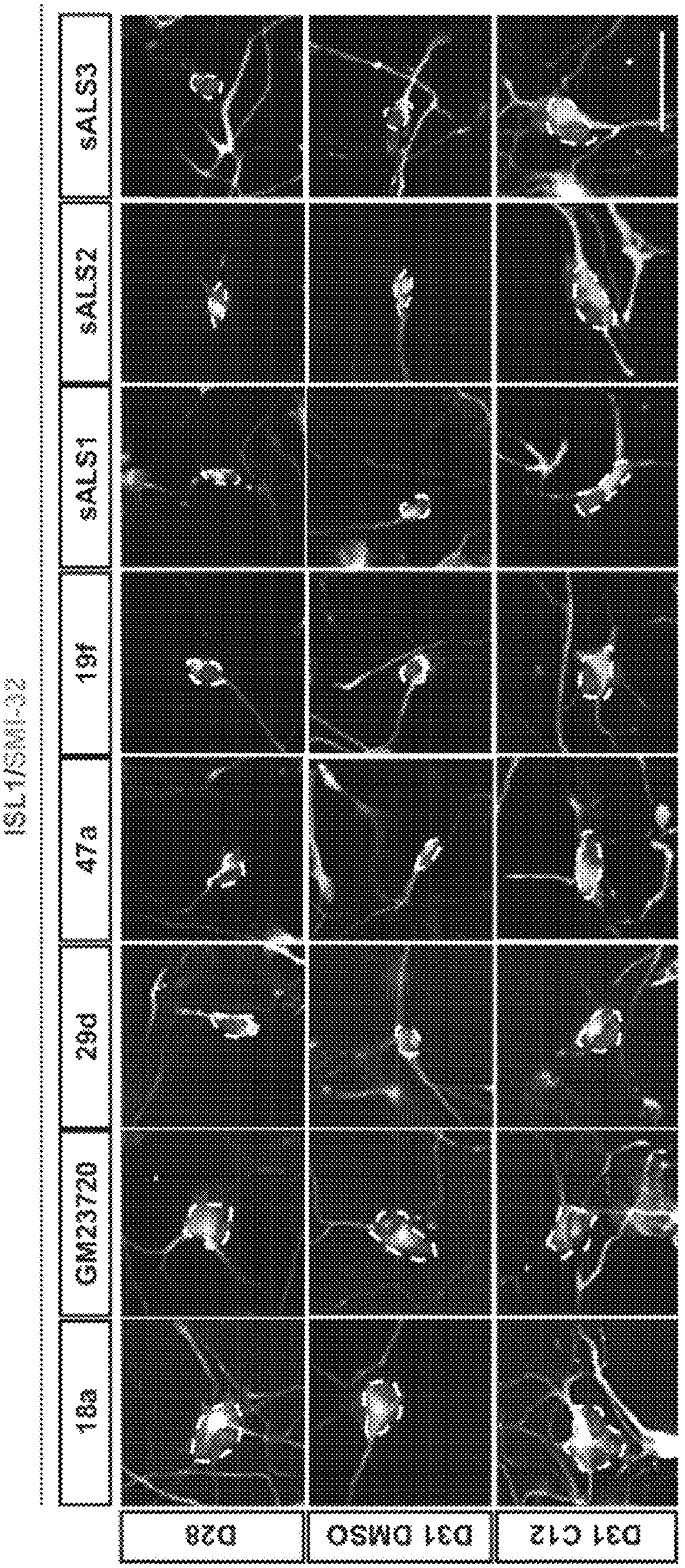
Figure 18D:
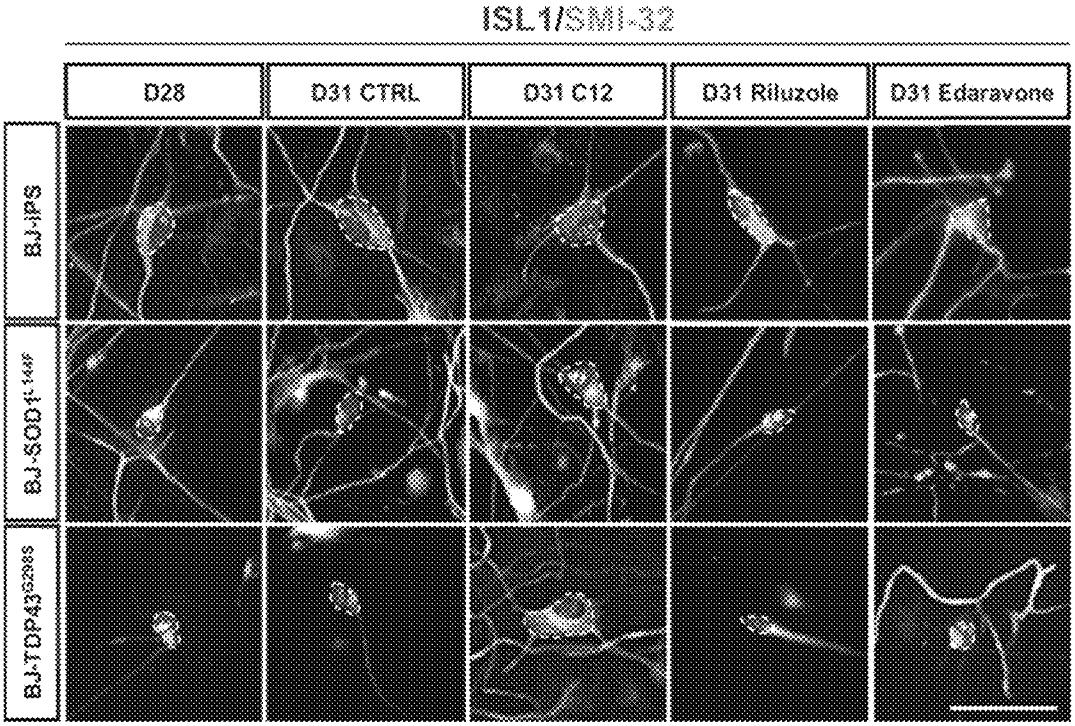
Figure 18E:
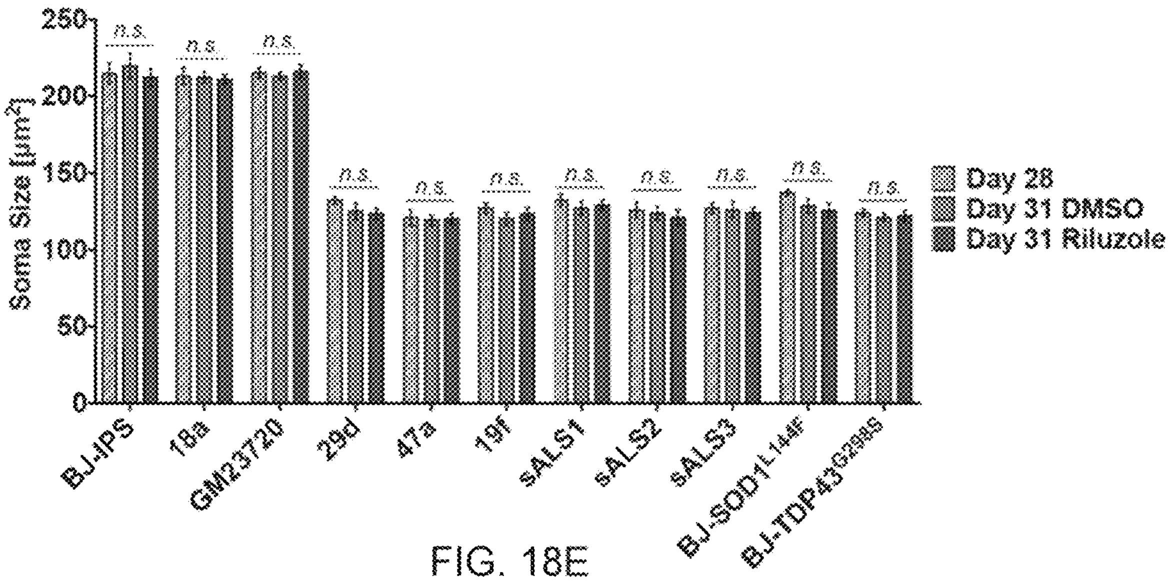
Figure 18F:
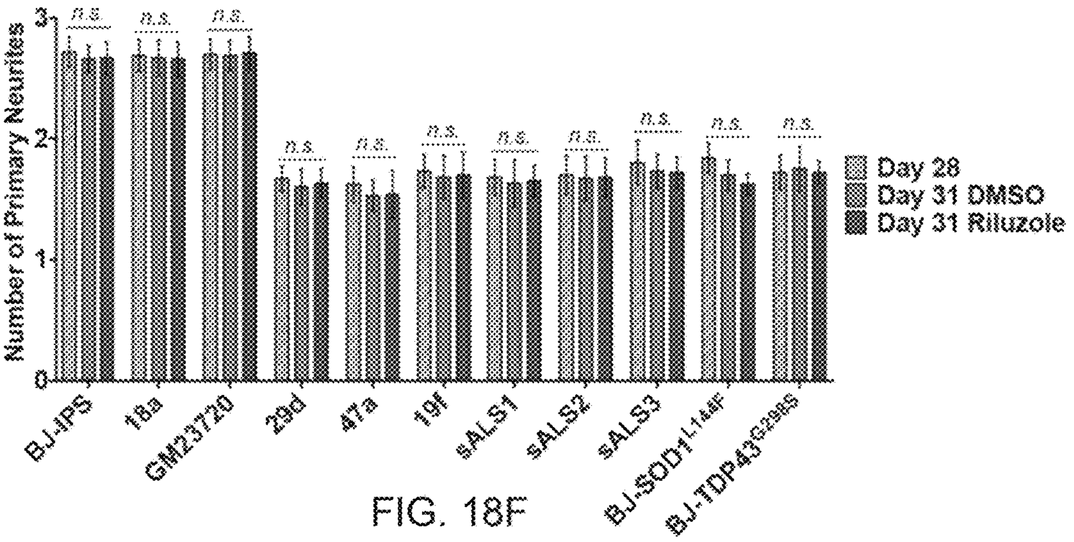
Figure 18G:
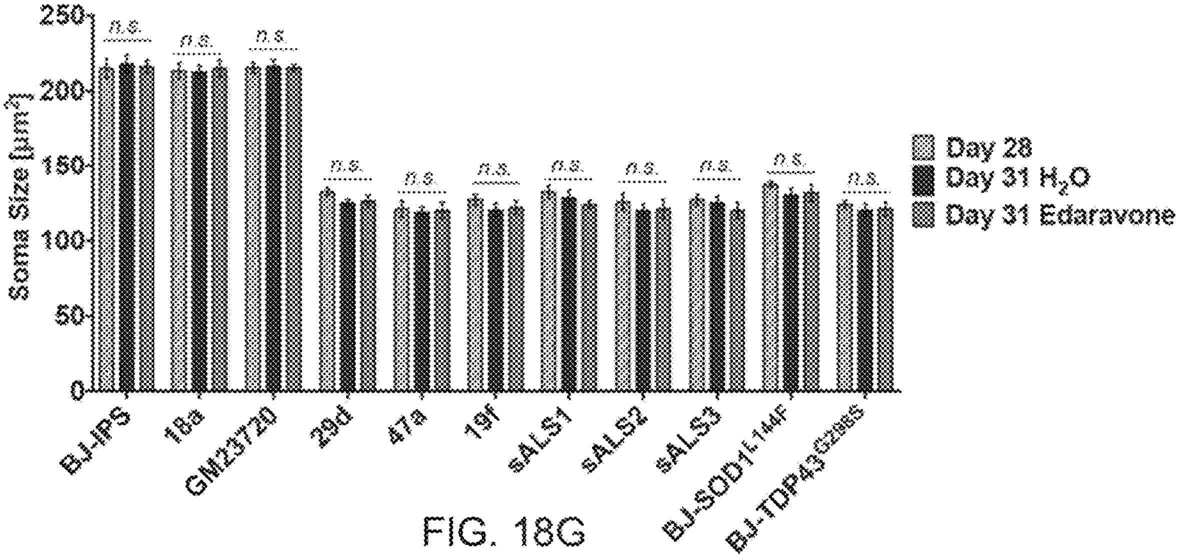
Figure 18H:
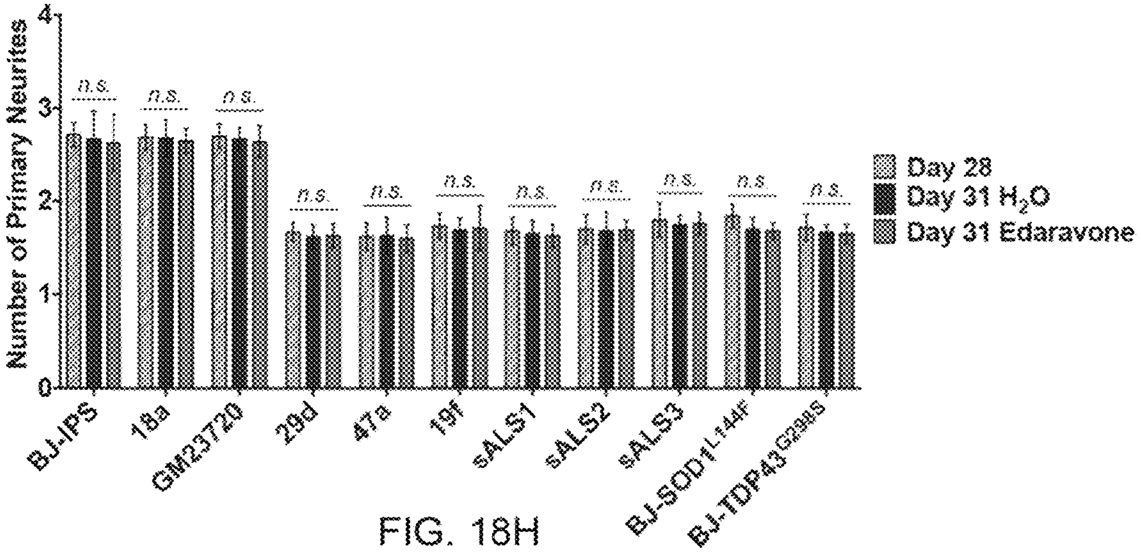

Metabolic flux analyses at day 31 revealed that C12 promoted mitochondrial respiration (FIGS. 7A-C), reduced glycolysis (FIGS. 17E-G), and increased mitochondrial Complex I activity (FIG. 17H) in ALS MNs. Metabolic flux analyses revealed that Riluzole and Edaravone treatment did not show any significant changes in the metabolic profiles of ALS MNs (FIG. 7D-I), indicating that treatment with either Riluzole or Edaravone did not improve mitochondrial bioenergetics. C12 treatment also improved neuronal morphologies, resulting in enlarged soma sizes and increased number of primary neurites similar to healthy MNs (FIG. 7J, FIGS. 18A-C). However, treatment with either Riluzole or Edaravone did not improve neuronal morphologies (FIG. 7J, FIG. 18D-H). Collectively, these data suggest that SIRT3 activation is effective in promoting motor neuron survival and maintaining mitochondrial bioenergetics in ALS MNs.

Figure 19A:
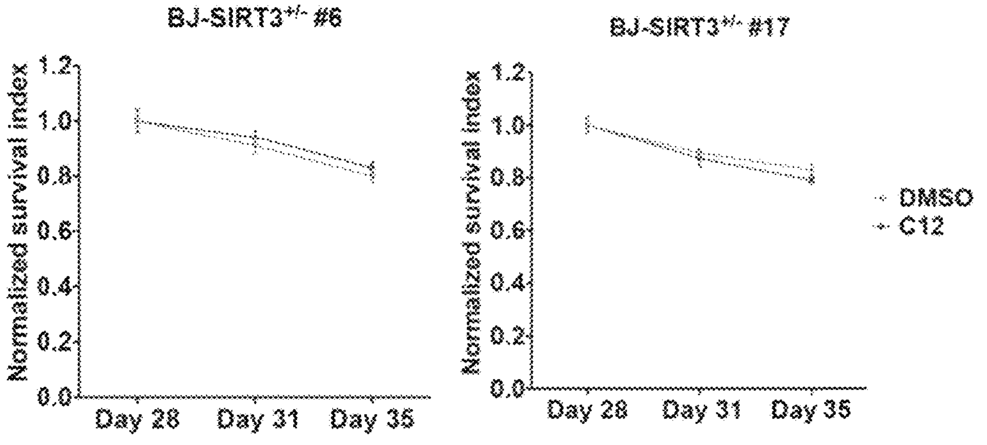
FIG. 19: C12 targets/activates SIRT3 and does not show effects in SIRT3-deficient clones. (A-C) Treatment of $SIRT3^{+/-}$ clones #6 and #17 with C12 did not improve MN survival, MN morphologies or mitochondrial respiration.
Figure 19B:
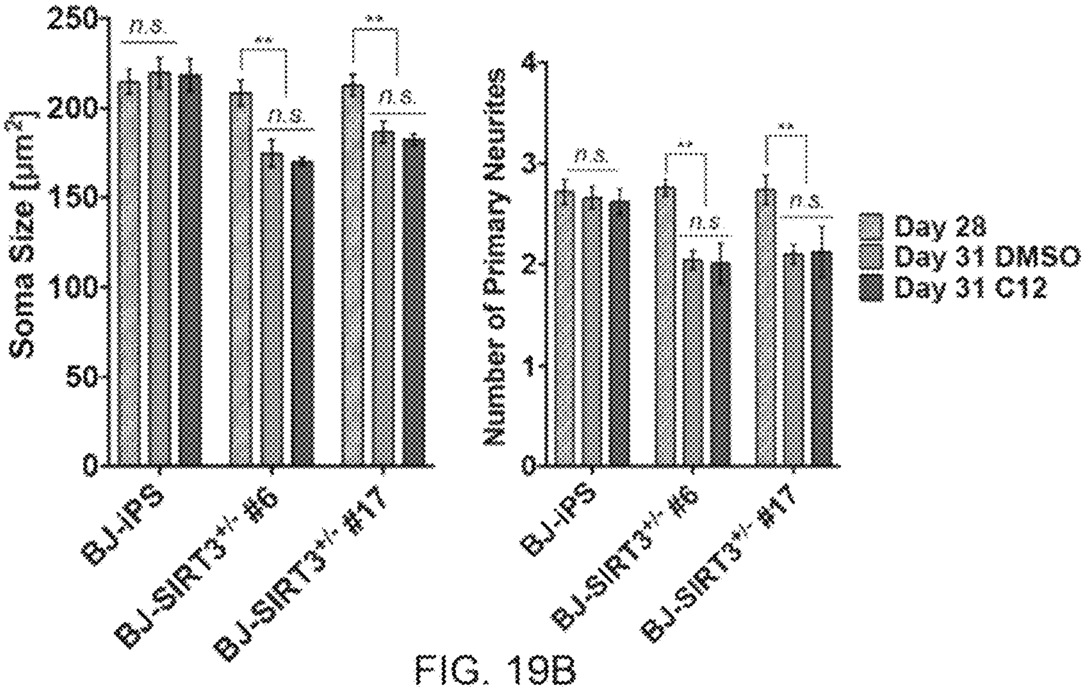
Figure 19C:
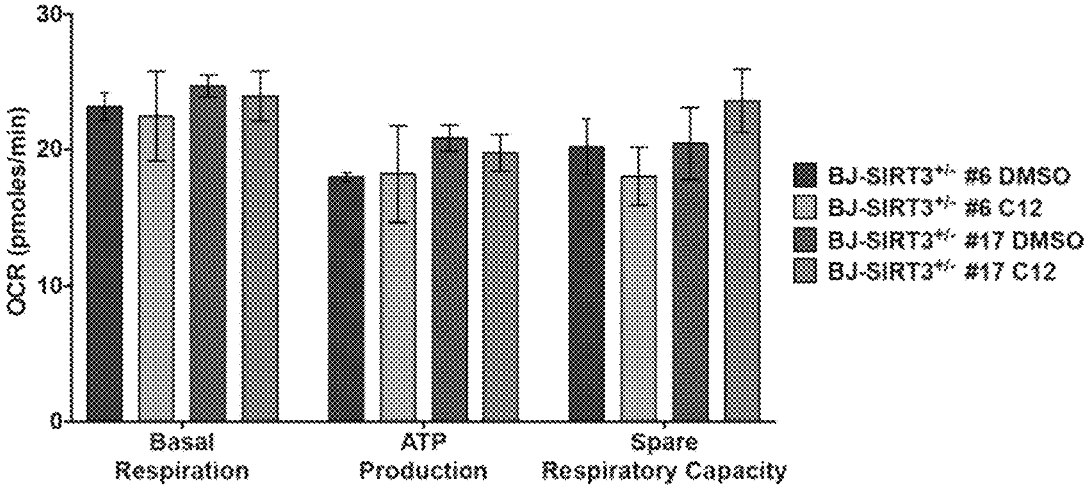

Notably, treatment of BJ-$SIRT3^{+/-}$ #6 and #17 with C12 did not promote survival or improve neuronal morphology (FIGS. 19A, 19B). C12 treatment on both SIRT3-deficient clones also did not improve mitochondrial respiration (FIG. 19C), providing additional evidence that C12 works through promoting SIRT3 activity rather than via non-specific off-target effects.

Figure 20A:
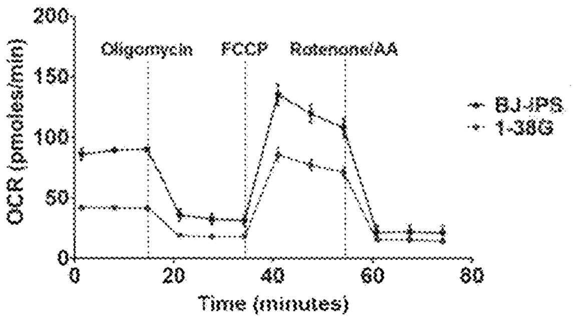
FIG. 20: SIRT3 activation reversed mitochondrial respiration defects specific to ALS MNs. (Related to FIG. 7). (A) OCR measurements using the MitoStress assay was performed and calculated for healthy (BJ-iPS) and SMA type I (1-38G) MNs at day 28. (B) Basal respiration, ATP production and spare respiration were calculated and revealed decreased mitochondrial bioenergetics in SMA type I. (C) Measurements of OCR using the MitoStress assay in BJ-iPS and SMA type I MNs, treated with DMSO (light grey) or 5 μM C12 (dark grey). (D) Measurements of basal respiration, ATP production and spare respiration respectively in healthy (BJ-iPS) and SMA type I (1-38G) MNs treated with DMSO as a control (light grey) or 5 μM C12 (dark grey) show no improvement in mitochondrial bioenergetics in SMA MNs, suggesting that SIRT3 activation is specific in rescuing ALS MNs. ***p<0.001, n.s. non-significant.
Figure 20B:
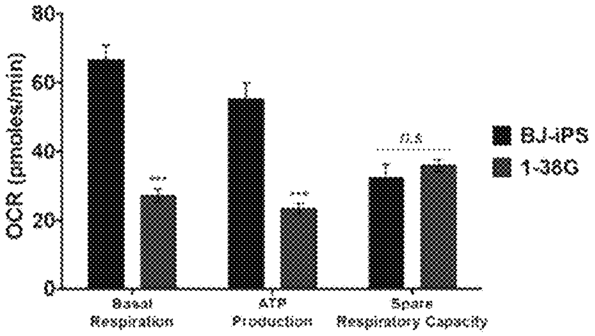
Figure 20C:
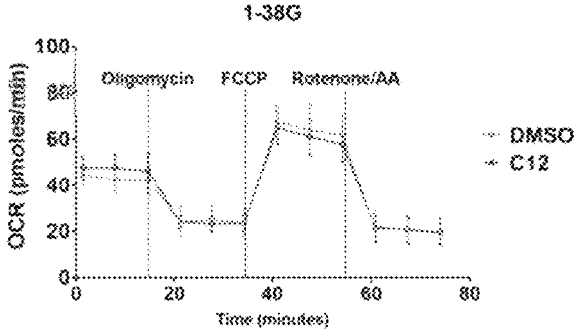
Figure 20D:
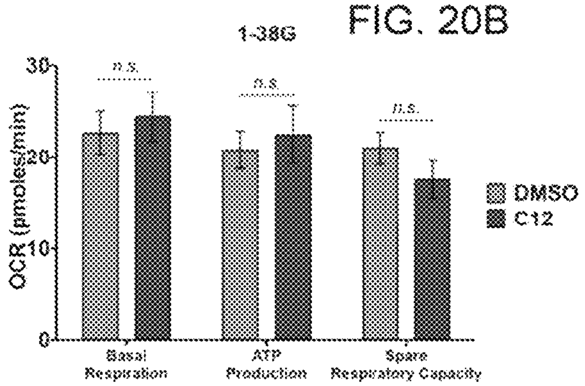

Finally, it was wondered if SIRT3 activation has a general neuroprotective effect or is specific to the rescue of ALS MNs. In order to investigate this, it was decided to analyze effects of C12 treatment on MNs derived from patients with Spinal Muscular Atrophy (SMA). SMA is an autosomal recessive motor neuron disorder, caused by mutations in both copies of SMN1 gene, resulting in drastically reduced full length, functional SMN protein. Differentiating iPSCs from a severe Type I SMA patient (1-38G) towards MNs, and performing the MitoStress assay at day 28, significant declines in basal respiration and ATP production in the SMA MNs compared to healthy BJ MNs were measured (FIGS. 20A, 20B). Subsequent treatment of these SMA MNs with C12 did not improve the metabolic defect, (FIGS. 20C, 20D) suggesting that SIRT3 activation is specific in the rescue of ALS MNs.

DISCUSSION

ALS is a heterogeneous motor neuron disease, yet all patients have similar clinical manifestations, suggesting the possibility of a converging pathogenic pathway independent of the various genetic mutations known to cause ALS. In this disclosure, a metabolic hallmark of both sporadic and familial ALS MNs that is characterized by hypo-oxidation and hyper-glycolysis was identified. Increased production and release of lactate, the end product of the glycolytic pathway, would explain the central nervous system acidosis seen in $SOD1^{G93A}$ mice. Reductions in cellular respiration were also observed in the post-mortem spinal cord of sporadic ALS patients. It is highly possible that the hyper-glycolytic metabolism was a compensatory mechanism to overcome the lack of ATP generated through oxidative phosphorylation in ALS MNs, because restoration of ATP production through NAM supplementation and SIRT3 activation also corrected the hyper-glycolytic metabolic profile.

Although the functional relevance of other mitochondrial sirtuins in ALS pathogenesis remains to be elucidated, this current disclosure demonstrates the importance of SIRT3 in regulating mitochondrial function in MNs. SIRT3 deficiency have been seen in many neurodegenerative diseases as well as metabolic disorders. Loss of SIRT3 results in mitochondrial fragmentation in spinal motor neurons of $SOD1^{G93A}$ mice leading to neuronal death. One of the key findings was that reduced mitochondrial respiration and hyper-acetylated mitochondrial proteins are molecular hallmarks of ALS MNs. MNs derived from familial and sporadic patient iPSCs, as well as isogenic iPSC lines with $SOD1^{L144F}$ and $TDP43^{G298S}$ mutations demonstrate a consistent increase in acetylated mitochondrial proteins, including MnSOD K68ac, a well characterized target of SIRT3. Post-mortem analyses of ALS spinal cords further corroborated this finding. This molecular defect was accompanied by a resultant defect in mitochondrial respiration, which was reversed by SIRT3 activation.

In addition to using patient-derived iPSCs, isogenic cell lines were made to confirm the findings that loss of SIRT3 activity was responsible for the mitochondrial metabolic defects, and the constellation of ALS-like phenotypes. It was noted that $SIRT3^{-/-}$ iPSCs in this study, while mice with complete Sirt3-knockout develop normally and are not embryonic lethal, although neuronal survival and function appear to be affected. It is believed these may be due to species-specific differences. Nevertheless, the results confirmed that partial loss of SIRT3 was sufficient to cause ALS phenotypes in iPSC-derived MNs.

GCN5L1 have been shown to promote acetylation in the mitochondria, and shares a subset of mitochondrial targets with SIRT3. Although the mechanism of GCN5L1 in initiating acetylation remains largely unknown, it has been shown that knocking down GCN5L1 resulted in decreased mitochondrial protein acetylation and improvement in mitochondrial OCR. Similarly, knockdown of GCN5L1 in ALS MNs improves mitochondrial respiration and reduces glycolytic capacity, demonstrating the role of GCN5L1 in regulating mitochondrial respiration. Improved MN survival and neuronal morphologies were also observed in ALS MNs treated with siRNAs targeting GCN5L1, suggesting that GCN5L1 is a potential target to reverse metabolic defects in ALS MNs and slow down disease pathology.

Apart from reversing the metabolic defects in ALS MNs, SIRT3 activation and/or GCN5L1 inhibition also rescued other in vitro ALS phenotypes. This suggests that early ALS neuronal deficits are reversible and treatable and that the SIRT3-GCN5L1 axis is a crucial upstream pathway regulating MN function and integrity. In support of the data, it has also been shown that $Sirt3^{-/-}$ mouse cortical neurons are particularly vulnerable to excitatory, oxidative and metabolic stress. The data supports that $NAD^+$ levels in ALS patients are reduced compared to the healthy population, and confirms that supplementation of NAM, a precursor of $NAD^+$, reverses ALS phenotypes. Additionally, intracellular nicotinamide phosphoribosyltransferase (iNAMPT) knockout in adult mice project neurons leads to a MN degeneration phenotype mimicking ALS. iNAMPT functions as the rate-limiting enzyme of the mammalian $NAD^+$ biosynthesis salvage pathway. It has been noted that depletion of iNAMPT in motor neurons led to mitochondrial protein hyperacetylation that is most likely due to reduction in SIRT3 activity brought about by low $NAD^+$ levels. Taken together, these findings demonstrate that $NAD^+$ is important in regulating mitochondrial function and metabolic processes, possibly through SIRT3 activation.

Of interest to the field, it was also found that Riluzole and Edaravone, the two FDA-approved drugs for ALS treatment, were ineffective in reversing the mitochondrial metabolic defect that is signature of ALS MNs. This may explain the minimal benefits of the drugs—Riluzole was found to be efficacious amongst bulbar-onset ALS patients and not in subjects with limb-onset ALS, which constitutes most of the ALS patients. On average, Riluzole extends lifespan by 3 months while Edaravone showed efficacy only in a small subset of ALS patients.

In conclusion, the disclosure using patient-derived and isogenic iPSCs reveals that reduced mitochondrial respiration and elevated glycolysis are metabolic hallmarks of ALS MNs. It is also established that activation of mitochondrial SIRT3 is a target for reversing disease phenotypes for both sporadic and familial ALS. Finally, the data confirms that NAM supplementation, as well as a small molecule SIRT3 agonist reverse several in vitro ALS phenotypes and have therapeutic potential for development into an effective treatment.

Methods

Key resources table

| REAGENT or RESOURCE | SOURCE | IDENTIFIER |
|---|---|---|
| Antibodies | | |
| Rabbit anti-SirT3 (D22A3) | Cell Signaling | 5490; RRID: AB_10828246 |
| Mouse anti-alpha tubulin (B-7) | Santa Cruz | sc-5286; RRID:AB_628411 |
| Mouse Anti-TOMM20 | Abcam | ab56783; RRID: AB_945896 |
| Rabbit anti-Islet 1 [EP4182] | Abcam | ab109517; RRID: AB_10866454 |
| Mouse anti-SMI-32 | BioLegend | 801701; RRID: AB_2564642 |
| Rabbit anti-Acetylated-Lysine | Cell Signaling | 9814; RRID: AB_10544700 |

-continued

| Key resources table | | |
|---|---|---|
| REAGENT or RESOURCE | SOURCE | IDENTIFIER |
| Rabbit anti-SOD2/MnSOD | Abcam | ab13533; RRID: AB_300434 |
| Rabbit anti-SOD2/MnSOD (acetyl K68) | Abcam | ab137037; RRID: AB_2784527 |
| Rabbit anti-SATB2 [EPNCIR130A] | Abcam | ab92446; RRID: AB_10563678 |
| Goat anti-BRN2 (C-20) | Santa Cruz | sc-6029; RRID: AB_2167385 |
| Rabbit anti-FOXG1 | Abcam | ab18259; RRID: AB_732415 |
| Rabbit anti-SOX1 | Abcam | ab87775; RRID: AB_2616563 |
| Mouse anti-NESTIN [10C2] | Abcam | ab22035; RRID: AB_446732 |
| Rabbit anti-Doublecortin | Abcam | ab18723; RRID: AB_732011 |
| Mouse anti-TUJ1 | BioLegend | 801201; RRID: AB_2313773 |
| Mouse anti-Troponin T | Thermo Fisher Scientific | MS-295-P; RRID: AB_61806 |
| CD171 (L1CAM)-APC | Miltenyi Biotec | 130-100-684; RRID: AB_2655584 |
| Anti-PSA-NCAM-APC | Miltenyi Biotec | 130-120-437; RRID: AB_2752096 |
| AlexaFluor Donkey anti-Mouse 488 | Thermo Fisher Scientific | A21202; RRID: AB_141607 |
| AlexaFluor Donkey anti-Rabbit 647 | Thermo Fisher Scientific | A31573; RRID: AB_2536183 |
| AlexaFluor Donkey anti-Rabbit 488 | Thermo Fisher Scientific | A21206; RRID: AB_141708 |
| AlexaFluor Donkey anti-Mouse 568 | Thermo Fisher Scientific | A10037; RRID: AB_2534013 |
| Goat anti-rabbit IgG, HRP conjugated | Thermo Fisher Scientific | 31466; RRID: AB_10960844 |
| Goat anti-mouse IgG, HRP conjugated | Thermo Fisher Scientific | 31431; RRID: AB_10960845 |
| Biological Samples | | |
| 293T | ATCC | CRL-3216 |
| Human lumbar spinal cord tissue sections | Dr. John Ravits' CNS biorepository | N/A |
| Chemicals, Peptides, and Recombinant Proteins | | |
| iPS-Brew XF | Miltenyi Biotec | 130-104-368 |
| DMEM/F12 | Thermo Fisher Scientific | 11320-033 |
| Neuro Medium | Miltenyi Biotec | 130-093-570 |
| RPMI-1640 | Thermo Fisher Scientific | 11879-020 |
| DMEM, high glucose, pyruvate | Thermo Fisher Scientific | 11995081 |
| Seahorse XF Base Medium | Agilent Technologies, Inc. | 102353-100 |

-continued

| Key resources table | | |
|---|---|---|
| REAGENT or RESOURCE | SOURCE | IDENTIFIER |
| NeuroBrew-21 | Miltenyi Biotec | 130-093-566 |
| NeuroBrew-21 w/o Vitamin A | Miltenyi Biotec | 130-097-263 |
| B-27 Supplement, minus insulin | Thermo Fisher Scientific | A1895601 |
| N2 supplement | | |
| Insulin from Bovine Pancreas Powder | Sigma-Aldrich | I6634 |
| Progesterone | Sigma-Aldrich | P8783 |
| Putrescine Dihydrochloride | Sigma-Aldrich | P5780 |
| Selenium Dioxide | Sigma-Aldrich | 200107 |
| Holo-Transferrin | Sigma-Aldrich | T0665 |
| Hydrochloric acid solution | Sigma-Aldrich | 35334 |
| MEM Non-Essential Amino Acids Solution | Thermo Fisher Scientific | 11140050 |
| GlutaMAX Supplement | Thermo Fisher Scientific | 35050061 |
| Accutase | Thermo Fisher Scientific | A1110501 |
| ReLeSR | StemCell Technologies, Inc. | 05872 |
| Trypsin-EDTA (0.25%), phenol red | Thermo Fisher Scientific | 25200056 |
| Fetal Bovine Serum | Thermo Fisher Scientific | 10082147 |
| Matrigel, Basement Membrane Matrix | Corning | 354234 |
| Penicillin-Streptomycin | Thermo Fisher Scientific | 15140122 |
| CHIR99021 | Miltenyi Biotec | 130-103-926 |
| LDN-193189 | Miltenyi Biotec | 130-103-925 |
| Retinoic acid | Sigma-Aldrich | R2625 |
| Purmorphamine | Miltenyi Biotec | 130-104-465 |
| GDNF | Miltenyi Biotec | 130-108-986 |
| BDNF | Miltenyi Biotec | 130-103-435 |
| L-Ascorbic acid | Sigma-Aldrich | A5960 |
| Y27632 | Miltenyi Biotec | 130-103-922 |
| SB431542 | Miltenyi Biotec | 130-105-336 |
| DAPT | Miltenyi Biotec | 130-110-489 |
| IWP-2 | Miltenyi Biotec | 130-105-335 |
| Cytosine β-D-arabinofuranoside | Thermo Fisher Scientific | C1768 |
| Bovine Serum Albumin, Fraction V, pH 7.0 | Capricon Scientific | BSA-1S |
| Phosphate Buffered Saline solution without calcium, magnesium | GE Healthcare | SH30256.02 |
| 0.5M EDTA, pH 8.0 | Thermo Fisher Scientific | AM9260G |
| Riluzole (PK 26124) | Abcam | ab120272 |
| Edaravone | Sigma-Aldrich | M70800 |
| Nicotinamide | Sigma-Aldrich | 72340 |

-continued

| Key resources table | | |
|---|---|---|
| REAGENT or RESOURCE | SOURCE | IDENTIFIER |
| 7-Hydroxy-3-(4'-methoxyphenyl)coumarin (C12) | Apollo Scientific | OR351061 |
| DMSO | Sigma Aldrich | D2650 |
| Lipofectamine 2000 | Thermo Fisher Scientific | 11668019 |
| Lipofectamine ™ RNAiMAX | Thermo Fisher Scientific | 13778150 |
| Lipofectamine ™ Stem | Thermo Fisher Scientific | STEM00008 |
| Paraformaldehyde | Thermo Fisher Scientific | 28908 |
| TritonX-100 | BioRad | 161-0407 |
| Antigen Unmasking Solution, Tris-Based | Vector Laboratories | H-3301 |
| Hematoxylin | Thermo Fisher Scientific | HHS128 |
| Richard-Allan Scientific ™ Mounting Medium | Thermo Fisher Scientific | 4112APG |
| PowerUp ™ SYBRTM ™ Green Master Mix | Thermo Fisher Scientific | A25742 |
| Critical Commercial Assays | | |
| Surveyor mutation detection kit | Integrated DNA Technologies | Cat# 706020 |
| NucleoSpine ® Tissue | Macherey-Nagel | 740952 |
| Plasmid Miniprep Kit | Corning | AP-MN-P-250 |
| Plasmid Maxiprep Kit | Zymo Research | D4202 |
| Seahorse XF Cell Mito Stress Test Kit | Agilent Technologies, Inc. | 103015-100 |
| Seahorse XF Glycolysis Stress Test Kit | Agilent Technologies, Inc. | 103020-100 |
| Mitochondria Isolation Kit, human | Miltenyi Biotec | 130-094-532 |
| NAD/NADH-Glo ™ Assays | Promega | G9071 |
| Complex I Enzyme Activity Microplate Assay Kit | Abcam | ab109721 |
| RNeasy Mini Kit | Qiagen | 74106 |
| High-Capacity cDNA Reverse Transcription Kit | Thermo Fisher Scientific | 4368814 |
| VECTOR ® NovaREDTM ™ Peroxidase (HRP) Substrate Kit | Vector Laboratories | SK-4800 |
| PCR purification kit | Qiagen | 28106 |
| Experimental Models: Cell Lines | | |
| BJ-iPS iPSC | (Ng et al., 2015) | N/A |
| 18a iPSC | Eggan Lab, (Boulting et al., 2011) | N/A |
| GM23720 iPSC | Coriell Institute | GM23720 |
| 29d iPSC | Eggan Lab, (Boulting et al., 2011) | N/A |
| 47a iPSC | Eggan Lab, (Rodriguez-Muela et al., 2017) | N/A |
| 19f iPSC | Eggan Lab, (Kiskinis et al., 2014) | N/A |

-continued

| Key resources table | | |
|---|---|---|
| REAGENT or RESOURCE | SOURCE | IDENTIFIER |
| CS14isALS-Tn16 (sALS1) iPSC | Cedars-Sinai Medical Center's | CS14isALS-Tn16 |
| CS51isALS-Tn3 (sALS2) iPSC | Cedars-Sinai Medical Center's | CS51isALS-Tn3 |
| CS89isALS-Tn16 (sALS3) iPSC | Cedars-Sinai Medical Center's | CS89isALS-Tn16 |
| BJ-SOD1$^{L144F}$ iPSC | This disclosure | N/A |
| BJ-TDP43$^{G298S}$ iPSC | This disclosure | N/A |
| BJ-SIRT3+/-#6 iPSC | This disclosure | N/A |
| BJ-SIRT3+/-#17 iPSC | This disclosure | N/A |
| 1-38G iPSC | Rubin Lab, (Ng et al., 2015) | N/A |
| Oligonucleotides | | |
| SIRT3 siRNA | Santa Cruz | sc-61555 |
| GCN5L1 siRNA | Dharmacon | J-012580-09-0010 |
| SOD1$^{L144F}$ sgRNA (CACCGAGGAAACGCTGGAAGTCGTT) (SEQ ID NO: 21) | Integrated DNA Technologies | N/A |
| SODL$^{144F}$ ssODN (ACATCCAAGGGAATGTTTATTGGGCGA TCCCAATTACACCACAAGCGAAACGACT TCCAGCGTTTCCTGTCTTTGTACTTTCTT CATTTCCACCTTTGCC) (SEQ ID NO: 22) | Integrated DNA Technologies | N/A |
| SOD1$^{L144F}$ surveyor F: (TAAGGGTAGCGTGTGGTGGT) (SEQ ID NO: 23) SOD1$^{L144F}$ surveyor R: (TGCTTAGACAAATAGGCTGTCC) (SEQ ID NO: 24) | Integrated DNA Technologies | N/A |
| TDP43$^{G298S}$ sgRNA (CACCGTTTGGTAATAGCAGAGGGGG) (SEQ ID NO: 25) | Integrated DNA Technologies | N/A |
| TDP43G$^{298S}$ ssODN (TTTGGGAATCAGGGTGGATTTGGTAAT AGCAGAGGGGGTGGAGCTGGTTTGGG AAACAATCAAGGTAGTAATATGGGTGGT GGGATGAACT) (SEQ ID NO: 26) | Integrated DNA Technologies | N/A |
| TDP43$^{G298S}$ surveyor F (CCACTACGCCCAGCTAATGT) (SEQ ID NO: 27) | Integrated DNA Technologies | N/A |
| TDP43$^{G298S}$ surveyor F (TCTGGCTGGGGAATGTAGAC) (SEQ ID NO: 28) | Integrated DNA Technologies | N/A |
| SIRT3$^{+/-}$ sgRNA (CTTCCGGCGCCGAGCGGCGCGG) (SEQ ID NO: 29) | Integrated DNA Technologies | N/A |
| SIRT3$^{+/-}$ surveyor F: (GGCGCTCACTTCTTCGTGTA) (SEQ ID NO: 30) SIRT3$^{+/-}$ surveyor R: (AGACGTAGAGGCGAGTAGAGGA) (SEQ ID NO: 31) | Integrated DNA Technologies | N/A |

-continued

| Key resources table | | |
|---|---|---|
| REAGENT or RESOURCE | SOURCE | IDENTIFIER |
| CHOP qPCR F: (AAGGCACTGAGCGTATCATGT) (SEQ ID NO: 32) CHOP qPCR R: (TGAAGATACACTTCCTTCTTGAACA) (SEQ ID NO: 33) | (Ng et al., 2015) | N/A |
| sXBP1 qPCR F: (TGCTGAGTCCGCAGCAGGTG) (SEQ ID NO: 34) sXBP1 qPCR R: (GCTGGCAGGCTCTGGGGAAG) (SEQ ID NO: 35) | (Ng et al., 2015) | N/A |
| ACTB qPCR F: (CCAACCGCGAGAAGATGA) (SEQ ID NO: 36) ACTB qPCR R: (CCAGAGGCGTACAGGGATAG) (SEQ ID NO: 37) | (Ng et al., 2015) | N/A |
| HPRT qPCR F: (TATGGCGACCCGCAGCCCT) (SEQ ID NO: 38) HPRT qPCR R: (CATCTCGAGCAAGACGTTCAG) (SEQ ID NO: 39) | Integrated DNA Technologies | N/A |
| Recombinant DNA (plasmids) | | |
| pSpCas9(BB)-2A-GFP (PX458) | Addgene | RRID: Addgene_48138 |
| pSpCas9(BB)-2A-Puro (PX459) V2.0 | Addgene | RRID: Addgene_62988 |
| Software and Algorithms | | |
| FIJI-ImageJ | (Schindelin et al., 2012) | https://fiji.sc/ |
| Columbus | Perkin Elmer | N/A |
| Harmony | Perkin Elmer | HH17000010 |
| Other | | |
| Seahorse XFe96 FluxPak | Agilent Technologies, Inc. | 102416-100 |
| cOmplete ™, Mini, EDTA-free Protease Inhibitor Cocktail | Sigma Aldrich | 04693159001 |
| LS columns | Miltenyi Biotec | 130-042-401 |
| Anti-APC MicroBeads | Miltenyi Biotec | 130-090-855 |

*This table is intended to be illustrative and not restrictive of the materials that may be used.

Culture of hiPSC in iPS-Brew hPSC Medium

All hiPSC lines were cultured feeder-free on Matrigel-coated dishes with iPS-Brew XF according to product's instructions. Routine passaging using ReLeSR (Stem Cell Technologies) was performed once every 6-7 days. The iPSC lines, and their mutations, used in this study are listed in Table S1 below.

TABLE S1

| List of cell lines used | | |
|---|---|---|
| Cell Lines | Source | Catalog no. |
| BJ-iPS iPSC | Ng et al. (2015) | N/A |
| 18a iPSC | Eggan Lab, Boulting et al. (2011) | N/A |

TABLE S1-continued

| List of cell lines used | | |
|---|---|---|
| Cell Lines | Source | Catalog no. |
| GM23720 iPSC | Coriell Institute | GM23720 |
| 29d iPSC ($SOD1^{L144F}$) | Eggan Lab, Boulting et al. (2011) | N/A |
| 47a iPSC ($TDP43^{G298S}$) | Eggan Lab, Rodriguez-Muela et al. (2017) | N/A |
| 19f iPSC (C9ORF72) | Eggan Lab, Kiskinis et al. (2014) | N/A |
| CS14isALS-Tn16 (sALS1) iPSC | Cedars-Sinai Medical Center's | CS14isALS-Tn16 |
| CS51isALS-Tn3 (sALS2) iPSC | Cedars-Sinai Medical Center's | CS51isALS-Tn3 |
| CS89isALS-Tn16 | Cedars-Sinai Medical | CS89isALS- |

TABLE S1-continued

| List of cell lines used | | |
|---|---|---|
| Cell Lines | Source | Catalog no. |
| (sALS3) iPSC | Center's | Tn16 |
| BJ-SOD1$^{L144F}$ iPSC | This disclosure | N/A |
| BJ-TDP43$^{G298S}$ iPSC | This disclosure | N/A |
| BJ-SIRT3+/−#6 iPSC | This disclosure | N/A |
| BJ-SIRT3+/−#17 iPSC | This disclosure | N/A |

Directed Differentiation Toward Motor Neurons

Pluripotent stem cells were differentiated towards the spinal motor neuron fate following established protocols described previously (4). Briefly, the human iPSC was first neuralized by activating Wnt pathways with CHIR99021 treatment (4.25 μM) while blocking Bone Morphogenic Protein (BMP) signaling by LDN-193189 treatment (0.5 μM) at the same time. At day 3, retinoic acid (1 μM) and Purmorphamine (1 μM), were used to caudalize and ventralize the cultures respectively. Neurotrophic factors, BDNF (10 ng/ml) and GDNF (10 ng/ml), were added to the neuronal cultures at day 17 to promote neuronal maturation into motor neurons. N2B27 media (50% DMEM/F12, 50% Neuro medium, 1% L-Glutamax, 1% MEM Non-Essential Amino Acids supplemented with 1% N2 supplement and 2% B27 supplement) was used throughout the motor neuron differentiation.

Directed Differentiation Toward Cortical Neurons

Pluripotent stem cells were differentiated towards the cortical neuron fate following established protocols described previously (5) with slight modifications. The human iPSC was first neuralized with SB431542 treatment (8 μM) to inhibit TGF-β pathway while blocking Bone Morphogenic Protein (BMP) signaling with LDN-193189 treatment (0.5 μM) at the same time. At day 14, cortical neural progenitors were further differentiated with the addition of DAPT (2.5 μM) for another 7 days. Neurotrophic factors, BDNF (10 ng/ml) and GDNF (10 ng/ml), were added to the neuronal cultures at day 21 to promote neuronal maturation into cortical neurons. N2B27 media lacking vitamin A (50% DMEM/F12, 50% Neuro medium, 1% L-Glutamax, 1% MEM Non-Essential Amino Acids supplemented with 1% N2 supplement and 2% B27 supplement without vitamin A) was used throughout the cortical neuron differentiation.

Directed Differentiation Toward Cardiomyocytes

Pluripotent stem cells were differentiated towards the cardiomyocytes fate following established protocols described previously (6). Briefly, the human iPSC was first directed to mesendoderm by activating Wnt pathways with CHIR99021 treatment (12 μM) for one day in RPMI/B27 lacking insulin. To direct these mesendoderm progenitor cells to a cardiac fate, IWP2 (5 μM) was added to the cultures for two days in RPMI/B27 lacking insulin on day 3. At day 7, cardiac mesoderm cells were cultured in RPMI/B27 with insulin for development of functional contracting cardiomyocytes.

Cas9-Mediated Knockout/Knockin in BJ-iPS Line

Guide RNAs (gRNAs) were designed using Feng Zhang lab's guide design tool at crispr.mit.edu before it shut down: gRNAs were cloned into a Cas9-containing plasmid PX458 or PX459 and transfected into 293T cells using Lipofectamine 2000 Transfection Reagent for surveyor nuclease assay. Verified gRNAs and ssODNs (Table S2) were transfected into BJ-iPS hiPSCs using Lipofectamine Stem Transfection Reagent. 2 days after transfection, cultures were sorted for GFP+ cells or selected with 1 μM puromycin. Single cells were then plated out and allowed to expand before screening. gDNA of the colonies were collected and subjected to PCR amplification before sanger sequencing (Applied Biosystems 3730xl).

TABLE S2

| List of oligonucleotides used for CRISPR/Cas9 studies | |
|---|---|
| Oligonucleotides (CRISPR) | Source |
| SOD1$^{L144F}$ sgRNA (CACCGAGGAAACGCTGGAAGTCGTT) (SEQ ID NO: 21) | Integrated DNA Technologies |
| SOD1$^{L144F}$ ssODN (ACATCCAAGGGAATGTTTATTGGGCGATCCCAA TTACACCACAAGCGAAACGACTTCCAGCGTTTCC TGTCTTTGTACTTTCTTCATTTCCACCTTTGCC) (SEQ ID NO: 22) | Integrated DNA Technologies |
| SOD1$^{L144F}$ surveyor F: (TAAGGGTAGCGTGTGGTGGT) (SEQ ID NO: 23) SOD1$^{L144F}$ surveyor R: (TGCTTAGACAAATAGGCTGTCC) (SEQ ID NO: 24) | Integrated DNA Technologies |
| TDP43$^{G298S}$ sgRNA (CACCGTTTGGTAATAGCAGAGGGGG) (SEQ ID NO: 25) | Integrated DNA Technologies |
| TDP43$^{G298S}$ ssODN (TTTGGGAATCAGGGTGGATTTGGTAATAGCAGA GGGGGTGGAGCTGGTTTGGGAAACAATCAAGGTA GTAATATGGGTGGTGGGATGAACT) (SEQ ID NO: 26) | Integrated DNA Technologies |
| TDP43$^{G298S}$ surveyor F (CCACTACGCCCAGCTAATGT) (SEQ ID NO: 27) | Integrated DNA Technologies |
| TDP43$^{G298S}$ surveyor F (TCTGGCTGGGGAATGTAGAC) (SEQ ID NO: 28) | Integrated DNA Technologies |
| SIRT3$^{+/-}$ sgRNA (CTTCCGGCGCCGAGCGGCGCGG) (SEQ ID NO: 29) | Integrated DNA Technologies |
| SIRT3$^{+/-}$ surveyor F: (GGCGCTCACTTCTTCGTGTA) (SEQ ID NO: 30) SIRT3$^{+/-}$ surveyor R: (AGACGTAGAGGCGAGTAGAGGA) (SEQ ID NO: 31) | Integrated DNA Technologies |

Motor Neuron Survival Assay

Motor neuron cultures were treated with AraC on Day 23 and plated at 75,000 cells per well of a 96 well plate on Day 24. Cultures were then fixed with 4% PFA on Day 25, 28, 31 and 35 respectively for quantification of motor neuron survival. Fixed cultures were stained with the motor neuron marker ISL1, and cellular nuclei were counterstained with DAPI before imaging on the high content microscope Phenix (Perkin Elmer). Percentage of ISL1+ cells was normalized to total nuclei number. To calculate normalized survival index, the percentage of ISL1+/DAPI at day 25 was arbitrary set as 1.0, and motor neuron survival on later days were in turn normalized to day 25 cultures. Biological triplicates were performed with a minimum of 5 technical replicates each.

Magnetic Microbead Sorting of Neurons

After dissociating with Accutase, cells were blocked with solution containing phosphate-buffered saline, 0.5% bovine serum albumin (BSA) and 2 mM EDTA. The cells were then incubated with CD171-APC antibody (Miltenyi Biotec) and PSA-NCAM-APC antibody (Miltenyi Biotec) for 10 mins at 4° C. After washing, the cells were then incubated with anti-APC microbeads for 15 minutes at 4° C. The cells were then washed twice and filtered prior to loading into the separation column (LS column) that was attached to a magnetic stand (all from Miltenyi Biotec). After three rounds of washing, the column was removed from the magnetic stand and labelled cells were eluted in culture media for replating.

Metabolic Flux Analyses Using Seahorse XFe96 Analyzer

Mitochondrial oxygen consumption rates (OCR) and extracellular acidification rates (ECAR) were measured using a XFe96 Seahorse Biosciences Extracellular Flux Analyzer (Agilent Technologies). Purified motor neurons or neural progenitor cells were plated onto a Matrigel pre-coated Seahorse 96-well plate at 125,000 neurons per well 24 hours prior to the assay. Culture media were changed with 175 ul of fresh Seahorse DMEM basal medium 45 minutes prior to the assay. Seahorse analyzer injection ports were filled with 1 μM oligomycin, 1 μM FCCP or 0.5 μM each of rotenone and antimycin A for OCR. For ECAR, 10 mM glucose, 1 μM oligomycin and 50 mM 2-DG were used, following the manufacturer's instructions. Levels of OCR and ECAR were recorded, normalized and quantified based on manufacturer's instructions. Biological triplicates were performed with a minimum of 5 technical replicates each.

Small Molecule Treatments in MN Cultures

Riluzole was reconstituted in DMSO was used at a final concentration of 5 μM based on previous work (7) while Edaravone was dissolved in water and used at a final concentration of 100 μM (8). NAM and C12 were reconstituted in water and DMSO respectively and diluted in media at the desired concentrations of 0.5 mM (9) and 5 μM respectively. Motor neurons at day 27 were plated at 75,000 cells per well of a 96-well plate. Treatment with the respective small molecule began at day 28, for a total of 3 days. Biological triplicates were performed with a minimum of 5 technical replicates each.

RNA Interference in MN Cultures

Motor neuron cultures at day 27 were dissociated with Accutase and seeded at 2 million cells per well in a 6-well plate. At day 28, non-targeting siRNA or siRNAs were individually complexed with Lipofectamine RNAiMAX following manufacturer's instructions and added to the motor neuron cultures. For each well, 10 pmol of siRNAs and 8 μl of Lipofectamine RNAiMAX were used. Cells were either harvested for RNA and protein analyses, fixed for immunostaining or metabolic flux analysis were performed 3 days after siRNA transfection.

RNA Extraction and RT-qPCR

Cells were harvested in Trizol reagent for RNA extraction following manufacturer's instructions. Purified RNA was converted to cDNA using the High-Capacity cDNA Reverse Transcription kit, and quantitative PCR (qPCR) was performed on the QuantStudio 5 Real-Time PCR System using PowerUp™ SYBR™ Green Master Mix (all from Applied Biosystems). Gene expressions were normalized to HPRT and ACTB expression unless otherwise stated. Primers used are listed in Table S3.

TABLE S3

List of human primers used in qPCR studies

| Oligonucleotides (qPCR) | Source |
|---|---|
| CHOP qPCR F: (AAGGCACTGAGCGTATCATGT) (SEQ ID NO: 32) CHOP qPCR R: (TGAAGATACACTTCCTTCTTGAACA) (SEQ ID NO: 33) | Ng et al. (2015) |
| sXBP1 qPCR F: (TGCTGAGTCCGCAGCAGGTG) (SEQ ID NO: 34) sXBP1 qPCR R: (GCTGGCAGGCTCTGGGGAAG) (SEQ ID NO: 35) | Ng et al. (2015) |
| ACTB qPCR F: (CCAACCGCGAGAAGATGA) (SEQ ID NO: 36) ACTB qPCR R: (CCAGAGGCGTACAGGGATAG) (SEQ ID NO: 37) | Ng et al. (2015) |
| HPRT qPCR F: (TATGGCGACCCGCAGCCCT) (SEQ ID NO: 38) HPRT qPCR R: (CATCTCGAGCAAGACGTTCAG) (SEQ ID NO: 39) | Integrated DNA Technologies |

SDS-PAGE and Western Blot

Protein lysates were resolved in 12% SDS-PAGE gels or 4-20% precast gels in Tris-Glycine-SDS buffer. Proteins were then transferred to a nitrocellulose membrane and blocked with 5% milk in TBST buffer. Primary antibodies were diluted in 5% milk and incubated with the membranes overnight at 4° C. Primary antibodies used are listed in Table S4. Membranes were washed thrice in TBST buffer. The corresponding horseradish peroxidase secondary antibodies (Life Technologies) were then diluted 1:5000 in 5% milk and incubated at room temperature for 90 minutes. Blots were washed thrice before exposing to ECL for imaging.

TABLE S4

List of antibodies used in western blot and immunostaining studies

| Antibodies | | |
|---|---|---|
| Rabbit anti-SirT3 (D22A3) | Cell Signaling | 5490 |
| Mouse anti-alpha tubulin (B-7) | Santa Cruz | sc-5286 |
| Mouse Anti-TOMM20 | Abcam | ab56783 |
| Rabbit anti-Islet 1 [EP4182] | Abcam | ab109517 |
| Mouse anti-SMI-32 | BioLegend | 801701 |
| Rabbit anti-Acetylated-Lysine | Cell Signaling | 9814 |
| Rabbit anti-SOD2/MnSOD | Abcam | ab13533 |
| Rabbit anti- SOD2/MnSOD (acetyl K68) | Abcam | ab137037 |
| Rabbit anti-SATB2 [EPNCIR130A] | Abcam | ab92446 |
| Goat anti-BRN2 (C-20) | Santa Cruz | sc-6029 |
| Rabbit anti-FOXG1 | Abcam | ab18259 |
| Rabbit anti-SOX1 | Abcam | ab87775 |
| Mouse anti-NESTIN [10C2] | Abcam | ab22035 |
| Rabbit anti-Doublecortin | Abcam | ab18723 |
| Mouse anti-TUJ1 | BioLegend | 801201 |
| Mouse anti-Troponin T | Thermo Fisher Scientific | MS-295-P |
| CD171 (L1CAM)-APC | Miltenyi Biotec | 130-100-684 |

TABLE S4-continued

| List of antibodies used in western blot and immunostaining studies | | |
|---|---|---|
| Antibodies | | |
| Anti-PSA-NCAM-APC | Miltenyi Biotec | 130-120-437 |
| AlexaFluor Donkey anti-Mouse 488 | Thermo Fisher Scientific | A21202 |
| AlexaFluor Donkey anti-Rabbit 647 | Thermo Fisher Scientific | A31573 |
| AlexaFluor Donkey anti-Rabbit 488 | Thermo Fisher Scientific | A21206 |
| AlexaFluor Donkey anti-Mouse 568 | Thermo Fisher Scientific | A10037 |
| Goat anti-rabbit IgG, HRP conjugated | Thermo Fisher Scientific | 31466 |
| Goat anti-mouse IgG, HRP conjugated | Thermo Fisher Scientific | 31431 |

Cellular Thermal Shift Assay (CETSA)

CETSA was performed as previously described (3) and HEK293T cells were used to carry out the experiment. Briefly, 30 million cells were exposed to a final concentration of 20 μM C12 or DMSO for 1 hour on low-attachment plates. After the incubation, the cells were harvested, washed, pellet down and resuspended in 1 mL of PBS. Equal amounts of cell suspensions were aliquoted into Eppendorf tubes. The cell suspensions were then heated (48-68° C.) and lysed using 2 cycles of freeze-thawing. The soluble fractions were isolated and analyzed by Western blot analysis as described above.

Mitochondria Isolation

Mitochondria from motor neuron cultures were isolated using the MACS technology. Motor neurons culture were first Accutase and wash twice with PBS before resuspending in ice cold Lysis buffer. The cells were then homogenized with a dounce homogenizer (Pestle B) 15 strokes. The homogenate was diluted with 1× separation buffer based on manufacturer's instructions. Anti-TOM22 were added to magnetically label the mitochondria before incubating at 4° C. for 1 hour. The cells were then washed twice and filtered prior to loading into the separation column (LS column) that was attached to a magnetic stand (all from Miltenyi Biotec). After three rounds of washing, the column was removed from the magnetic stand and labelled mitochondria were eluted in storage buffer for downstream applications.

Measurements of Complex I Activity

Cell lysates were prepared using Complex I Enzyme Activity Microplate Assay Kit (Abcam), following the manufacturer's instructions. Activity of Complex I was recorded, normalized and quantified based on manufacturer's instructions. Biological triplicates were performed with a minimum of 3 technical replicates each.

NAD+/NADH Quantification

Purified motor neurons were plated onto a Matrigel pre-coated 96-well plate at 50,000 neurons per well 24 hours prior to the assay. Cultures were then prepared for NAD+/NADH measurement using NAD/NADH-Glo™ Assay (Promega) following manufacturer's instructions. Levels of NAD+/NADH were recorded, normalized and quantified based on manufacturer's instructions. Biological triplicates were performed with a minimum of 3 technical replicates each.

Mitochondrial $NAD^+$ Quantification

Mitochondria from motor neuron cultures (10 million cells) were isolated using the MACS technology (as described above). Mitochondrial NAD+ was prepared quantified using NAD/NADH-Glo™ Assay (Promega) following manufacturer's instructions. Briefly, isolated mitochondria were first diluted in PBS, bicarbonate base buffer and 1% DTAB in a ratio of 2:1:1. 0.4N of HCl was added to the mitochondrial suspension prior to heating at 60° C. for 15 mins. After heating, 0.5M of Trizma base was added to the suspension and levels of mitochondrial $NAD^+$ were recorded, normalized to $NAD^+$ standard curve and quantified based on manufacturer's instructions (Promega). Biological triplicates were performed with a minimum of 3 technical replicates each.

Immunostaining of Cultured Cells

Cells were fixed in 4% paraformaldehyde for 15 minutes, permeabilized in 0.1% Triton X-100 for 15 minutes and blocked in buffer containing 5% FBS and 1% BSA for an hour at room temperature. Primary antibodies (Table S4) were diluted in blocking buffer and incubated overnight at 4° C. Cells were washed thrice in PBS. The respective secondary antibodies were diluted 1:1500 in blocking buffer and incubated at room temperature, in the dark, for 90 minutes. DAPI was used at 0.1 μg/ml to visualize cellular nuclei.

Immunohistochemistry Using ALS Patient Tissues

Lumbar spinal cord tissue sections were cut from blocks of paraffin embedded ALS tissue (n=4) and control tissue (n=4), obtained from UCSD CNS biorepository. Six m-thick tissue sections were de-paraffinized with histology grade CitriSolv (twice for 15 minutes each), followed by a graded alcohol series (100, 90, 70, and 50% ethanol (vol/vol) for 3 min each), then washed in water (twice for 3 min). Endogenous peroxidase activity was then quenched in 0.6% hydrogen peroxide in methanol (vol/vol) for 15 min. After a 20 min permeabilization step in 1×PBS, 0.2% TritonX100, antigen retrieval was performed in a pressure cooker at 120° C. for 20 min in high pH solution (1% Tris-based). Sections were blocked with 2% Fetal Bovine Serum (vol/vol) and incubated with MnSOD (K68ac) antibody (1:100) overnight at 4° C.

The following day after equilibration to room temperature, sections were washed three times in 1×PBS before 60 min room temperature incubation with 150 μl secondary antibody. Signals were detected via chromogenic reaction using NovaRed for 1-3 minutes per section until desired staining was achieved. Counterstaining was performed with hematoxylin for 10 seconds. Sections were dehydrated before adding cover slips.

Image Acquisition and Image Analysis

Images were acquired using the high content microscope Phenix (Perkin Elmer) using the 20× air objective. Image analyses including cell counts and intensity measurements were performed using Columbus (Perkin Elmer).

For primary neurites analysis, neuronal projections from the soma size was determined based on SMI-32 staining. For soma size analysis, cellular nuclei were identified by DAPI, and the cytoplasmic area surrounding the nucleus was determined based on SMI-32 staining. Soma size area was measured by image analysis software (ImageJ, NIH) based on the cytoplasmic area surrounding the nucleus, excluding neuronal projections.

For patient tissues, all slides were scanned with Hamamatsu Nanozoomer 2.0HT Slide Scanner at the UCSD Microscopy Core. Using NDP.view 2 viewing software, scanned slides were evaluated at 1× and 20× magnifications. All neurons were evaluated in both anterior horn sections from a total of four, non-sequential tissue sections per patient, in order to ensure no overlap in neurons. K68Ac expression patterns and intensity were determined for all neurons using Fiji. Color deconvolution was performed using "H DAB" as the defined vector. Neurons were measured and quantification performed using "Colour_2" representing the VectorRed signal without the background from the counterstain (Colour_1 is hematoxylin). The region of interest was determined for each neuron and "Mean gray value" was used to quantify intensity. In order to convert intensity to Optical Density (OD) the formula used was: OD=log (Max intensity/Mean intensity) for 8-bit images. The resulting OD quantified the average darkness of the image due to DAB signal (thus representing MnSOD-K68ac stain).

Statistical Analyses

At least three biological replicates were performed for each experiment. Measurements were taken from distinct samples for analysis. Statistical analysis comparing two groups were performed by means of a two-tailed unpaired Student's t test. P values lower than 0.05 were considered significant. All results are presented as mean±standard deviation unless otherwise specified.

Human Ethics Statement

All tissues were collected under HIPAA (Health Insurance Portability and Accountability Act of 1996) compliant IRB (Institutional Review Board) supervised consenting process. Patients are provided the option to donate their CNS tissue postmortem to the ALS biorepository and provide consent during life. All consent forms and other legal documentation is handled by clinical research support staff and kept de-identified from the basic research team. Each patient has separate clinical, CNS and fibroblast identifiers assigned to them in order to maintain patient autonomy and anonymity.

REFERENCES

1. Boulting G L, Kiskinis E, Croft G F, Amoroso M W, Oakley D H, Wainger B J, et al. A functionally characterized test set of human induced pluripotent stem cells. Nat Biotechnol. 2011; 29(3):279-86.
2. Kiskinis E, Sandoe J, Williams L A, Boulting G L, Moccia R, Wainger B J, et al. Pathways disrupted in human ALS motor neurons identified through genetic correction of mutant SOD1. Cell Stem Cell. 2014; 14(6):781-95.
3. Jafari R, Almqvist H, Axelsson H, Ignatushchenko M, Lundback T, Nordlund P, et al. The cellular thermal shift assay for evaluating drug target interactions in cells. Nat Protoc. 2014; 9(9):2100-22.
4. Hor J H, Soh E S, Tan L Y, Lim V J W, Santosa M M, Winanto, et al. Cell cycle inhibitors protect motor neurons in an organoid model of Spinal Muscular Atrophy. Cell Death Dis. 2018; 9(11):1100.
5. Muratore C R, Srikanth P, Callahan D G, Young-Pearse T L. Comparison and optimization of hiPSC forebrain cortical differentiation protocols. PLoS One. 2014; 9(8): e105807.
6. Lian X, Zhang J, Azarin S M, Zhu K, Hazeltine L B, Bao X, et al. Directed cardiomyocyte differentiation from human pluripotent stem cells by modulating Wnt/beta-catenin signaling under fully defined conditions. Nat Protoc. 2013; 8(1):162-75.
7. Sperling S, Aung T, Martin S, Rohde V, Ninkovic M. Riluzole: a potential therapeutic intervention in human brain tumor stem-like cells. Oncotarget. 2017; 8(57): 96697-709.
8. Lee B J, Egi Y, van Leyen K, Lo E H, Arai K. Edaravone, a free radical scavenger, protects components of the neurovascular unit against oxidative stress in vitro. Brain Res. 2010; 1307:22-7.
9. Schondorf D C, Ivanyuk D, Baden P, Sanchez-Martinez A, De Cicco S, Yu C, et al. The NAD+ Precursor Nicotinamide Riboside Rescues Mitochondrial Defects and Neuronal Loss in iPSC and Fly Models of Parkinson's Disease. Cell Rep. 2018; 23(10):2976-88.
10. Ng S Y, Soh B S, Rodriguez-Muela N, et al. Genome-wide RNA-Seq of Human Motor Neurons Implicates Selective ER Stress Activation in Spinal Muscular Atrophy. *Cell Stem Cell.* 2015; 17(5):569-584. doi:10.1016/j.stem.2015.08.003.
11. Rodriguez-Muela N, Litterman N K, Norabuena E M, et al. Single-Cell Analysis of SMN Reveals Its Broader Role in Neuromuscular Disease. *Cell Rep.* 2017; 18(6):1484-1498. doi:10.1016/j.celrep.2017.01.035.
12. Schindelin J, Arganda-Carreras I, Frise E, et al. Fiji: an open-source platform for biological-image analysis. *Nat Methods.* 2012; 9(7):676-682. Published 2012 Jun. 28. doi:10.1038/nmeth.2019.

APPLICATIONS

Motor neurons are highly energetic cells. They rely mainly on oxidative phosphorylation to fuel their high metabolic demands, and any deviation from this norm may lead to neurological disorders. By use of induced pluripotent stem cells (iPSCs) from healthy controls, familial ALS and sporadic ALS patients (including isogenic pairs) differentiated towards spinal MNs, cortical neurons and cardiomyocytes, the inventors demonstrated that altered energy metabolism precedes motor neuron loss and identified clear mechanistic insights linking altered metabolism and motor neuron death in ALS, a motor neuron disease. Defective mitochondrial respiration was demonstrated to be a common pathway implicated in both sporadic and familial ALS.

A method to enrich for the above-mentioned MNs was developed for metabolic flux measurements. In various examples, by excluding neural progenitor cells (NPCs) refractory to differentiation and other non-neuronal cells in the metabolic assays, the inventors identified reduced mitochondrial respiration/hypo-oxidation and elevated glycolysis/hyperglycolysis as a metabolic hallmark of ALS MNs, which were not observed in the NPCs. In various examples, metabolic flux analyses reveal a motor neuron-specific deficiency in mitochondrial respiration in ALS. In various examples, all forms of familial and sporadic ALS MNs tested exhibited similar defective metabolic profiles/mitochondrial respiration, which were attributed to hyper-acetylation of mitochondrial proteins.

In the mitochondria, SIRT3 functions as a mitochondrial deacetylase to maintain mitochondrial function and integrity, while GCN5L1 is a mitochondrial-enriched acetyltransferase that catalyzes the reaction antagonistic to SIRT3 or counters the acetylation and respiratory effects of SIRT3. In various examples, mitochondrial hyperacetylation was shown to be regulated by the deacetylase SIRT3 and GCN5L1, which promotes mitochondrial protein acetylation. In various examples, SIRT3 haploinsufficient motor neurons recapitulate an ALS-like phenotype. In various examples, activating SIRT3 e.g. using nicotinamide or a small molecule activator or inhibition of GCN5L1 were able to reverse the defective metabolic profiles in all the ALS motor neurons, as well as correct a constellation of ALS-associated phenotypes/morphologies. In some examples, SIRT3 activation promotes ALS MN survival and neurite outgrowth by restoring healthy mitochondrial respiration but does not rescue SMA. Correspondingly, in various examples, knockdown/depletion of GCN5L1 in ALS motor neurons also rescues ALS-associated phenotypes/morphologies, promotes motor neuron survival and neurite outgrowth by promoting healthy levels of mitochondrial respiration.

The inventors have demonstrated that hyper-acetylated mitochondrial protein is a hallmark of both sporadic and familial ALS and have identified the SIRT3-GCN5L1 axis as a common pathogenic node in both familial and sporadic ALS. Advantageously, the disclosure reveals that targeting the SIRT3-GCN5L1 axis to modulate mitochondrial protein acetylation (e.g. by elevating SIRT3 activity and/or inhibiting GCN5L1) makes a promising therapeutic strategy for ALS.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A method of promoting survival and/or function of an amyotrophic lateral sclerosis (ALS) motor neuron, the method comprising contacting the motor neuron with an agent capable of reducing mitochondrial protein acetylation, wherein the agent is an acetyltransferase inhibitor comprising a GCN5L1 (GCN5 (general control of amino acid synthesis 5)-like 1) inhibitor comprising an oligonucleotide that is selected from an oligonucleotide comprising complementary to a CDS of BLOC1S1 gene, or SEQ ID NO: 3, or SEQ ID NO: 4; or a sequence sharing at least 95% sequence identity thereof, or an oligonucleotide comprising a sequence sharing at least 95% sequence identity with SEQ ID NO: 1, or a sequence differing from SEQ ID NO: 1 by no more than, 1, 2, 3, 4, or 5 nucleotides.

2. The method of claim 1, wherein the GCN5L1 inhibitor comprises an oligonucleotide selected from the group consisting of: antisense oligonucleotide (ASO), gapmer, short interfering RNA (siRNA), short hairpin RNA (shRNA), microRNA (miRNA), guide RNA (gRNA), single guide RNA (sgRNA) and combinations thereof.

3. The method of claim 1, wherein GCN5L1 inhibitor comprises an oligonucleotide comprising:

a) a sequence that is complementary to a coding sequence (CDS) of BLOC1S1 gene, or SEQ ID NO: 3, or SEQ ID NO: 4; or b) a sequence sharing at least 95% sequence identity with the sequence in a).

4. The method of claim 1, wherein the GCN5L1 inhibitor comprises an oligonucleotide comprising a sequence sharing at least 95% sequence identity with SEQ ID NO: 1, or a sequence differing from SEQ ID NO: 1 by no more than, 1, 2, 3, 4, or 5 nucleotides.

5. The method of claim 1, wherein, the method further comprising treating ALS in a subject in need thereof, wherein said treatment comprises administering the agent capable of reducing mitochondrial protein acetylation into the subject.

6. The method of claim 2, wherein the oligonucleotide comprises a sequence sharing at least 95% sequence identity with SEQ ID NO: 1, or a sequence differing from SEQ ID NO: 1 by no more than, 1, 2, 3, 4, or 5 nucleotides.

7. The method of claim 3, wherein the oligonucleotide comprises a sequence sharing at least 95% sequence identity with SEQ ID NO: 1, or a sequence differing from SEQ ID NO: 1 by no more than, 1, 2, 3, 4, or 5 nucleotides.

8. The method of claim 1, wherein the oligonucleotide comprises SEQ ID NO: 1, or a sequence differing from SEQ ID NO: 1 by no more than, 1, 2, 3, 4, or 5 nucleotides.

* * * * *

```
SEQUENCE LISTING

<160> NUMBER OF SEQ ID NOS: 39

<210> SEQ ID NO 1
<211> LENGTH: 19
<212> TYPE: RNA
<213> ORGANISM: Artificial Sequence
<220> FEATURE:
<223> OTHER INFORMATION: oligonucleotide

<400> SEQUENCE: 1

agaggaggcg agaggcuau                                              19


<210> SEQ ID NO 2
<211> LENGTH: 4776
<212> TYPE: DNA
<213> ORGANISM: Homo sapiens

<400> SEQUENCE: 2

gcttctgcta acactgaaat gggttcgcat tcctgaccac aaaaggacag agatgaaatt     60

ctacattcac acagcccgcc aagttagcca agctccctag gaggctgtct gaagtgccta    120

aaatgcttct ctacaatgat cacccagagc tgagagactt cagtggggta gtgagaagaa    180

agagggttgg gagagacagg aaagcatcct ctccttgagg gaaggaactg ggaatcaact    240

gagaaccagc tagcactgcc aggaggtgag gagagggaag gagaataatt taaatgaggc    300

cagggagctt ctgctccctc aattaaacgg tgatagacgg cctgacacca ccagccctcg    360

aagcctgaga tccacaggaa atgttaaaaa ctggcttggc aatataagta ttagaaaata    420

cttcttccaa cactcaccaa aaactaagct cccaataaag aacacttcac ctgccctccg    480

caaccctcta cctctcttcc ccgccaagat cttcacccaa ggtctcaaga gggcggttcc    540

caacctcacg tgacacagcg gtcacgtgac atggccccgg ggagccgagg tgagcgttcc    600

agcttccgga gccggagggg gcccggcgta cccagccccc agcccgacgt gaccatgctg    660

tcccgcctcc taaaagaaca ccaggccaag cagaatgaac gcaaggagct gcagggtgag    720

ccaaatatcc tgtcggccgt tttctcttcg gccgcggcct agcttcagcc cggagcctgg    780

atctcgagta actaaccata tccagggaaa gacgccagct agcgggcaac gggcatgggg    840

gagagggaat ttcagagagg cttttttga aactcctttc ccttgccaac tggctccggt     900

cccttgggca atactccggt cccctcggca acgcccccaa tccccgacct gccgcacctt    960

agccccgccc ctgccccgga gcgccctgcc tattggccct gggagcctct cgtcctggcg   1020

gcgggaagga gcgactctgg agggaggagg gtgtggggaa ccccccagag atgggcttct   1080

tggaggcctg aaaccaccgg aacggaggtg gggcacttgt ttcctgagtc cgggctggaa   1140

atctcggagt taccgattct gcggccgagt agtggagaaa gagtgcctgg gagtcaggag   1200

tcctgggcgc tgccgctgac ttcctggcgt ccctgagtga gtccatttcc ctcccagggt   1260
```

accagtttcc tcatctctaa aatgaaagag gttgcgctat gttttgcaag gtccttttca 1320
gctccggcat tcagagatta gttaagaaat ttcggcaact agcagaatag taatggatgg 1380
gtagggaacc tttaacacta cccctcaaaa aaccaagtct cccctccaat tccttttccc 1440
cctctcccca gaaaagagga ggcgagaggc tatcactgca gcgacctgcc tgacagaagc 1500
tttggtggat cacctcaatg tggggtatgg acctcttatc aacatcagtt tcctccttcc 1560
ccaccccgcc caagtttagg cactggccag tctggccctc aaatagctgt tgaaggggtg 1620
ggatgttcca ctaattcccc tatcctaccc cgcccctccc agctctttgt agagcaactt 1680
gagtcaactc tgagtcctag cactgggcaa gggaggaaca gctgccgtgg ttagagaagc 1740
agccagattt ccccttcccc acgttaactt ccctggcatt tacaacttga tgccatctgc 1800
ccacctccct tcacccttcc aagtccagct gtcacttcag caggagggag agcaccctcc 1860
ttcattacag cttaccaccc tctcctctgc ctcccaccct ctggcaagcc tggggagcag 1920
ctggcaggaa agagatggca gagctggtgg tggtgagagt agaacctgtt ccgggagcta 1980
tggcagagcc aggctgtctc ttaccttcct attgggtctc tagggaccac accctgcccc 2040
agccctaaat gagaatgcaa gtaacagcca aagacttggg aaaaagcaaa gaacattgtc 2100
tcttgaccct aagtgaccca gaagcgtgca gagatgatga tttgctagtc tgcctattgg 2160
aagaaaggca gtatggtacc ttccacccca ggtcaagtag aacagctcgg tgtgaatcca 2220
gagactgagt catccaagtg agccatgcag gggctggggt catctttgtt actcatcttg 2280
ggggaaggtt gagagaaaga aagttgtggc tggggcctct gatctccctt ctctccaggc 2340
agctctcttt actcagtgtg aatatagaag caggtggtca atggggaaaa ccagaagttc 2400
aggaattctc aggggagtct gtttcagttc ctacccgacc cttgacagtg acccagctgt 2460
ctcccaaaaa gaaggaacag ggtctgccct cccatttcct ccctcccaca ttggcacctc 2520
ctgggctctg ctgtgcccat catttgtgag attggcccag gcctttccct cttcttttcc 2580
tttgctagat gccaccccac tttcagctta gagggcagct aagccaaagc cagattagaa 2640
agggttttgt gttgctgccc acgcctcctc tcattccccg gaaaggaaaa caaaggctca 2700
gtctatcttg gcccctgtca ggtgtcctgc ccactccctc agcccccacc aacccccttcc 2760
ccgctccagc ccccacacat tccagtgggt gggggcaccg gatgtggaat ctcctggctg 2820
agtagagctc tggggtggga agtgaaaaat tcaacagcca ataaaggaga acaattattg 2880
caggggttgg ggagggcaaa aaacactggc agaaggttgg ggacaccaac cccatggtag 2940
taatggtaac cacagcccat accttgattg aaaagaaaaa ctagtgccta aggcagaagg 3000
gagggagagc atgtgtgtgt gtgtgtgtgt gtgtgtttgt gtgtgttcct tgatctgtgt 3060
gggcaaaagc gaaggcttgg gagagcaact gagagccgag aagaaacccc tgggataccc 3120
tcttttgacc cagggttcct ggggaggggg tttgtactcc catcctaacc cggcttcagg 3180
gaggggccca atttccctct ccaacttctt gcatagatcc ctaggcttcc aatcactgcc 3240
agatgtgttc ctcctgctgg attttcccag tttttccatg cccctttttc cctcccagct 3300
ttttcctcag ggatatcacc ccaggttttc cctcccttcc cccactcagc tgcaggaact 3360
cctttttggg gtttggagct ggtatgtttc tagtcagctc cgagcttggc tctcctggga 3420
atcctgggag tgaaaggaag gagctgggtt tatttgcatg tactggtagt catttgcatc 3480
acatccaaaa atggccaaaa ttatgagccc tgattcttgg ctgaactccc actgctgcaa 3540
tggaatatta gtcccggaga ccacccccaa ctagctggag ctgatctcct ccctcctcca 3600
accccccagt gtggcccagg cctacatgaa ccagagaaag ctggaccatg aggtgaagac 3660

-continued

```
cctacaggtc caggctgccc aatttgccaa gcagacaggc cagtggatcg gaatggtgga   3720

gaacttcaac caggcactca aggtgggcca tactccctac ctcaccaccc caatcctggg   3780

cccccattgg ctgcctccag tcaggttacc tcaggtttag gttaaggagg aagtagggtg   3840

gtcccagaaa ccccatctat agccccagtg tcagaaaagg tagagaaaga aagaaaagca   3900

gttggtgggt ccaagtaaag ccttttccag gagatgaata aaacgtattc cccagactgg   3960

aagccatact ctacccattc tgattcctgg gctcccacct cctctccccc ttcccaggaa   4020

attggggatg tggagaactg ggctcggagc atcgagctgg acatgcgcac cattgccact   4080

gcactggaat atgtctacaa agggcagctg cagtctgccc cttcctagcc cctgttccct   4140

cccccaaccc tatccctcct acctcacccg caggggggaag gagggaggct gacaagcctt   4200

gaataaaaca caagcctccg tttctctgtg gtgtgtttca gagagctact agctccagtg   4260

tcgggggtgg gagtggaagg ttcaaaggtg gtttccctga gggacaggta ccttttgggg   4320

agagggtgga actagcttcc tcttactatc ccaactctct tctcctccat ggcccttgtg   4380

caggtgtctg ttaggcaagc agagggtggg agttcccatc cctcctgaga gaaggtccta   4440

gtagccctgc cccaagcttc ctaattcagg acttgtttcc tacagaagag aaacaaggca   4500

aggtacaggc ctggtcccca gctctggctt tctgcctctc cacgtgctca tggcctctcc   4560

caggctaact ctaagcagtg tcatgagtct gagccaggtg ggagattaat tcctgggggc   4620

acttcagggc tgagaagggg gaggaatgac aggtccagta accgttacca acagagcagt   4680

gcagctgcca tccttgacag ctccctcctc cttggagacc atgacataga tggtcaggaa   4740

cccaggctga gaaagacagc caaggggtgg ggggag                            4776
```

<210> SEQ ID NO 3
<211> LENGTH: 462
<212> TYPE: DNA
<213> ORGANISM: Homo sapiens

<400> SEQUENCE: 3

```
atggccccgg ggagccgagg tgagcgttcc agcttccgga gccggagggg gcccggcgta     60

cccagccccc agcccgacgt gaccatgctg tcccgcctcc taaaagaaca ccaggccaag    120

cagaatgaac gcaaggagct gcaggaaaag aggaggcgag aggctatcac tgcagcgacc    180

tgcctgacag aagctttggt ggatcacctc aatgtgggtg tggcccaggc ctacatgaac    240

cagagaaagc tggaccatga ggtgaagacc ctacaggtcc aggctgccca atttgccaag    300

cagacaggcc agtggatcgg aatggtggag aacttcaacc aggcactcaa ggaaattggg    360

gatgtggaga actgggctcg gagcatcgag ctggacatgc gcaccattgc cactgcactg    420

gaatatgtct acaaagggca gctgcagtct gccccttcct ag                       462
```

<210> SEQ ID NO 4
<211> LENGTH: 378
<212> TYPE: DNA
<213> ORGANISM: Homo sapiens

<400> SEQUENCE: 4

```
atgctgtccc gcctcctaaa agaacaccag gccaagcaga atgaacgcaa ggagctgcag     60

gaaaagagga ggcgagaggc tatcactgca gcgacctgcc tgacagaagc tttggtggat    120

cacctcaatg tgggtgtggc ccaggcctac atgaaccaga gaaagctgga ccatgaggtg    180

aagaccctac aggtccaggc tgcccaattt gccaagcaga caggccagtg gatcggaatg    240
```

-continued

```
gtggagaact tcaaccaggc actcaaggaa attggggatg tggagaactg ggctcggagc    300

atcgagctgg acatgcgcac cattgccact gcactggaat atgtctacaa agggcagctg    360

cagtctgccc cttcctag                                                  378
```

<210> SEQ ID NO 5
<211> LENGTH: 42
<212> TYPE: DNA
<213> ORGANISM: Homo sapiens

<400> SEQUENCE: 5

```
agtacaaaga caggaaacgc tggaagtcgt ttggcttgtg gt                        42
```

<210> SEQ ID NO 6
<211> LENGTH: 14
<212> TYPE: PRT
<213> ORGANISM: Homo sapiens

<400> SEQUENCE: 6

```
Ser Thr Lys Thr Gly Asn Ala Gly Ser Arg Leu Ala Cys Gly
1               5                   10
```

<210> SEQ ID NO 7
<211> LENGTH: 42
<212> TYPE: DNA
<213> ORGANISM: Synthetic sequence

<400> SEQUENCE: 7

```
agtacaaaga caggaaacgc tggaagtcgt ttcgcttgtg gt                        42
```

<210> SEQ ID NO 8
<211> LENGTH: 14
<212> TYPE: PRT
<213> ORGANISM: Synthetic sequence

<400> SEQUENCE: 8

```
Ser Thr Lys Thr Gly Asn Ala Gly Ser Arg Phe Ala Cys Gly
1               5                   10
```

<210> SEQ ID NO 9
<211> LENGTH: 13
<212> TYPE: DNA
<213> ORGANISM: Synthetic sequence

<400> SEQUENCE: 9

```
tcgtttggct tgt                                                        13
```

<210> SEQ ID NO 10
<211> LENGTH: 13
<212> TYPE: DNA
<213> ORGANISM: Synthetic sequence

<400> SEQUENCE: 10

```
tcgtttcgct tgt                                                        13
```

<210> SEQ ID NO 11
<211> LENGTH: 41
<212> TYPE: DNA
<213> ORGANISM: Homo sapiens

<400> SEQUENCE: 11

```
ggtggatttg gtaatagcag agggggtgga gctggttggg a                         41
```

-continued

<210> SEQ ID NO 12
<211> LENGTH: 14
<212> TYPE: PRT
<213> ORGANISM: Homo sapiens

<400> SEQUENCE: 12

Gly Gly Phe Gly Asn Ser Arg Gly Gly Gly Ala Gly Leu Gly
1 5 10

<210> SEQ ID NO 13
<211> LENGTH: 41
<212> TYPE: DNA
<213> ORGANISM: Synthetic sequence

<400> SEQUENCE: 13
ggtggatttg gtaatagcag agggggtgga gctagttggg a 41

<210> SEQ ID NO 14
<211> LENGTH: 14
<212> TYPE: PRT
<213> ORGANISM: Synthetic sequence

<400> SEQUENCE: 14

Gly Gly Phe Gly Asn Ser Arg Gly Gly Gly Ala Ser Leu Gly
1 5 10

<210> SEQ ID NO 15
<211> LENGTH: 13
<212> TYPE: DNA
<213> ORGANISM: Synthetic sequence

<400> SEQUENCE: 15
ggagctggtt tgg 13

<210> SEQ ID NO 16
<211> LENGTH: 13
<212> TYPE: DNA
<213> ORGANISM: Synthetic sequence

<400> SEQUENCE: 16
ggagctagtt tgg 13

<210> SEQ ID NO 17
<211> LENGTH: 33
<212> TYPE: DNA
<213> ORGANISM: Homo sapiens

<400> SEQUENCE: 17
cactcacttc cggcgccgag cggcgcgggg cag 33

<210> SEQ ID NO 18
<211> LENGTH: 33
<212> TYPE: DNA
<213> ORGANISM: Synthetic sequence

<400> SEQUENCE: 18
cactcacttc cggcgccgag cggcgcgggg cag 33

<210> SEQ ID NO 19
<211> LENGTH: 27
<212> TYPE: DNA
<213> ORGANISM: Synthetic sequence

<400> SEQUENCE: 19

```
cactcacttc cggccggcgc ggggcag                                    27

<210> SEQ ID NO 20
<211> LENGTH: 24
<212> TYPE: DNA
<213> ORGANISM: Synthetic sequence

<400> SEQUENCE: 20

cactcacttc cggcgccggg gcag                                       24

<210> SEQ ID NO 21
<211> LENGTH: 25
<212> TYPE: RNA
<213> ORGANISM: Artificial Sequence
<220> FEATURE:
<223> OTHER INFORMATION: synthetic sequence

<400> SEQUENCE: 21

caccgaggaa acgctggaag tcgtt                                      25

<210> SEQ ID NO 22
<211> LENGTH: 100
<212> TYPE: DNA
<213> ORGANISM: Artificial Sequence
<220> FEATURE:
<223> OTHER INFORMATION: synthetic sequence

<400> SEQUENCE: 22

acatccaagg gaatgtttat tgggcgatcc caattacacc acaagcgaaa cgacttccag    60

cgtttcctgt ctttgtactt tcttcatttc cacctttgcc                      100

<210> SEQ ID NO 23
<211> LENGTH: 20
<212> TYPE: DNA
<213> ORGANISM: Artificial Sequence
<220> FEATURE:
<223> OTHER INFORMATION: synthetic sequence

<400> SEQUENCE: 23

taagggtagc gtgtggtggt                                            20

<210> SEQ ID NO 24
<211> LENGTH: 22
<212> TYPE: DNA
<213> ORGANISM: Artificial Sequence
<220> FEATURE:
<223> OTHER INFORMATION: synthetic sequence

<400> SEQUENCE: 24

tgcttagaca aataggctgt cc                                         22

<210> SEQ ID NO 25
<211> LENGTH: 25
<212> TYPE: RNA
<213> ORGANISM: Artificial Sequence
<220> FEATURE:
<223> OTHER INFORMATION: synthetic sequence

<400> SEQUENCE: 25

caccgtttgg taatagcaga ggggg                                      25

<210> SEQ ID NO 26
<211> LENGTH: 91
<212> TYPE: DNA
<213> ORGANISM: Artificial Sequence
```

<220> FEATURE:
<223> OTHER INFORMATION: synthetic sequence

<400> SEQUENCE: 26
tttgggaatc agggtggatt tggtaatagc agagggggtg gagctggttt gggaaacaat 60
caaggtagta atatgggtgg tgggatgaac t 91

<210> SEQ ID NO 27
<211> LENGTH: 20
<212> TYPE: DNA
<213> ORGANISM: Artificial Sequence
<220> FEATURE:
<223> OTHER INFORMATION: synthetic sequence

<400> SEQUENCE: 27
ccactacgcc cagctaatgt 20

<210> SEQ ID NO 28
<211> LENGTH: 20
<212> TYPE: DNA
<213> ORGANISM: Artificial Sequence
<220> FEATURE:
<223> OTHER INFORMATION: synthetic sequence

<400> SEQUENCE: 28
tctggctggg gaatgtagac 20

<210> SEQ ID NO 29
<211> LENGTH: 22
<212> TYPE: RNA
<213> ORGANISM: Artificial Sequence
<220> FEATURE:
<223> OTHER INFORMATION: synthetic sequence

<400> SEQUENCE: 29
cttccggcgc cgagcggcgc gg 22

<210> SEQ ID NO 30
<211> LENGTH: 20
<212> TYPE: DNA
<213> ORGANISM: Artificial Sequence
<220> FEATURE:
<223> OTHER INFORMATION: synthetic sequence

<400> SEQUENCE: 30
ggcgctcact tcttcgtgta 20

<210> SEQ ID NO 31
<211> LENGTH: 22
<212> TYPE: DNA
<213> ORGANISM: Artificial Sequence
<220> FEATURE:
<223> OTHER INFORMATION: synthetic sequence

<400> SEQUENCE: 31
agacgtagag gcgagtagag ga 22

<210> SEQ ID NO 32
<211> LENGTH: 21
<212> TYPE: DNA
<213> ORGANISM: Artificial Sequence
<220> FEATURE:
<223> OTHER INFORMATION: synthetic sequence

<400> SEQUENCE: 32
aaggcactga gcgtatcatg t 21

<210> SEQ ID NO 33
<211> LENGTH: 25
<212> TYPE: DNA
<213> ORGANISM: Artificial Sequence
<220> FEATURE:
<223> OTHER INFORMATION: synthetic sequence

<400> SEQUENCE: 33
tgaagataca cttccttctt gaaca 25

<210> SEQ ID NO 34
<211> LENGTH: 20
<212> TYPE: DNA
<213> ORGANISM: Artificial Sequence
<220> FEATURE:
<223> OTHER INFORMATION: synthetic sequence

<400> SEQUENCE: 34
tgctgagtcc gcagcaggtg 20

<210> SEQ ID NO 35
<211> LENGTH: 20
<212> TYPE: DNA
<213> ORGANISM: Artificial Sequence
<220> FEATURE:
<223> OTHER INFORMATION: synthetic sequence

<400> SEQUENCE: 35
gctggcaggc tctggggaag 20

<210> SEQ ID NO 36
<211> LENGTH: 18
<212> TYPE: DNA
<213> ORGANISM: Artificial Sequence
<220> FEATURE:
<223> OTHER INFORMATION: synthetic sequence

<400> SEQUENCE: 36
ccaaccgcga gaagatga 18

<210> SEQ ID NO 37
<211> LENGTH: 20
<212> TYPE: DNA
<213> ORGANISM: Artificial Sequence
<220> FEATURE:
<223> OTHER INFORMATION: synthetic sequence

<400> SEQUENCE: 37
ccagaggcgt acagggatag 20

<210> SEQ ID NO 38
<211> LENGTH: 19
<212> TYPE: DNA
<213> ORGANISM: Artificial Sequence
<220> FEATURE:
<223> OTHER INFORMATION: synthetic sequence

<400> SEQUENCE: 38
tatggcgacc cgcagccct 19

<210> SEQ ID NO 39
<211> LENGTH: 21
<212> TYPE: DNA
<213> ORGANISM: Artificial Sequence -continued

```
<220> FEATURE:
<223> OTHER INFORMATION: synthetic sequence

<400> SEQUENCE: 39

catctcgagc aagacgttca g                                              21
```